United States Patent
Rohlff et al.

(10) Patent No.: US 9,447,178 B2
(45) Date of Patent: *Sep. 20, 2016

(54) THERAPEUTIC AND DIAGNOSTIC TARGET

(75) Inventors: Christian Rohlff, Abingdon (GB); Alasdair Stamps, Abingdon (GB)

(73) Assignee: Oxford BioTherapeutics Ltd., Abingdon (GB)

( * ) Notice: Subject to any disclaimer, the term of this patent is extended or adjusted under 35 U.S.C. 154(b) by 176 days.

This patent is subject to a terminal disclaimer.

(21) Appl. No.: 14/127,788

(22) PCT Filed: Jun. 28, 2012

(86) PCT No.: PCT/IB2012/001680
§ 371 (c)(1),
(2), (4) Date: Feb. 25, 2014

(87) PCT Pub. No.: WO2013/001369
PCT Pub. Date: Jan. 3, 2013

(65) Prior Publication Data
US 2014/0193333 A1 Jul. 10, 2014

Related U.S. Application Data

(60) Provisional application No. 61/502,160, filed on Jun. 28, 2011.

(51) Int. Cl.
| | | |
|---|---|---|
| *A61K 39/395* | (2006.01) |
| *C07K 16/18* | (2006.01) |
| *A61K 39/00* | (2006.01) |
| *C07K 16/00* | (2006.01) |
| *C07K 16/28* | (2006.01) |
| *C07K 16/30* | (2006.01) |
| *C12Q 1/68* | (2006.01) |
| *G01N 33/574* | (2006.01) |
| *C07K 14/435* | (2006.01) |
| *G01N 33/566* | (2006.01) |

(52) U.S. Cl.
CPC .......... *C07K 16/18* (2013.01); *A61K 39/0011* (2013.01); *C07K 14/435* (2013.01); *C07K 16/005* (2013.01); *C07K 16/2896* (2013.01); *C07K 16/30* (2013.01); *C12Q 1/6886* (2013.01); *G01N 33/566* (2013.01); *G01N 33/57426* (2013.01); *C07K 2317/55* (2013.01); *C07K 2317/732* (2013.01); *C07K 2317/77* (2013.01); *C12Q 2600/158* (2013.01); *G01N 2500/04* (2013.01)

(58) Field of Classification Search
None
See application file for complete search history.

(56) References Cited

U.S. PATENT DOCUMENTS

| 6,414,113 | B1 * | 7/2002 | Sato | C07K 7/08 424/184.1 |
|---|---|---|---|---|
| 9,175,092 | B2 * | 11/2015 | Rohlff | C07K 16/40 |
| 2009/0232822 | A1 | 9/2009 | Joseloff et al. | |
| 2013/0273068 | A1 | 10/2013 | Rohlff et al. | |
| 2016/0002354 | A1 | 1/2016 | Rohlff et al. | |

FOREIGN PATENT DOCUMENTS

| JP | 2005-295921 | 10/2005 |
| WO | 2011/027310 A1 | 3/2011 |

OTHER PUBLICATIONS

Kataja et al., Ann Oncol 2009; 20(sup 4): iv10-14.*
Nelson et al., Ann. Intern Med. 2009; 151:727-737.*
Balmana et al. Ann Oncol 2009; 20(supp 4):iv19-20.*
Freshney (Culture of Animal Cells, A Manual of Basic Technique, Alan R. Liss, Inc., 1983, New York, p. 4).*
Jain (Sci. Am., 1994, 271:58-65).*
Gura (Science, 1997, 278:1041-1042.*
Dermer (Bio/Technology, 1994, 12:320).*
Brown, McKay et al., "Tolerance to Single, but Not Multiple, Amino Acid Replacements in Antibody VH CDR2," The Journal of Immunology, vol. 156:3285-3291 (1996).
Bruono, Nicola Lo et al., "The CD157-Integrin Partnership Controls Transendothelial Migration and Adhesion of Human Monocytes," The Journal of Biological Chemistry, vol. 286(21):18681-18691 (2011).
Cedarlane Laboratories Limited, "Purified Anti-Mouse CD157 Receptor Monoclonal Antibody," retrieved online at www.cedarlanelabs.com, 3 pages (2008).
Funaro, Ada et al., "CD157 is an important mediator of neutrophil adhesion and migration," Blood, vol. 104 (13):4269-4278 (2004).
Ishihara, Katsuhiko et al., "BST-1/CD157 Regulates the Humoral Immune Responses in vivo," Chem. Immunol., vol. 75:235-255 (2000).
Kaisho, Tsuneyasu et al., "BST-1, a surface molecule of bone marrow stromal cell lines that facilitates pre-B-cell growth," Proc. Natl. Acad. Sci. USA, vol. 91:5325-5329 (1994).
Liu, Sue M. et al., "Immune cell transcriptome datasets reveal novel leukocyte subset-specific genes and genes associated with allergic processes," J. Allergy Clin. Immunol., vol. 118:496-503 (2006).
Malavasi, Fabio et al., "Evolution and Function of the ADP Ribosyl Cyclase/CD38 Gene Family in Physiology and Pathology," Physiol. Rev., vol. 88:841-886 (2008).
McNagny, Kelly M. et al., "A Cell Surface Glycoprotein that Marks Early B Lineage Cells and Mature Myeloid Lineage Cells in Mice," The Journal of Immunology, vol. 141(8):2551-2556 (1988).

(Continued)

*Primary Examiner* — Sheela J Huff
(74) *Attorney, Agent, or Firm* — Nelson Mullins Riley & Scarborough LLP; Jane E. Remillard, Esq.; Jill Gorny Sloper, Esq.

(57) ABSTRACT

The present invention provides methods and compositions for treatment, screening, diagnosis and prognosis of acute myeloid leukemia (AML), B-cell chronic lymphocytic leukemia, breast cancer, colorectal cancer, kidney cancer, head and neck cancer, lung cancer, ovarian cancer or pancreatic cancer, for monitoring the effectiveness of acute myeloid leukemia (AML), B-cell chronic lymphocytic leukemia, breast cancer, colorectal cancer, kidney cancer, head and neck cancer, lung cancer, ovarian cancer or pancreatic cancer treatment, and for drug development. The present invention also provides methods and compositions for depletion of immune cells to treat inflammatory diseases.

14 Claims, 11 Drawing Sheets

(56) References Cited

OTHER PUBLICATIONS

Okuyama, Yoshiki et al., "Human BST-1 Expressed on Myeloid Cells Functions as a Receptor Molecule," Biochemical and Biophysical Research Communications, vol. 228:838-845 (1996).
Ortolan, Erika et al., "Functional Role and PRognostic Significance of CD157 in Ovarian Carcinoma," J. Natl. Cancer Inst., vol. 102:1160-1177 (2010).
Rudikoff, Stuart et al., "Single amino acid substitution altering antigen-binding specificity," Proc. Natl. Acad. Sci. USA, vol. 79:1979-1983 (1982).
Seki, Mizue et al., "An Immature Rat Lymphocyte Marker CD157: Striking Differences in the Expression between Mice and Rats," Immunbiol., vol. 203:725-742 (2001).
Sposato, P. et al., "Analysis of human CD157 by murine monoclonal antibodies (MoAbs)," Tissue Antigens, 7th Workshop and Conference on Human Leucocyte Differentiation Antigens, vol. 55(Suppl. 1):71, Poster Presentation No. L. 10 (2000).
Todd, Robert F., III et al., "The Modulated Expression of Mo5, a Human Myelomonocytic Plasma Membrane Antigen," Blood, vol. 65(4):964-973 (1985).
Vajdos, Felix F. et al., "Comprehensive Functional Maps of the Antigen-binding Site of an Anti-ErbB2 Antibody Obtained with Shotgun Scanning Mutagenesis," J. Mol. Biol., vol. 320:415-428 (2002).
International Search Report and Written Opinion for Application No. PCT/US2012/044703, 20 pages, dated May 24, 2013.
International Preliminary Report on Patentability and Written Opinion for Application No. PCT/US2012/044703, 12 pages, dated Jan. 7, 2014.
International Search Report for Application No. PCT/IB2012/001680, 3 pages, dated Mar. 13, 2013.
International Preliminary Report on Patentability and Written Opinion for Application No. PCT/IB2012/001680, 8 pages, dated Jan. 7, 2014.
Carter, P.J. "Potent Antibody Therapeutics by Design," The Journal of Immunology, Nature Pub. Group, vol. 6, pp. 343-357 (2006).
Harris, P. et al, "Distinct activities of interferon-gamma, lymphokine and cytokine differentiation-inducing factors acting on the human monoblastic leukemia cell line U937," Cancer Research, vol. 45, pp. 9-13 (1985).
Harris, P., "Human leukemic models of myelomonocytic development: a review of the HL-60 and U937 cell lines," Journal of Leukocyte Biology, vol. 37, pp. 407-422 (1985).
Hu, S. et al., "Activity of the multikinase inhibitor sorafenib in combination with cytarabine in acute myeloid leukemia," JNCI, vol. 103(11), pp. 893-905 (2011).
Hu, S. et al., "Comparison of antitumor effects of multitargeted tyrosine kinase inhibitors in acute myelogenous leukemia," Mol Cancer Therapy, vol. 7(5), pp. 1110-1120 (2008).
Kohls, MD et al., "Mab-ZAP: a tool for evaluating antibody efficacy for use in an immunotoxin," Biotechniques, vol. 28 (1), pp. 162-165 (2000).
Koyama, T. et al, "All-trans retinoic acid upregulates thrombomodulin and downregulates tissue-factor expression in acute promyelocytic leukemia cells: distinct expression of thrombomodulin and tissue factor in human leukemic cells," Blood, vol. 84(9), pp. 3001-3009 (1994).
Krzykowska-Petitjean, K. et al., "Tipifarnib and tanespimycin show synergic proapoptotic activity in U937 cells," J Cancer Res Clin Oncol., vol. 138, pp. 537-544 (2012).
Nimmerjahn, F. et al., "Antibodies, Fc receptors and cancer," Current Opinion in Immunology, vol. 19 (2), pp. 239-245 (2007).
Saito, T. et al., "Anticoagulant effects of retinoic acids on leukemia cells," Blood, vol. 87(2), pp. 657-665 (1996).
Sato, A. et al., "Novel Peptide Inhibitor of ecto-ADP-ribosyl cyclase of bone marrow stromal cell antigen-1 (BST-1/ CD157)," Biochem. J., vol. 337, pp. 491-496 (1999).
Winkler K., et al., "Changing the antigen binding specificity by single point mutations of an anti-p24 (HIV-1) antibody," The Journal of Immunology, The American Association of Immunologists, vol. 165 (8), pp. 4505-4514, 1 (2000).
U.S. Appl. No. 13/840,828, C. Rohlff, filed Mar. 15, 2012, Jun. 23, 2015.
U.S. Appl. No. 13/840,828, C. Rohlff, filed Mar. 15, 2012, Jan. 12, 2015.

* cited by examiner

Figure 1A

Peptide Source: LC/MS Breast Cancer

BST1 (SEQ ID No: 1)
MAAQGCAASRLLQLLIQLLLLLLLLAAGGARARWRGEGTSAHLRDIFLGRCAEYRALLSP
EQRNKNCTAIWEAFKVALDKDPCSVLPSDYDLFTNLSRHSIPRDKSLFWENSHLLVNSFA
DNTRRFMPLSDVLYGRVADFLSWCRQKNDSGLDYQSCPTSEDCENNPVDSFWKRASIQYS
KDSSGVIHVMLNGSEPTGAYPIKGFFADYEIPNLQKEKITRIEIWVMHEIGGPNVESCGE
GSMKVLEKRLKDMGFQYSCINDYRPVKLLQCVDHSTHPDCALKSAAAATQRKAPSLYTEQ
RAGLIIPLFLVLASRTQL

Tandem Peptides (underline):
SEQ ID No: 4  - DMGFQYSCINDYRPVK
SEQ ID No: 5  - FMPLSDVLYGR
SEQ ID No: 7  - GFFADYEIPNLQK
SEQ ID No: 8  - LLQCVDHSTHPDCALK
SEQ ID No: 9  - SLFWENSHLLVNSFADNTR
SEQ ID No: 10 - VADFLSWCR

Figure 1B

Peptide Source: LC/MS Colorectal Cancer

BST1 (SEQ ID No: 1)
MAAQGCAASRLLQLLIQLLLLLLLLAAGGARARWRGEGTSAHLRDIFLGRCAEYRALLSP
EQRNKNCTAIWEAFKVALDKDPCSVLPSDYDLFTNLSRHSIPRDKSLFWENSHLLVNSFA
DNTRRFMPLSDVLYGRVADFLSWCRQKNDSGLDYQSCPTSEDCENNPVDSFWKRASIQYS
KDSSGVIHVMLNGSEPTGAYPIKGFFADYEIPNLQKEKITRIEIWVMHEIGGPNVESCGE
GSMKVLEKRLKDMGFQYSCINDYRPVKLLQCVDHSTHPDCALKSAAAATQRKAPSLYTEQ
RAGLIIPLFLVLASRTQL

Tandem Peptides (underline):
SEQ ID No: 2  - ALLSPEQR
SEQ ID No: 5  - FMPLSDVLYGR
SEQ ID No: 7  - GFFADYEIPNLQK
SEQ ID No: 8  - LLQCVDHSTHPDCALK
SEQ ID No: 9  - SLFWENSHLLVNSFADNTR
SEQ ID No: 10 - VADFLSWCR

Figure 1C

Peptide Source: LC/MS Kidney Cancer

BST1 (SEQ ID No: 1)
MAAQGCAASRLLQLLIQLLLLLLLLAAGGARARWRGEGTSAHLRDIFLGRCAEYRALLSP
EQRNKNCTAIWEAFKVALDKDPCSVLPSDYDLFTNLSRHSIPRDKSLFWENSHLLVNSFA
DNTRRFMPLSDVLYGRVADFLSWCRQKNDSGLDYQSCPTSEDCENNPVDSFWKRASIQYS
KDSSGVIHVMLNGSEPTGAYPIKGFFADYEIPNLQKEKITRIEIWVMHEIGGPNVESCGE
GSMKVLEKRLKDMGFQYSCINDYRPVKLLQCVDHSTHPDCALKSAAAATQRKAPSLYTEQ
RAGLIIPLFLVLASRTQL

Tandem Peptides (underline):
SEQ ID No: 7  - GFFADYEIPNLQK
SEQ ID No: 8  - LLQCVDHSTHPDCALK
SEQ ID No: 10 - VADFLSWCR

Figure 1D

Peptide Source: LC/MS Lung Cancer

BST1 (SEQ ID No: 1)
MAAQGCAASRLLQLLLQLLLLLLLLAAGGARARWRGEGTSAHLRDIFLGRCAEYRALLSP
EQRNKNCTAIWEAFKVALDKDPCSVLPSDYDLFINLSRHSIPRDKSLFWENSHLLVNSFA
DNTRRFMPLSDVLYGRVADFLSWCRQKNDSGLDYQSCPTSEDCENNPVDSFWKRASIQYS
KDSSGVIHVMLNGSEPTGAYPIKGFFADYEIPNLQKEKITRIEIWVMHEIGGPNVESCGE
GSMKVLEKRLKDMGFQYSCINDYRPVKLLQCVDHSTHPDCALKSAAAATQRKAPSLYTEQ
RAGLIIPLFLVLASRTQL

Tandem Peptides (underline):
SEQ ID No: 2 - ALLSPEQR
SEQ ID No: 3 - DIFLGR
SEQ ID No: 5 - FMPLSDVLYGR
SEQ ID No: 7 - GFFADYEIPNLQK
SEQ ID No: 8 - LLQCVDHSTHPDCALK
SEQ ID No: 10 - VADFLSWCR
SEQ ID No: 11 - SLFWENSHLLVN
SEQ ID No: 12 - LKDMGFQYSCINDYRPVK

Figure 1E

Peptide Source: LC/MS Pancreatic Cancer

BST1 (SEQ ID No: 1)
MAAQGCAASRLLQLLLQLLLLLLLLAAGGARARWRGEGTSAHLRDIFLGRCAEYRALLSP
EQRNKNCTAIWEAFKVALDKDPCSVLPSDYDLFINLSRHSIPRDKSLFWENSHLLVNSFA
DNTRRFMPLSDVLYGRVADFLSWCRQKNDSGLDYQSCPTSEDCENNPVDSFWKRASIQYS
KDSSGVIHVMLNGSEPTGAYPIKGFFADYEIPNLQKEKITRIEIWVMHEIGGPNVESCGE
GSMKVLEKRLKDMGFQYSCINDYRPVKLLQCVDHSTHPDCALKSAAAATQRKAPSLYTEQ
RAGLIIPLFLVLASRTQL

Tandem Peptides (underline):
SEQ ID No: 2 - ALLSPEQR
SEQ ID No: 3 - DIFLGR
SEQ ID No: 5 - FMPLSDVLYGR
SEQ ID No: 7 - GFFADYEIPNLQK
SEQ ID No: 10 - VADFLSWCR

Figure 1F

Peptide Source: LC/MS Head and Neck Cancer

BST1 (SEQ ID No: 1)
MAAQGCAASRLLQLLLQLLLLLLLLAAGGARARWRGEGTSAHLRDIFLGRCAEYRALLSP
EQRNKNCTAIWEAFKVALDKDPCSVLPSDYDLFINLSRHSIPRDKSLFWENSHLLVNSFA
DNTRRFMPLSDVLYGRVADFLSWCRQKNDSGLDYQSCPTSEDCENNPVDSFWKRASIQYS
KDSSGVIHVMLNGSEPTGAYPIKGFFADYEIPNLQKEKITRIEIWVMHEIGGPNVESCGE
GSMKVLEKRLKDMGFQYSCINDYRPVKLLQCVDHSTHPDCALKSAAAATQRKAPSLYTEQ
RAGLIIPLFLVLASRTQL

Tandem Peptides (underline):
SEQ ID No: 2 - ALLSPEQR
SEQ ID No: 5 - FMPLSDVLYGR
SEQ ID No: 8 - LLQCVDHSTHPDCALK
SEQ ID No: 10 - VADFLSWCR

Figure 1G

Peptide Source: LC/MS Ovarian Cancer

BST1 (SEQ ID No: 1)
MAAQGCAASRLLQLLLQLLLLLLLLAAGGARARWR<u>GEGTSAHLR</u>DIFLGRCAEYR<u>ALLSP
EQR</u>NKNCTAIWEAFKVALDKDPCSVLPSDYDLFINLSRHSIPRDKSLFWENSHLLVNSFA
DNTRR<u>FMPLSDVLYGR</u>V<u>ADFLSWCR</u>QKNDSGLDYQSCPTSEDCENNPVDSFWKRASIQYS
KDSSGVIHVMLNGSEPTGAYPIKG<u>FFADYEIPNLQK</u>EKITRIEIWVMHEIGGPNVESCGE
GSMKVLEKRLKDMGFQYSCINDYRPVK<u>LLQCVDHSTHPDCALK</u>SAAAATQRKAPSLYTEQ
RAGLIIPLFLVLASRTQL

Tandem Peptides (underline):
```
SEQ ID No:  2 - ALLSPEQR
SEQ ID No:  5 - FMPLSDVLYGR
SEQ ID No:  6 - GEGTSAHLR
SEQ ID No:  7 - GFFADYEIPNLQK
SEQ ID No:  8 - LLQCVDHSTHPDCALK
SEQ ID No: 10 - VADFLSWCR
```

Figure 2

Peptide Source: iTRAQ Lung Cancer

BST1 (SEQ ID No: 1)
MAAQGCAASRLLQLLLQLLLLLLLLAAGGARARWR<u>GEGTSAHLR</u>DIFLGRCAEYRALLSP
EQRNKNCTAIWEAFKVALDKDPCSVLPSDYDLFINLSRHSIPRDKSLFWENSHLLVNSFA
DNTRRFMPLSDVLYGRVADFLSWCRQKNDSGLDYQSCPTSEDCENNPVDSFWKRASIQYS
KDSSGVIHVMLNGSEPTGAYPIKGFFADYEIPNLQKEKITRIEIWVMHEIGGPNVESCGE
GSMKVLEKRLKDMGFQYSCINDYRPVKLLQCVDHSTHPDCALKSAAAATQRKAPSLYTEQ
RAGLIIPLFLVLASRTQL

Tandem Peptides (underline):
```
SEQ ID No:  6 - GEGTSAHLR
```

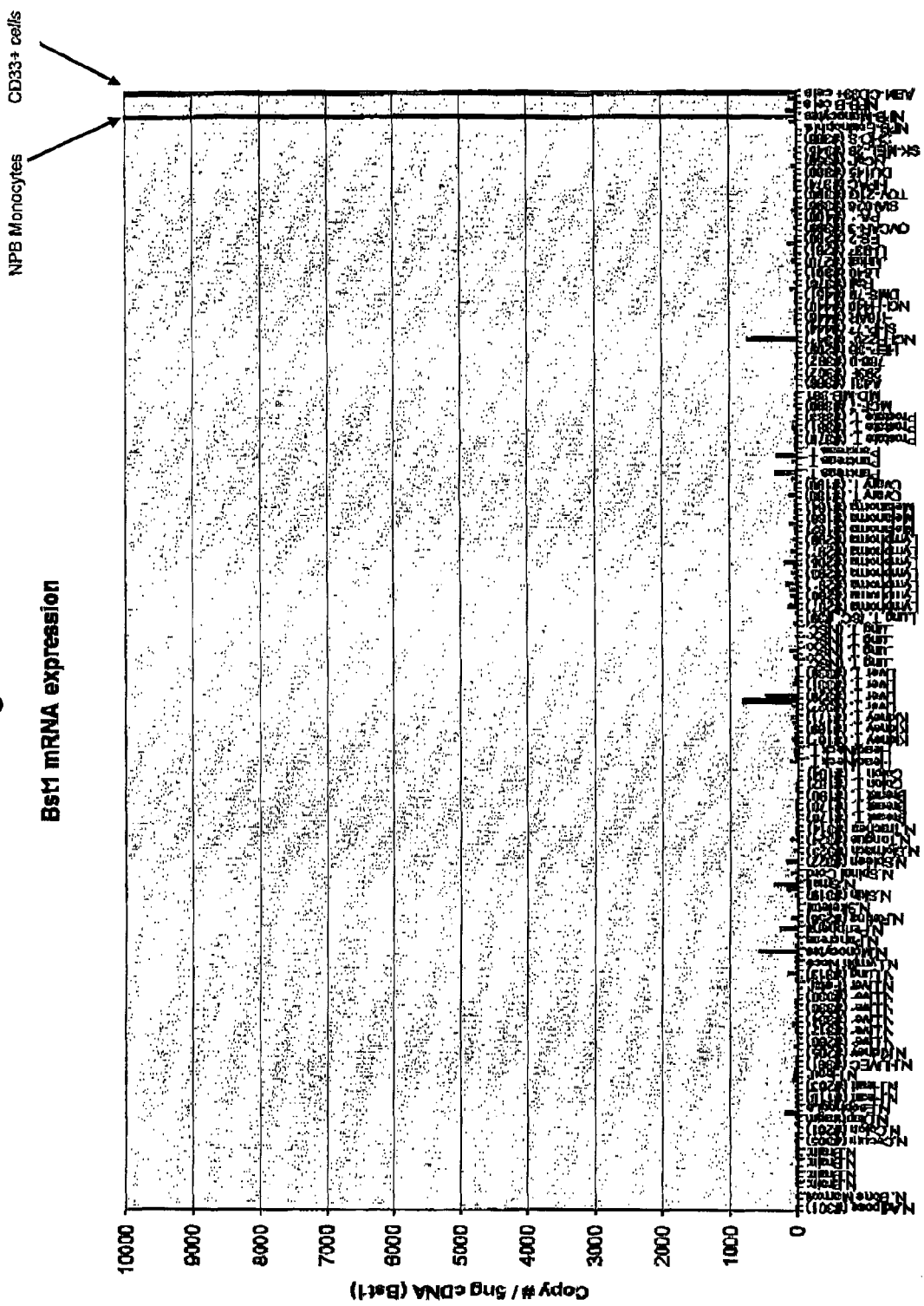

Internalization: BST1_A2 vs H226

Internalization: BST1_A2 vs A549

SEQUENCE LISTING

<160> NUMBER OF SEQ ID NOS: 21

<210> SEQ ID NO 1
<211> LENGTH: 318
<212> TYPE: PRT
<213> ORGANISM: Homo sapiens

<400> SEQUENCE: 1

```
Met Ala Ala Gln Gly Cys Ala Ala Ser Arg Leu Leu Gln Leu Leu Leu
1               5                   10                  15

Gln Leu Leu Leu Leu Leu Leu Leu Ala Ala Gly Gly Ala Arg Ala
            20                  25                  30

Arg Trp Arg Gly Glu Gly Thr Ser Ala His Leu Arg Asp Ile Phe Leu
        35                  40                  45

Gly Arg Cys Ala Glu Tyr Arg Ala Leu Leu Ser Pro Glu Gln Arg Asn
    50                  55                  60

Lys Asn Cys Thr Ala Ile Trp Glu Ala Phe Lys Val Ala Leu Asp Lys
65                  70                  75                  80

Asp Pro Cys Ser Val Leu Pro Ser Asp Tyr Asp Leu Phe Ile Asn Leu
                85                  90                  95

Ser Arg His Ser Ile Pro Arg Asp Lys Ser Leu Phe Trp Glu Asn Ser
            100                 105                 110

His Leu Leu Val Asn Ser Phe Ala Asp Asn Thr Arg Arg Phe Met Pro
        115                 120                 125

Leu Ser Asp Val Leu Tyr Gly Arg Val Ala Asp Phe Leu Ser Trp Cys
    130                 135                 140

Arg Gln Lys Asn Asp Ser Gly Leu Asp Tyr Gln Ser Cys Pro Thr Ser
145                 150                 155                 160

Glu Asp Cys Glu Asn Asn Pro Val Asp Ser Phe Trp Lys Arg Ala Ser
                165                 170                 175

Ile Gln Tyr Ser Lys Asp Ser Ser Gly Val Ile His Val Met Leu Asn
            180                 185                 190

Gly Ser Glu Pro Thr Gly Ala Tyr Pro Ile Lys Gly Phe Phe Ala Asp
        195                 200                 205
```

```
Tyr Glu Ile Pro Asn Leu Gln Lys Glu Lys Ile Thr Arg Ile Glu Ile
    210                 215                 220

Trp Val Met His Glu Ile Gly Gly Pro Asn Val Glu Ser Cys Gly Glu
225                 230                 235                 240

Gly Ser Met Lys Val Leu Glu Lys Arg Leu Lys Asp Met Gly Phe Gln
                245                 250                 255

Tyr Ser Cys Ile Asn Asp Tyr Arg Pro Val Lys Leu Leu Gln Cys Val
                260                 265                 270

Asp His Ser Thr His Pro Asp Cys Ala Leu Lys Ser Ala Ala Ala Ala
                275                 280                 285

Thr Gln Arg Lys Ala Pro Ser Leu Tyr Thr Glu Gln Arg Ala Gly Leu
    290                 295                 300

Ile Ile Pro Leu Phe Leu Val Leu Ala Ser Arg Thr Gln Leu
305                 310                 315
```

<210> SEQ ID NO 2
<211> LENGTH: 8
<212> TYPE: PRT
<213> ORGANISM: Artificial Sequence
<220> FEATURE:
<223> OTHER INFORMATION: Synthetic protein

<400> SEQUENCE: 2

```
Ala Leu Leu Ser Pro Glu Gln Arg
1               5
```

<210> SEQ ID NO 3
<211> LENGTH: 6
<212> TYPE: PRT
<213> ORGANISM: Artificial Sequence
<220> FEATURE:
<223> OTHER INFORMATION: Synthetic protein

<400> SEQUENCE: 3

```
Asp Ile Phe Leu Gly Arg
1               5
```

<210> SEQ ID NO 4
<211> LENGTH: 16
<212> TYPE: PRT
<213> ORGANISM: Artificial Sequence
<220> FEATURE:
<223> OTHER INFORMATION: Synthetic protein

<400> SEQUENCE: 4

```
Asp Met Gly Phe Gln Tyr Ser Cys Ile Asn Asp Tyr Arg Pro Val Lys
1               5                   10                  15
```

<210> SEQ ID NO 5
<211> LENGTH: 11
<212> TYPE: PRT
<213> ORGANISM: Artificial Sequence
<220> FEATURE:
<223> OTHER INFORMATION: Synthetic protein

<400> SEQUENCE: 5

```
Phe Met Pro Leu Ser Asp Val Leu Tyr Gly Arg
1               5                   10
```

<210> SEQ ID NO 6
<211> LENGTH: 9
<212> TYPE: PRT
<213> ORGANISM: Artificial Sequence
<220> FEATURE:

<223> OTHER INFORMATION: Synthetic protein

<400> SEQUENCE: 6

Gly Glu Gly Thr Ser Ala His Leu Arg
1               5

<210> SEQ ID NO 7
<211> LENGTH: 13
<212> TYPE: PRT
<213> ORGANISM: Artificial Sequence
<220> FEATURE:
<223> OTHER INFORMATION: Synthetic protein

<400> SEQUENCE: 7

Gly Phe Phe Ala Asp Tyr Glu Ile Pro Asn Leu Gln Lys
1               5                   10

<210> SEQ ID NO 8
<211> LENGTH: 16
<212> TYPE: PRT
<213> ORGANISM: Artificial Sequence
<220> FEATURE:
<223> OTHER INFORMATION: Synthetic protein

<400> SEQUENCE: 8

Leu Leu Gln Cys Val Asp His Ser Thr His Pro Asp Cys Ala Leu Lys
1               5                   10                  15

<210> SEQ ID NO 9
<211> LENGTH: 19
<212> TYPE: PRT
<213> ORGANISM: Artificial Sequence
<220> FEATURE:
<223> OTHER INFORMATION: Synthetic protein

<400> SEQUENCE: 9

Ser Leu Phe Trp Glu Asn Ser His Leu Leu Val Asn Ser Phe Ala Asp
1               5                   10                  15

Asn Thr Arg

<210> SEQ ID NO 10
<211> LENGTH: 9
<212> TYPE: PRT
<213> ORGANISM: Artificial Sequence
<220> FEATURE:
<223> OTHER INFORMATION: Synthetic protein

<400> SEQUENCE: 10

Val Ala Asp Phe Leu Ser Trp Cys Arg
1               5

<210> SEQ ID NO 11
<211> LENGTH: 12
<212> TYPE: PRT
<213> ORGANISM: Artificial Sequence
<220> FEATURE:
<223> OTHER INFORMATION: Synthetic protein

<400> SEQUENCE: 11

Ser Leu Phe Trp Glu Asn Ser His Leu Leu Val Asn
1               5                   10

<210> SEQ ID NO 12
<211> LENGTH: 18
<212> TYPE: PRT
<213> ORGANISM: Artificial Sequence
<220> FEATURE:
<223> OTHER INFORMATION: Synthetic protein

<400> SEQUENCE: 12

Leu Lys Asp Met Gly Phe Gln Tyr Ser Cys Ile Asn Asp Tyr Arg Pro
1               5                   10                  15

Val Lys

<210> SEQ ID NO 13
<211> LENGTH: 264
<212> TYPE: PRT
<213> ORGANISM: Homo sapiens

<400> SEQUENCE: 13

Gly Ala Arg Ala Arg Trp Arg Gly Glu Gly Thr Ser Ala His Leu Arg
1               5                   10                  15

Asp Ile Phe Leu Gly Arg Cys Ala Glu Tyr Arg Ala Leu Leu Ser Pro
                20                  25                  30

Glu Gln Arg Asn Lys Asn Cys Thr Ala Ile Trp Glu Ala Phe Lys Val
            35                  40                  45

Ala Leu Asp Lys Asp Pro Cys Ser Val Leu Pro Ser Asp Tyr Asp Leu
        50                  55                  60

Phe Ile Asn Leu Ser Arg His Ser Ile Pro Arg Asp Lys Ser Leu Phe
65                  70                  75                  80

Trp Glu Asn Ser His Leu Leu Val Asn Ser Phe Ala Asp Asn Thr Arg
                85                  90                  95

Arg Phe Met Pro Leu Ser Asp Val Leu Tyr Gly Arg Val Ala Asp Phe
                100                 105                 110

Leu Ser Trp Cys Arg Gln Lys Asn Asp Ser Gly Leu Asp Tyr Gln Ser
            115                 120                 125

Cys Pro Thr Ser Glu Asp Cys Glu Asn Asn Pro Val Asp Ser Phe Trp
        130                 135                 140

Lys Arg Ala Ser Ile Gln Tyr Ser Lys Asp Ser Ser Gly Val Ile His
145                 150                 155                 160

Val Met Leu Asn Gly Ser Glu Pro Thr Gly Ala Tyr Pro Ile Lys Gly
                165                 170                 175

Phe Phe Ala Asp Tyr Glu Ile Pro Asn Leu Gln Lys Glu Lys Ile Thr
                180                 185                 190

Arg Ile Glu Ile Trp Val Met His Glu Ile Gly Gly Pro Asn Val Glu
            195                 200                 205

Ser Cys Gly Glu Gly Ser Met Lys Val Leu Glu Lys Arg Leu Lys Asp
        210                 215                 220

Met Gly Phe Gln Tyr Ser Cys Ile Asn Asp Tyr Arg Pro Val Lys Leu
225                 230                 235                 240

Leu Gln Cys Val Asp His Ser Thr His Pro Asp Cys Ala Leu Lys Ser
                245                 250                 255

Ala Ala Ala Ala Thr Gln Arg Lys
            260

<210> SEQ ID NO 14
<211> LENGTH: 253
<212> TYPE: PRT
<213> ORGANISM: Artificial Sequence
<220> FEATURE:
<223> OTHER INFORMATION: Synthetic protein

<400> SEQUENCE: 14

Met Lys Gln Ser Thr Ile Ala Leu Ala Leu Leu Pro Leu Leu Phe Thr
1               5                   10                  15

Pro Val Ala Lys Ala Gln Val Lys Leu Gln Gln Ser Gly Ala Glu Leu
            20                  25                  30

Val Arg Pro Gly Ser Ser Val Lys Ile Ser Cys Lys Ala Ser Gly Tyr
        35                  40                  45

Ala Phe Ser Asn Ser Trp Ile Asn Trp Val Lys Gln Arg Pro Gly Gln
    50                  55                  60

Gly Leu Glu Trp Ile Gly Gln Ile Tyr Pro Gly Asp Tyr Asp Thr Asn
65                  70                  75                  80

Tyr Asn Gly Lys Phe Lys Gly Lys Ala Thr Leu Thr Ala Asp Tyr Ser
                85                  90                  95

Ser Ser Thr Ala Tyr Met Gln Leu Asn Ser Leu Thr Ser Glu Asp Ser
            100                 105                 110

Ala Val Tyr Phe Cys Ala Arg Gly Gly Ser Ile Tyr Tyr Gly Asn Leu
        115                 120                 125

Gly Phe Phe Asp Val Trp Gly Ala Gly Thr Thr Val Thr Val Ser Ser
    130                 135                 140

Ala Lys Thr Thr Pro Pro Ser Val Tyr Pro Leu Ala Pro Gly Ser Ala
145                 150                 155                 160

Ala Gln Thr Asn Ser Met Val Thr Leu Gly Cys Leu Val Lys Gly Tyr
                165                 170                 175

Phe Pro Glu Pro Val Thr Val Thr Trp Asn Ser Gly Ser Leu Ser Ser
            180                 185                 190

Gly Val His Thr Phe Pro Ala Val Leu Gln Ser Asp Leu Tyr Thr Leu
        195                 200                 205

Ser Ser Ser Val Thr Val Pro Ser Ser Thr Trp Pro Ser Glu Thr Val
210                 215                 220

Thr Cys Asn Val Ala His Pro Ala Ser Ser Thr Lys Val Asp Lys Lys
225                 230                 235                 240

Ile Val Pro Arg Asp Cys His His His His His His
                245                 250

<210> SEQ ID NO 15
<211> LENGTH: 237
<212> TYPE: PRT
<213> ORGANISM: Artificial Sequence
<220> FEATURE:
<223> OTHER INFORMATION: Synthetic protein

<400> SEQUENCE: 15

Met Lys Tyr Leu Leu Pro Thr Ala Ala Gly Leu Leu Leu Leu Ala
1               5                   10                  15

Ala Gln Pro Ala Met Ala Glu Met Val Leu Thr Gln Ser Pro Ala Ile
            20                  25                  30

Met Ser Thr Ser Leu Gly Glu Arg Val Thr Met Thr Cys Thr Ala Ser
        35                  40                  45

Ser Arg Val Ser Ser Ser Tyr Leu His Trp Tyr Gln Gln Lys Pro Gly
    50                  55                  60

Ser Ser Pro Lys Leu Trp Ile Tyr Ser Thr Ser Asn Leu Ala Ser Gly
65                  70                  75                  80

Val Pro Ala Arg Phe Ser Gly Ser Gly Ser Gly Thr Ser Tyr Ser Leu
                85                  90                  95

Thr Ile Ser Ser Met Glu Ala Glu Asp Ala Ala Thr Tyr Tyr Cys His
            100                 105                 110

Gln Tyr His Arg Ser Pro Tyr Thr Phe Gly Gly Thr Lys Leu Glu
            115                 120                 125

Ile Lys Arg Ala Asp Ala Ala Pro Thr Val Ser Ile Phe Pro Pro Ser
130                 135                 140

Ser Glu Gln Leu Thr Ser Gly Gly Ala Ser Val Val Cys Phe Leu Asn
145                 150                 155                 160

Asn Phe Tyr Pro Lys Asp Ile Asn Val Lys Trp Lys Ile Asp Gly Ser
                165                 170                 175

Glu Arg Gln Asn Gly Val Leu Asn Ser Trp Thr Asp Gln Asp Ser Lys
            180                 185                 190

Asp Ser Thr Tyr Ser Met Ser Ser Thr Leu Thr Leu Thr Lys Asp Glu
            195                 200                 205

Tyr Glu Arg His Asn Ser Tyr Thr Cys Glu Ala Thr His Lys Thr Ser
        210                 215                 220

Thr Ser Pro Ile Val Lys Ser Phe Asn Arg Asn Glu Ser
225                 230                 235

<210> SEQ ID NO 16
<211> LENGTH: 246
<212> TYPE: PRT
<213> ORGANISM: Artificial Sequence
<220> FEATURE:
<223> OTHER INFORMATION: Synthetic protein

<400> SEQUENCE: 16

Met Lys Gln Ser Thr Ile Ala Leu Ala Leu Leu Pro Leu Leu Phe Thr
1               5                   10                  15

Pro Val Ala Lys Ala Gln Ala Tyr Leu Gln Gln Ser Gly Pro Glu Leu
            20                  25                  30

Val Lys Ala Gly Ala Ser Val Lys Met Ser Cys Lys Ala Ser Gly Tyr
        35                  40                  45

Ser Phe Ile Glu Tyr Thr Ile Asn Trp Val Lys Gln Ser His Gly Lys
50                  55                  60

Ser Leu Glu Trp Ile Gly Asn Ile Asp Pro Tyr Tyr Gly Thr Thr Tyr
65                  70                  75                  80

Tyr Asn Gln Met Phe Thr Gly Lys Ala Thr Leu Thr Val Asp Gln Ser
            85                  90                  95

Ser Asn Thr Ala Tyr Met Gln Leu Lys Ser Leu Thr Ser Glu Asp Ser
        100                 105                 110

Ala Val Tyr Phe Cys Ala Arg Gly Ser Ala Trp Phe Pro Tyr Trp Gly
    115                 120                 125

Gln Gly Thr Leu Val Thr Val Ser Ala Ala Lys Thr Thr Pro Pro Ser
130                 135                 140

Val Tyr Pro Leu Ala Pro Gly Ser Ala Ala Gln Thr Asn Ser Met Val
145                 150                 155                 160

Thr Leu Gly Cys Leu Val Lys Gly Tyr Phe Pro Glu Pro Val Thr Val
            165                 170                 175

Thr Trp Asn Ser Gly Ser Leu Ser Ser Gly Val His Thr Phe Pro Ala
        180                 185                 190

Val Leu Gln Ser Asp Leu Tyr Thr Leu Ser Ser Ser Val Thr Val Pro
    195                 200                 205

Ser Ser Thr Trp Pro Ser Glu Thr Val Thr Cys Asn Val Ala His Pro
210                 215                 220

Ala Ser Ser Thr Lys Val Asp Lys Lys Ile Val Pro Arg Asp Cys His
225                 230                 235                 240

His His His His His His
                245

<210> SEQ ID NO 17
<211> LENGTH: 235
<212> TYPE: PRT
<213> ORGANISM: Artificial Sequence
<220> FEATURE:
<223> OTHER INFORMATION: Synthetic protein

<400> SEQUENCE: 17

Met Lys Tyr Leu Leu Pro Thr Ala Ala Gly Leu Leu Leu Leu Ala
1               5                   10                  15

Ala Gln Pro Ala Met Ala Asp Ile Val Met Ser Gln Ser Pro Ala Ile
                20                  25                  30

Met Ser Ala Ser Pro Gly Glu Lys Val Thr Met Thr Cys Ser Ala Ser
                35                  40                  45

Ser Ser Val Thr Tyr Met Tyr Trp Tyr Gln Gln Lys Pro Gly Ser Ser
            50                  55                  60

Pro Arg Leu Leu Ile Tyr Asp Thr Ser Asn Leu Ala Ser Gly Val Pro
65                  70                  75                  80

Val Arg Phe Ser Gly Ser Gly Ser Gly Thr Ser Tyr Ser Leu Thr Ile
                85                  90                  95

Ser Arg Met Glu Ala Glu Asp Thr Ala Thr Tyr Tyr Cys Gln Gln Trp
            100                 105                 110

Ser Asn Tyr Pro Leu Thr Phe Gly Ala Gly Thr Lys Leu Glu Leu Lys
        115                 120                 125

Arg Ala Asp Ala Ala Pro Thr Val Ser Ile Phe Pro Pro Ser Ser Glu
130                 135                 140

Gln Leu Thr Ser Gly Gly Ala Ser Val Val Cys Phe Leu Asn Asn Phe
145                 150                 155                 160

Tyr Pro Lys Asp Ile Asn Val Lys Trp Lys Ile Asp Gly Ser Glu Arg
                165                 170                 175

Gln Asn Gly Val Leu Asn Ser Trp Thr Asp Gln Asp Ser Lys Asp Ser
            180                 185                 190

Thr Tyr Ser Met Ser Ser Thr Leu Thr Leu Thr Lys Asp Glu Tyr Glu
        195                 200                 205

Arg His Asn Ser Tyr Thr Cys Glu Ala Thr His Lys Thr Ser Thr Ser
    210                 215                 220

Pro Ile Val Lys Ser Phe Asn Arg Asn Glu Ser
225                 230                 235

<210> SEQ ID NO 18
<211> LENGTH: 811
<212> TYPE: PRT
<213> ORGANISM: Artificial Sequence
<220> FEATURE:
<223> OTHER INFORMATION: Synthetic protein

<400> SEQUENCE: 18

Ala Cys Gly Cys Thr Thr Thr Gly Thr Ala Cys Ala Thr Gly Gly Ala
1               5                   10                  15

Gly Ala Ala Ala Ala Thr Ala Ala Ala Gly Thr Gly Ala Ala Ala Cys
                20                  25                  30

Ala Ala Ala Gly Cys Ala Cys Thr Ala Thr Thr Gly Cys Ala Cys Thr
                35                  40                  45

Gly Gly Cys Ala Cys Thr Cys Thr Thr Ala Cys Cys Gly Cys Thr Cys
            50                  55                  60

-continued

```
Thr Thr Ala Thr Thr Thr Ala Cys Cys Cys Cys Thr Gly Thr Gly Gly
 65                  70                  75                  80

Cys Ala Ala Ala Ala Gly Cys Cys Cys Ala Gly Gly Thr Gly Ala Ala
                 85                  90                  95

Gly Cys Thr Thr Cys Ala Gly Cys Ala Gly Thr Cys Cys Gly Gly Gly
            100                 105                 110

Gly Cys Thr Gly Ala Gly Cys Thr Gly Gly Thr Gly Ala Gly Gly Cys
            115                 120                 125

Cys Thr Gly Gly Gly Thr Cys Cys Thr Cys Ala Gly Thr Gly Ala Ala
        130                 135                 140

Gly Ala Thr Thr Thr Cys Cys Thr Gly Cys Ala Ala Gly Gly Cys Thr
145                 150                 155                 160

Thr Cys Thr Gly Gly Cys Thr Ala Cys Gly Cys Ala Thr Thr Cys Ala
                165                 170                 175

Gly Thr Ala Ala Cys Thr Cys Cys Thr Gly Ala Thr Ala Ala Ala
                180                 185                 190

Cys Thr Gly Gly Gly Thr Gly Ala Ala Gly Cys Ala Gly Ala Gly Gly
            195                 200                 205

Cys Cys Thr Gly Gly Ala Cys Ala Gly Gly Thr Cys Thr Thr Gly
            210                 215                 220

Ala Gly Thr Gly Gly Ala Thr Thr Gly Gly Ala Cys Ala Gly Ala Thr
225                 230                 235                 240

Thr Thr Ala Thr Cys Cys Thr Gly Gly Ala Gly Ala Thr Thr Ala Thr
                245                 250                 255

Gly Ala Thr Ala Cys Thr Ala Ala Cys Thr Ala Cys Ala Ala Thr Gly
            260                 265                 270

Gly Ala Ala Ala Ala Thr Thr Cys Ala Ala Gly Gly Thr Ala Ala
            275                 280                 285

Ala Gly Cys Cys Ala Cys Ala Cys Thr Gly Ala Cys Thr Gly Cys Ala
        290                 295                 300

Gly Ala Cys Thr Ala Cys Thr Cys Cys Thr Cys Ala Gly Cys Ala
305                 310                 315                 320

Cys Ala Gly Cys Cys Thr Ala Cys Ala Thr Gly Cys Ala Gly Cys Thr
                325                 330                 335

Cys Ala Ala Cys Ala Gly Cys Cys Thr Ala Ala Cys Ala Thr Cys Thr
            340                 345                 350

Gly Ala Gly Gly Ala Cys Thr Cys Thr Gly Cys Gly Gly Thr Cys Thr
            355                 360                 365

Ala Thr Thr Thr Cys Thr Gly Thr Gly Cys Ala Ala Gly Gly Gly
        370                 375                 380

Gly Gly Gly Ala Thr Cys Gly Ala Thr Cys Thr Ala Cys Thr Ala Thr
385                 390                 395                 400

Gly Gly Thr Ala Ala Cys Cys Thr Cys Gly Gly Thr Thr Cys Thr
                405                 410                 415

Thr Cys Gly Ala Thr Gly Thr Cys Thr Gly Gly Gly Gly Cys Gly Cys
            420                 425                 430

Ala Gly Gly Gly Ala Cys Cys Ala Cys Gly Gly Thr Cys Ala Cys Cys
            435                 440                 445

Gly Thr Cys Thr Cys Cys Thr Cys Ala Gly Cys Cys Ala Ala Ala Ala
        450                 455                 460

Cys Gly Ala Cys Ala Cys Cys Cys Cys Cys Ala Thr Cys Thr Gly Thr
465                 470                 475                 480
```

Cys Thr Ala Thr Cys Cys Ala Cys Thr Gly Cys Cys Cys Thr
              485                 490                 495

Gly Gly Ala Thr Cys Thr Gly Cys Thr Gly Cys Cys Ala Ala Ala
          500                 505                 510

Cys Thr Ala Ala Cys Thr Cys Cys Ala Thr Gly Gly Thr Gly Ala Cys
          515                 520                 525

Cys Cys Thr Gly Gly Ala Thr Gly Cys Cys Thr Gly Gly Thr Cys
      530                 535                 540

Ala Ala Gly Gly Gly Cys Thr Ala Thr Thr Cys Cys Cys Thr Gly
545                 550                 555                 560

Ala Gly Cys Cys Ala Gly Thr Gly Ala Cys Ala Gly Thr Gly Ala Cys
              565                 570                 575

Cys Thr Gly Gly Ala Ala Cys Thr Cys Thr Gly Gly Ala Thr Cys Cys
              580                 585                 590

Cys Thr Gly Thr Cys Cys Ala Gly Cys Gly Gly Thr Gly Thr Gly Cys
              595                 600                 605

Ala Cys Ala Cys Thr Thr Cys Cys Cys Ala Gly Cys Thr Gly Thr
      610                 615                 620

Cys Cys Thr Gly Cys Ala Gly Thr Cys Thr Gly Ala Cys Cys Thr Cys
625                 630                 635                 640

Thr Ala Cys Ala Cys Thr Cys Thr Gly Ala Gly Cys Ala Gly Cys Thr
              645                 650                 655

Cys Ala Gly Thr Gly Ala Cys Thr Gly Thr Cys Cys Cys Cys Thr Cys
              660                 665                 670

Cys Ala Gly Cys Ala Cys Cys Thr Gly Gly Cys Cys Cys Ala Gly Cys
              675                 680                 685

Gly Ala Gly Ala Cys Cys Gly Thr Cys Ala Cys Cys Thr Gly Cys Ala
      690                 695                 700

Ala Cys Gly Thr Thr Gly Cys Cys Cys Ala Cys Cys Cys Gly Gly Cys
705                 710                 715                 720

Cys Ala Gly Cys Ala Gly Cys Ala Cys Cys Ala Ala Gly Gly Thr Gly
              725                 730                 735

Gly Ala Cys Ala Ala Gly Ala Ala Ala Thr Thr Gly Thr Gly Cys
          740                 745                 750

Cys Cys Ala Gly Gly Gly Ala Thr Thr Gly Thr Cys Ala Thr Cys Ala
              755                 760                 765

Thr Cys Ala Cys Cys Ala Thr Cys Ala Cys Cys Ala Thr Cys Ala Cys
          770                 775                 780

Thr Ala Ala Thr Thr Gly Ala Cys Ala Gly Cys Thr Thr Ala Thr Cys
785                 790                 795                 800

Ala Thr Cys Gly Ala Thr Ala Asn Gly Cys Thr
              805                 810

<210> SEQ ID NO 19
<211> LENGTH: 759
<212> TYPE: PRT
<213> ORGANISM: Artificial Sequence
<220> FEATURE:
<223> OTHER INFORMATION: Synthetic protein

<400> SEQUENCE: 19

Gly Thr Thr Thr Thr Thr Thr Gly Gly Ala Thr Gly Gly Ala Gly
1               5                   10                  15

Thr Gly Ala Ala Ala Cys Gly Ala Thr Gly Ala Ala Thr Ala Cys
              20                  25                  30

-continued

```
Cys Thr Ala Thr Thr Gly Cys Cys Thr Ala Cys Gly Gly Cys Ala Gly
        35                  40                  45

Cys Cys Gly Cys Thr Gly Gly Ala Thr Thr Gly Thr Thr Ala Thr Thr
    50                  55                  60

Ala Cys Thr Cys Gly Cys Thr Gly Cys Cys Cys Ala Ala Cys Cys Ala
65                  70                  75                  80

Gly Cys Cys Ala Thr Gly Gly Cys Cys Gly Ala Ala Ala Thr Gly Gly
                85                  90                  95

Thr Thr Cys Thr Cys Ala Cys Cys Cys Ala Gly Thr Cys Thr Cys Cys
            100                 105                 110

Ala Gly Cys Ala Ala Thr Cys Ala Thr Gly Thr Cys Thr Ala Cys Ala
        115                 120                 125

Thr Cys Thr Cys Thr Ala Gly Gly Gly Gly Ala Ala Cys Gly Gly Gly
    130                 135                 140

Thr Cys Ala Cys Cys Ala Thr Gly Ala Cys Cys Thr Gly Cys Ala Cys
145                 150                 155                 160

Thr Gly Cys Cys Ala Gly Cys Thr Cys Ala Cys Gly Thr Gly Thr Ala
                165                 170                 175

Ala Gly Thr Thr Cys Cys Ala Gly Thr Thr Ala Cys Thr Thr Gly Cys
            180                 185                 190

Ala Cys Thr Gly Gly Thr Ala Cys Cys Ala Gly Cys Ala Gly Ala Ala
        195                 200                 205

Gly Cys Cys Ala Gly Gly Ala Thr Cys Cys Thr Cys Cys Cys Cys Cys
    210                 215                 220

Ala Ala Ala Cys Thr Cys Thr Gly Gly Ala Thr Thr Thr Ala Thr Ala
225                 230                 235                 240

Gly Thr Ala Cys Ala Thr Cys Cys Ala Ala Cys Cys Thr Gly Gly Cys
                245                 250                 255

Thr Thr Cys Thr Gly Gly Ala Gly Thr Cys Cys Cys Ala Gly Cys Thr
            260                 265                 270

Cys Gly Cys Thr Thr Cys Ala Gly Thr Gly Gly Cys Ala Gly Thr Gly
        275                 280                 285

Gly Gly Thr Cys Thr Gly Gly Gly Ala Cys Cys Thr Cys Thr Thr Ala
    290                 295                 300

Cys Thr Cys Thr Cys Thr Cys Ala Cys Ala Ala Thr Cys Ala Gly Cys
305                 310                 315                 320

Ala Gly Cys Ala Thr Gly Gly Ala Gly Gly Cys Thr Gly Ala Ala Gly
                325                 330                 335

Ala Thr Gly Cys Thr Gly Cys Cys Ala Cys Thr Thr Ala Thr Thr Ala
            340                 345                 350

Cys Thr Gly Cys Cys Ala Cys Cys Ala Gly Thr Ala Thr Cys Ala Thr
        355                 360                 365

Cys Gly Thr Thr Cys Cys Cys Cys Gly Thr Ala Cys Ala Cys Gly Thr
    370                 375                 380

Thr Cys Gly Gly Ala Gly Gly Gly Gly Gly Gly Ala Cys Cys Ala Ala
385                 390                 395                 400

Gly Cys Thr Gly Gly Ala Ala Ala Thr Ala Ala Ala Ala Cys Gly Gly
                405                 410                 415

Gly Cys Thr Gly Ala Thr Gly Cys Thr Gly Cys Ala Cys Cys Ala Ala
            420                 425                 430

Cys Thr Gly Thr Ala Thr Cys Cys Ala Thr Cys Thr Thr Cys Cys Cys
        435                 440                 445

Ala Cys Cys Ala Thr Cys Cys Ala Gly Thr Gly Ala Gly Cys Ala Gly
```

```
    450                 455                 460

Thr Thr Ala Ala Cys Ala Thr Cys Thr Gly Gly Ala Gly Gly Thr Gly
465                 470                 475                 480

Cys Cys Thr Cys Ala Gly Thr Cys Gly Thr Gly Thr Gly Cys Thr Thr
                485                 490                 495

Cys Thr Thr Gly Ala Ala Cys Ala Ala Cys Thr Thr Cys Thr Ala Cys
            500                 505                 510

Cys Cys Cys Ala Ala Ala Gly Ala Cys Ala Thr Cys Ala Ala Thr Gly
        515                 520                 525

Thr Cys Ala Ala Gly Thr Gly Gly Ala Ala Gly Ala Thr Thr Gly Ala
    530                 535                 540

Thr Gly Gly Cys Ala Gly Thr Gly Ala Ala Cys Gly Ala Cys Ala Ala
545                 550                 555                 560

Ala Ala Thr Gly Gly Cys Gly Thr Cys Cys Thr Gly Ala Ala Cys Ala
                565                 570                 575

Gly Thr Thr Gly Gly Ala Cys Thr Gly Ala Thr Cys Ala Gly Gly Ala
            580                 585                 590

Cys Ala Gly Cys Ala Ala Ala Gly Ala Cys Ala Gly Cys Ala Cys Cys
        595                 600                 605

Thr Ala Cys Ala Gly Cys Ala Thr Gly Ala Gly Cys Ala Gly Cys Ala
    610                 615                 620

Cys Cys Cys Thr Cys Ala Cys Gly Thr Thr Gly Ala Cys Cys Ala Ala
625                 630                 635                 640

Gly Gly Ala Cys Gly Ala Gly Thr Ala Thr Gly Ala Ala Cys Gly Ala
                645                 650                 655

Cys Ala Thr Ala Ala Cys Ala Gly Cys Thr Ala Thr Ala Cys Cys Thr
            660                 665                 670

Gly Thr Gly Ala Gly Gly Cys Cys Ala Cys Thr Cys Ala Cys Ala Ala
        675                 680                 685

Gly Ala Cys Ala Thr Cys Ala Ala Cys Thr Thr Cys Ala Cys Cys Cys
    690                 695                 700

Ala Thr Thr Gly Thr Cys Ala Ala Gly Ala Gly Cys Thr Thr Cys Ala
705                 710                 715                 720

Ala Cys Ala Gly Gly Ala Ala Thr Gly Ala Gly Thr Cys Thr Thr Ala
                725                 730                 735

Ala Gly Thr Gly Ala Thr Thr Ala Gly Cys Thr Ala Ala Thr Thr Cys
            740                 745                 750

Thr Ala Gly Ala Ala Cys Gly
        755
```

<210> SEQ ID NO 20
<211> LENGTH: 803
<212> TYPE: PRT
<213> ORGANISM: Artificial Sequence
<220> FEATURE:
<223> OTHER INFORMATION: Synthetic protein

<400> SEQUENCE: 20

```
Ala Ala Ala Ala Cys Cys Cys Thr Gly Gly Cys Gly Thr Thr Ala Cys
1               5                   10                  15

Cys Cys Ala Cys Gly Cys Thr Thr Thr Gly Thr Ala Cys Ala Thr Gly
            20                  25                  30

Gly Ala Gly Ala Ala Ala Ala Thr Ala Ala Ala Gly Thr Gly Ala Ala
        35                  40                  45

Ala Cys Ala Ala Ala Gly Cys Ala Cys Thr Ala Thr Thr Gly Cys Ala
```

-continued

```
    50                  55                  60

Cys Thr Gly Gly Cys Ala Cys Thr Cys Thr Thr Ala Cys Cys Gly Cys
65                  70                  75                  80

Thr Cys Thr Thr Ala Thr Thr Thr Ala Cys Cys Cys Cys Thr Gly Thr
                85                  90                  95

Gly Gly Cys Ala Ala Ala Ala Gly Cys Cys Cys Ala Gly Gly Cys Thr
            100                 105                 110

Thr Ala Thr Cys Thr Ala Cys Ala Gly Cys Ala Gly Thr Cys Thr Gly
        115                 120                 125

Gly Ala Cys Cys Thr Gly Ala Gly Cys Thr Gly Gly Thr Gly Ala Ala
    130                 135                 140

Gly Gly Cys Thr Gly Gly Cys Gly Cys Thr Thr Cys Ala Gly Thr Gly
145                 150                 155                 160

Ala Ala Gly Ala Thr Gly Thr Cys Cys Thr Gly Cys Ala Ala Gly Gly
                165                 170                 175

Cys Thr Thr Cys Thr Gly Gly Thr Thr Ala Cys Thr Cys Ala Thr Thr
            180                 185                 190

Cys Ala Thr Thr Gly Ala Gly Thr Ala Cys Ala Cys Cys Ala Thr Ala
        195                 200                 205

Ala Ala Cys Thr Gly Gly Gly Thr Gly Ala Ala Ala Cys Ala Gly Ala
    210                 215                 220

Gly Cys Cys Ala Thr Gly Gly Ala Ala Ala Gly Ala Gly Cys Cys Thr
225                 230                 235                 240

Thr Gly Ala Gly Thr Gly Gly Ala Thr Thr Gly Gly Ala Ala Ala Thr
                245                 250                 255

Ala Thr Thr Gly Ala Thr Cys Cys Thr Thr Ala Thr Thr Ala Thr Gly
            260                 265                 270

Gly Ala Ala Cys Cys Ala Cys Thr Thr Ala Thr Thr Ala Cys Ala Ala
        275                 280                 285

Thr Cys Ala Gly Ala Thr Gly Thr Thr Cys Ala Cys Gly Gly Gly Cys
    290                 295                 300

Ala Ala Gly Gly Cys Cys Ala Cys Ala Thr Thr Gly Ala Cys Thr Gly
305                 310                 315                 320

Thr Ala Gly Ala Cys Cys Ala Ala Thr Cys Thr Thr Cys Cys Ala Ala
                325                 330                 335

Cys Ala Cys Thr Gly Cys Cys Thr Ala Cys Ala Thr Gly Cys Ala Gly
            340                 345                 350

Cys Thr Cys Ala Ala Gly Ala Gly Cys Cys Thr Gly Ala Cys Ala Thr
        355                 360                 365

Cys Thr Gly Ala Gly Gly Ala Cys Thr Cys Thr Gly Cys Ala Gly Thr
    370                 375                 380

Cys Thr Ala Thr Thr Thr Cys Thr Gly Thr Gly Cys Ala Ala Gly Ala
385                 390                 395                 400

Gly Gly Cys Thr Cys Cys Gly Cys Cys Thr Gly Gly Thr Thr Thr Cys
                405                 410                 415

Cys Thr Thr Ala Cys Thr Gly Gly Gly Cys Cys Ala Gly Gly Gly
            420                 425                 430

Gly Ala Cys Thr Cys Thr Ala Gly Thr Cys Ala Cys Thr Gly Thr Cys
        435                 440                 445

Thr Cys Thr Gly Cys Ala Gly Cys Cys Ala Ala Ala Ala Cys Gly Ala
    450                 455                 460

Cys Ala Cys Cys Cys Cys Cys Ala Thr Cys Thr Gly Thr Cys Thr Ala
465                 470                 475                 480
```

```
Thr Cys Cys Ala Cys Thr Gly Gly Cys Cys Cys Cys Thr Gly Gly Ala
                485                 490                 495

Thr Cys Thr Gly Cys Thr Gly Cys Cys Cys Ala Ala Ala Cys Thr Ala
            500                 505                 510

Ala Cys Thr Cys Cys Ala Thr Gly Gly Thr Gly Ala Cys Cys Cys Thr
        515                 520                 525

Gly Gly Gly Ala Thr Gly Cys Cys Thr Gly Gly Thr Cys Ala Ala Gly
    530                 535                 540

Gly Gly Cys Thr Ala Thr Thr Thr Cys Cys Cys Thr Gly Ala Gly Cys
545                 550                 555                 560

Cys Ala Gly Thr Gly Ala Cys Ala Gly Thr Gly Ala Cys Cys Thr Gly
                565                 570                 575

Gly Ala Ala Cys Thr Cys Thr Gly Gly Ala Thr Cys Cys Cys Thr Gly
            580                 585                 590

Thr Cys Cys Ala Gly Cys Gly Gly Thr Gly Thr Gly Cys Ala Cys Ala
        595                 600                 605

Cys Cys Thr Thr Cys Cys Cys Ala Gly Cys Thr Gly Thr Cys Cys Thr
    610                 615                 620

Gly Cys Ala Gly Thr Cys Thr Gly Ala Cys Cys Thr Cys Thr Ala Cys
625                 630                 635                 640

Ala Cys Thr Cys Thr Gly Ala Gly Cys Ala Gly Cys Thr Cys Ala Gly
                645                 650                 655

Thr Gly Ala Cys Thr Gly Thr Cys Cys Cys Cys Thr Cys Cys Ala Gly
            660                 665                 670

Cys Ala Cys Cys Thr Gly Gly Cys Cys Cys Ala Gly Cys Gly Ala Gly
        675                 680                 685

Ala Cys Cys Gly Thr Cys Ala Cys Cys Thr Gly Cys Ala Ala Cys Gly
    690                 695                 700

Thr Thr Gly Cys Cys Cys Ala Cys Cys Cys Gly Gly Cys Cys Ala Gly
705                 710                 715                 720

Cys Ala Gly Cys Ala Cys Cys Ala Ala Gly Gly Thr Gly Gly Ala Cys
                725                 730                 735

Ala Ala Gly Ala Ala Ala Ala Thr Thr Gly Thr Gly Cys Cys Cys Ala
            740                 745                 750

Gly Gly Gly Ala Thr Thr Gly Thr Cys Ala Thr Cys Ala Thr Cys Ala
        755                 760                 765

Cys Cys Ala Thr Cys Ala Cys Cys Ala Thr Cys Ala Cys Thr Ala Ala
    770                 775                 780

Thr Thr Gly Ala Cys Ala Gly Cys Thr Thr Ala Thr Cys Ala Thr Cys
785                 790                 795                 800

Gly Ala Thr
```

<210> SEQ ID NO 21
<211> LENGTH: 804
<212> TYPE: PRT
<213> ORGANISM: Artificial Sequence
<220> FEATURE:
<223> OTHER INFORMATION: Synthetic protein

<400> SEQUENCE: 21

```
Ala Cys Thr Cys Thr Cys Thr Ala Cys Thr Gly Thr Thr Thr Cys Thr
1               5                   10                  15

Cys Cys Ala Thr Ala Cys Cys Cys Gly Thr Thr Thr Thr Thr Thr Thr
            20                  25                  30
```

-continued

```
Gly Gly Ala Thr Gly Gly Ala Gly Thr Gly Ala Ala Ala Cys Gly Ala
        35                  40                  45

Thr Gly Ala Ala Ala Thr Ala Cys Cys Thr Ala Thr Thr Gly Cys Cys
    50                  55                  60

Thr Ala Cys Gly Gly Cys Ala Gly Cys Cys Gly Cys Thr Gly Gly Ala
65                  70                  75                  80

Thr Thr Gly Thr Thr Ala Thr Thr Ala Cys Thr Cys Gly Cys Thr Gly
                85                  90                  95

Cys Cys Cys Ala Ala Cys Cys Ala Gly Cys Cys Ala Thr Gly Gly Cys
            100                 105                 110

Cys Gly Ala Cys Ala Thr Cys Gly Thr Thr Ala Thr Gly Thr Cys Thr
        115                 120                 125

Cys Ala Gly Thr Cys Thr Cys Cys Ala Gly Cys Ala Ala Thr Cys Ala
    130                 135                 140

Thr Gly Thr Cys Thr Gly Cys Ala Thr Cys Thr Cys Cys Ala Gly Gly
145                 150                 155                 160

Gly Gly Ala Gly Ala Ala Gly Gly Thr Cys Ala Cys Cys Ala Thr Gly
                165                 170                 175

Ala Cys Cys Thr Gly Cys Ala Gly Thr Gly Cys Cys Ala Gly Cys Thr
            180                 185                 190

Cys Ala Ala Gly Thr Gly Thr Ala Ala Cys Thr Thr Ala Cys Ala Thr
        195                 200                 205

Gly Thr Ala Cys Thr Gly Gly Thr Ala Cys Cys Ala Gly Cys Ala Gly
    210                 215                 220

Ala Ala Gly Cys Cys Ala Gly Gly Ala Thr Cys Cys Thr Cys Cys Cys
225                 230                 235                 240

Cys Cys Ala Gly Ala Cys Thr Cys Cys Thr Gly Ala Thr Thr Thr Ala
                245                 250                 255

Thr Gly Ala Cys Ala Cys Ala Thr Cys Cys Ala Ala Cys Cys Thr Gly
            260                 265                 270

Gly Cys Thr Thr Cys Thr Gly Gly Ala Gly Thr Cys Cys Cys Thr Gly
        275                 280                 285

Thr Thr Cys Gly Cys Thr Thr Cys Ala Gly Thr Gly Gly Cys Ala Gly
    290                 295                 300

Thr Gly Gly Gly Thr Cys Thr Gly Gly Gly Ala Cys Cys Thr Cys Thr
305                 310                 315                 320

Thr Ala Cys Thr Cys Thr Cys Thr Cys Ala Cys Ala Ala Thr Cys Ala
                325                 330                 335

Gly Cys Cys Gly Ala Ala Thr Gly Gly Ala Gly Gly Cys Thr Gly Ala
            340                 345                 350

Ala Gly Ala Thr Ala Cys Thr Gly Cys Cys Ala Cys Thr Thr Ala Thr
        355                 360                 365

Thr Ala Cys Thr Gly Cys Cys Ala Gly Cys Ala Gly Thr Gly Gly Ala
    370                 375                 380

Gly Thr Ala Ala Thr Thr Ala Cys Cys Cys Ala Cys Thr Cys Ala Cys
385                 390                 395                 400

Gly Thr Thr Cys Gly Gly Thr Gly Cys Thr Gly Gly Gly Ala Cys Cys
                405                 410                 415

Ala Ala Gly Cys Thr Gly Gly Ala Gly Cys Thr Gly Ala Ala Ala Cys
            420                 425                 430

Gly Gly Gly Cys Thr Gly Ala Thr Gly Cys Thr Gly Cys Ala Cys Cys
        435                 440                 445

Ala Ala Cys Thr Gly Thr Ala Thr Cys Cys Ala Thr Cys Thr Thr Cys
```

-continued

```
    450                 455                 460

Cys Cys Ala Cys Cys Ala Thr Cys Cys Ala Gly Thr Gly Ala Gly Cys
465                 470                 475                 480

Ala Gly Thr Thr Ala Ala Cys Ala Thr Cys Thr Gly Gly Ala Gly Gly
                485                 490                 495

Thr Gly Cys Cys Thr Cys Ala Gly Thr Cys Gly Thr Gly Thr Gly Cys
            500                 505                 510

Thr Thr Cys Thr Thr Gly Ala Ala Cys Ala Ala Cys Thr Thr Cys Thr
        515                 520                 525

Ala Cys Cys Cys Cys Ala Ala Ala Gly Ala Cys Ala Thr Cys Ala Ala
    530                 535                 540

Thr Gly Thr Cys Ala Ala Gly Thr Gly Gly Ala Ala Gly Ala Thr Thr
545                 550                 555                 560

Gly Ala Thr Gly Gly Cys Ala Gly Thr Gly Ala Ala Cys Gly Ala Cys
                565                 570                 575

Ala Ala Ala Ala Thr Gly Gly Cys Gly Thr Cys Cys Thr Gly Ala Ala
            580                 585                 590

Cys Ala Gly Thr Thr Gly Gly Ala Cys Thr Gly Ala Thr Cys Ala Gly
        595                 600                 605

Gly Ala Cys Ala Gly Cys Ala Ala Ala Gly Ala Cys Ala Gly Cys Ala
    610                 615                 620

Cys Cys Thr Ala Cys Ala Gly Cys Ala Thr Gly Ala Gly Cys Ala Gly
625                 630                 635                 640

Cys Ala Cys Cys Cys Thr Cys Ala Cys Gly Thr Thr Gly Ala Cys Cys
                645                 650                 655

Ala Ala Gly Gly Ala Cys Gly Ala Gly Thr Ala Thr Gly Ala Ala Cys
            660                 665                 670

Gly Ala Cys Ala Thr Ala Ala Cys Ala Gly Cys Thr Ala Thr Ala Cys
        675                 680                 685

Cys Thr Gly Thr Gly Ala Gly Gly Cys Cys Ala Cys Thr Cys Ala Cys
    690                 695                 700

Ala Ala Gly Ala Cys Ala Thr Cys Ala Ala Cys Thr Thr Cys Ala Cys
705                 710                 715                 720

Cys Cys Ala Thr Thr Gly Thr Cys Ala Ala Gly Ala Gly Cys Thr Thr
                725                 730                 735

Cys Ala Ala Cys Ala Gly Gly Ala Ala Thr Gly Ala Gly Thr Cys Thr
            740                 745                 750

Thr Ala Ala Gly Thr Gly Ala Thr Thr Ala Gly Cys Thr Ala Ala Thr
        755                 760                 765

Thr Cys Thr Ala Gly Ala Ala Cys Gly Cys Gly Thr Cys Ala Cys Thr
    770                 775                 780

Thr Gly Gly Cys Ala Cys Thr Gly Gly Cys Cys Gly Thr Cys Gly Thr
785                 790                 795                 800

Thr Thr Thr Ala
```

THERAPEUTIC AND DIAGNOSTIC TARGET

RELATED APPLICATIONS

This application is a 35 U.S.C. 371 national stage filing of International Application No. PCT/IB2012/001680, filed on Jun. 28, 2012, which claims priority to U.S. Provisional Application No. 61/502,160, filed on Jun. 28, 2011. The contents of the aforementioned applications are hereby incorporated by reference.

INTRODUCTION

The present invention relates to the identification of membrane protein associated with acute myeloid leukemia (AML), B-cell chronic lymphocytic leukemia, breast cancer, colorectal cancer, kidney cancer, head and neck cancer, lung cancer, ovarian cancer and pancreatic cancer which has utility as therapeutic target for the treatment of cancer or as a marker for such cancers. In particular the protein represents a biological target against which affinity reagents including therapeutic antibodies, or other pharmaceutical agents can be made. The invention also relates to the use of such affinity reagents for the treatment or diagnosis of cancer such as acute myeloid leukemia (AML), B-cell chronic lymphocytic leukemia, breast cancer, colorectal cancer, kidney cancer, head and neck cancer, lung cancer, ovarian cancer or pancreatic cancer. The invention also relates to depletion of immune cell expression of the protein using e.g. monoclonal antibodies to treat inflammatory diseases.

BACKGROUND OF THE INVENTION

The major challenges in treatment of acute myeloid leukemia (AML), B-cell chronic lymphocytic leukemia, breast cancer, colorectal cancer, kidney cancer, head and neck cancer, lung cancer, ovarian cancer and pancreatic cancer are to improve early detection rates, to find new non-invasive markers that can be used to follow disease progression and identify relapse, and to find improved and less toxic therapies, especially for more advanced disease where 5 year survival is still poor. There is a great need to identify targets which are more specific to the cancer cells, e.g. ones which are expressed on the surface of the tumour cells so that they can be attacked by promising new approaches like immunotherapeutics and targeted toxins.

The inventor has shown BST1 to be expressed on monocytes and granulocytes, both of which can be associated with and activated in diseases such as asthma, gout, crohns, lupus and diabetes. Monocytes are also implicated in the development of atherosclerotic plaques. BST1 has not been previously reported to originate from acute myeloid leukemia (AML), B-cell chronic lymphocytic leukemia, breast cancer, colorectal cancer, kidney cancer, head and neck cancer, lung cancer, ovarian cancer or pancreatic cancer cell membranes and represents a protein of new therapeutic and diagnostic value.

SUMMARY OF THE INVENTION

The present invention discloses the detection of ADP-ribosyl cyclase 2, hereinafter referred to as BST1, in membrane extracts of various disease tissues, e.g. acute myeloid leukemia (AML), B-cell chronic lymphocytic leukemia, breast cancer, colorectal cancer, kidney cancer, head and neck cancer, lung cancer, ovarian cancer, pancreatic cancer, asthma, gout, crohns, lupus, multiple sclerosis, rheumatoid arthritis, psoriasis, diabetes and atherosclerotic, hereinafter referred to as 'the diseases of the invention', but not in membrane extracts of normal tissues.

The differential expression of BST1 in various cancers permits the protein to be targeted as the basis for affinity reagent, e.g. antibody, based therapies for such cancers. Thus cancer-associated BST1 can be used in the generation of affinity reagents, including antibodies, that bind specifically to BST1 and can be targeted by such affinity reagents as the basis of treatment. Affinity reagents, including antibodies, that target a protein on the cell surface of cancer cells may be employed in the treatment of cancer through a variety of mechanisms, including (i) lysis by complement mediated or antibody-dependent cellular cytotoxicity (ADCC), (ii) lysis by drugs or toxin(s) conjugated to such antibodies or (iii) inhibition of the physiological function of such protein, which may be driving growth of cancer cells, e.g. through signaling pathways. An important aspect of such antibody-based treatment is that the normal expression profile of the protein target, in terms of tissue distribution and expression level, is such that any targeting of the protein target on normal tissues by the antibody does not give rise to adverse side-effects through binding to normal tissues.

The full length human variant of BST1 is shown in SEQ ID NO: 1.

The present invention demonstrates the association of BST1 with various cancers and the generation of antibodies specific to BST1. Such antibodies have been used to verify the expression profile of BST1 through immunohistochemistry and flow cytometry analysis, which reveals the presence, through specific binding, of BST1 on the cell surface of various cancer tissues and the absence of BST1 in normal tissues. Furthermore, such antibodies have been demonstrated to fulfill the requirements of cytolytic anti-cancer agents through their cell surface binding to cancer cell lines, internalization upon binding to cancer cell lines, live cell binding to ex-vivo malignant cells and, crucially, their ability to kill cancer cells through internalization of a toxin.

The invention provides a method for the treatment or prophylaxis of cancer wherein the BST1 is expressed in said cancer, which comprises administering to a subject in need thereof a therapeutically effective amount of an affinity reagent which binds to BST1.

The cancer is preferably one of the diseases of the invention.

The invention also provides an affinity reagent which binds to BST1 for use in the treatment or prophylaxis of a cancer as described above.

The invention also provides the use of an affinity reagent which binds to BST1 in the manufacture of a medicament for the treatment or prophylaxis of a cancer as described above.

The affinity reagents for use in the invention preferably bind specifically to BST1.

The affinity reagent may be an antibody, e.g. a whole antibody, or a functional fragment thereof or an antibody mimetic. Preferred affinity reagents included antibodies for example monoclonal antibodies.

The affinity reagent may be a chimeric antibody, a human antibody, a humanized antibody, a single chain antibody, a defucosylated antibody or a bispecific antibody.

Functional antibody fragments include is a UniBody, a domain antibody or a Nanobody.

Antibody mimetics include an Affibody, a DARPin, an Anticalin, an Avimer, a Versabody or a Duocalin.

The affinity reagents for use in the invention may contain or be conjugated to a therapeutic moiety, such as a cytotoxic moiety or a radioactive isotope. The affinity reagent may be an antibody drug conjugate or immunoconjugate.

In the methods of the invention the affinity reagent may elicit antibody-dependent cellular cytotoxicity (ADCC) or may elicit complement dependent cytotoxicity (CDC). The affinity reagent may induce apoptosis of tumor cells, kill or reduce the number of cancer stem cells and/or kill or reduce the number of circulating tumor cells. Affinity reagents may modulate the physiological function of BST1, inhibits ligand binding and/or inhibits signal transduction pathways.

In an alternative embodiment the invention also provides a method for the treatment or prophylaxis of cancer wherein BST1 is expressed in said cancer, which comprises administering to a subject in need thereof a therapeutically effective amount of a hybridizing agent capable of hybridizing to nucleic acid encoding BST1.

The cancer is preferably one of the diseases of the invention.

The invention also provides a hybridizing agent capable of hybridizing to nucleic acid encoding BST1 for use in the treatment or prophylaxis of a cancer as described above.

The invention also provides the use of a hybridizing agent capable of hybridizing to nucleic acid encoding BST1 in the manufacture of a medicament for the treatment or prophylaxis of a cancer as described above.

The hybridizing agents for use in the invention preferably bind specifically to nucleic acid encoding BST1.

Suitable hybridizing agent for use in the invention include inhibitory RNA, short interfering RNA (siRNA), a short hairpin RNA (shRNA), a microRNA (miRNA), and antisense nucleic acid or a complementary DNA (cDNA), oligonucleotodes and ribozymes.

The invention also provides a method of detecting, diagnosing and/or screening for or monitoring the progression cancer wherein BST1 is expressed in said cancer, or of monitoring the effect of a cancer drug or therapy wherein BST1 is expressed in said cancer, in a subject which comprises detecting the presence or level of BST1, or one or more fragments thereof, or the presence or level of nucleic acid encoding BST1 or which comprises detecting a change in the level thereof in said subject.

Such a method may comprise detecting the presence of BST1, or one or more fragments thereof, or the presence of nucleic acid encoding BST1, in which either (a) the presence of an elevated level of BST1 or said one or more fragments thereof or an elevated level of nucleic acid encoding BST1 in the subject as compared with the level in a healthy subject, or (b) the presence of a detectable level of BST1 or said one or more fragments thereof or a detectable level of nucleic acid BST1 in the subject as compared with a corresponding undetectable level in a healthy subject is indicative of the presence of cancer wherein BST1 is expressed in said cancer, in said subject.

The invention also provides a method of detecting, diagnosing and/or screening for or monitoring the progression cancer wherein BST1 is expressed in said cancer, or of monitoring the effect of a cancer drug or therapy wherein BST1 is expressed in said cancer, in a subject which comprises detecting the presence or level of antibodies capable of immunospecific binding to BST1, or one or more fragments thereof.

In such methods the cancer is preferably one of the diseases of the invention.

In the diagnostic methods according to the invention the presence of BST1, or one or more fragments thereof, or the presence of nucleic acid encoding BST1, or the presence or level of antibodies capable of immunospecific binding to BST1, or one or more fragments thereof, is detected by analysis of a biological sample obtained from the subject.

The presence of BST1, or one or more fragments thereof, may be detected using an affinity reagent which binds to BST1. The affinity reagent may be any suitable affinity reagent as mentioned above. The affinity reagent may contain or be conjugated to a detectable label.

In any of the aspects of the invention referred to above the subject may be a human.

The invention also provides a method for identifying an agent for the treatment or prophylaxis of cancer wherein BST1 is expressed in said cancer, wherein the method comprises (a) contacting BST1, or one or more fragments thereof, with a candidate agent; and (b) determining whether the agent binds to BST1, or one or more fragments thereof. The method may also further comprise the step of testing the ability of an agent which binds to BST1, or one or more fragments thereof, to inhibit cancer wherein BST1 is expressed in said cancer.

The agents identifies using the method according to this aspect of the invention are preferably for the treatment or prophylaxis of the diseases of the invention.

The agents identified using such methods may be small molecules and may modulate the activity of BST1, reduce ligand binding to BST1.

In the various embodiments of the invention described herein particular cancer types and/or inflammatory diseases which may be mentioned are one of the diseases of the invention.

In one embodiment the cancer to be detected, prevented or treated is acute myeloid leukemia (AML).

In another embodiment the cancer to be detected, prevented or treated is breast cancer.

In another embodiment the cancer to be detected, prevented or treated is colorectal cancer.

In another embodiment the cancer to be detected, prevented or treated is kidney cancer.

In another embodiment the cancer to be detected, prevented or treated is head and neck cancer.

In another embodiment the cancer to be detected, prevented or treated is lung cancer, e.g. non-small cell lung cancer and/or small cell lung cancer.

In another embodiment the cancer to be detected, prevented or treated is ovarian cancer.

In another embodiment the cancer to be detected, prevented or treated is pancreatic cancer.

In one embodiment the inflammatory diseases to be detected, prevented or treated is asthma.

In another embodiment the inflammatory diseases to be detected, prevented or treated is gout.

In another embodiment the inflammatory diseases to be detected, prevented or treated is crohns disease.

In another embodiment the inflammatory diseases to be detected, prevented or treated is lupus.

In another embodiment the inflammatory diseases to be detected, prevented or treated is multiple sclerosis.

In another embodiment the inflammatory diseases to be detected, prevented or treated is rheumatoid arthritis.

In another embodiment the inflammatory diseases to be detected, prevented or treated is psoriasis.

In another embodiment the inflammatory diseases to be detected, prevented or treated is diabetes.

In another embodiment the inflammatory diseases to be detected, prevented or treated is atherosclerotic.

Other aspects of the present invention are set out below and in the claims herein.

BRIEF DESCRIPTION OF THE FIGURES

FIGS. 1a, 1b, 1c, 1d, 1e, 1f and 1g show the amino acid sequence of the protein of the invention. The tandem peptides detected experimentally by LCMS are underlined.

FIG. 2 show the amino acid sequence of the protein of the invention. The tandem peptides detected experimentally by iTRAQ in non-small cell lung cancer are underlined.

FIGS. 3a and 3b show the results of RNA profiling analysis of BST1.

DETAILED DESCRIPTION OF THE INVENTION

Figure 3B:
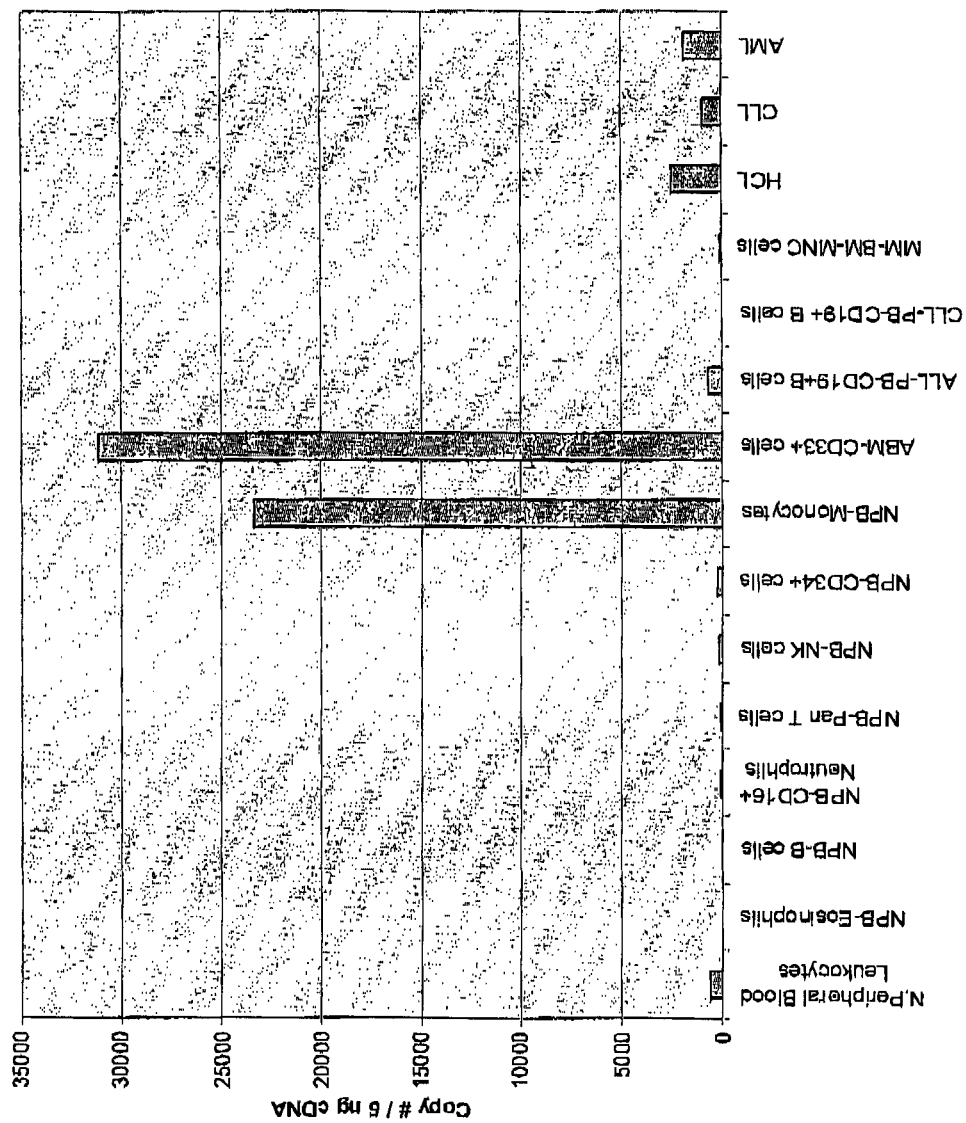

The present invention provides methods and compositions for screening, diagnosis, prognosis and therapy of the diseases of the invention patients' stratification, for monitoring the effectiveness of the diseases of the invention treatment, and for drug development for treatment of the diseases of the invention.

The invention described in detail below encompasses the administration of therapeutic compositions to a subject, e.g. a mammalian subject, to treat or prevent cancer e.g. the diseases of the invention. The invention also provides methods and compositions for clinical screening, diagnosis and prognosis of cancer e.g. the diseases of the invention in a mammalian subject for identifying patients most likely to respond to a particular therapeutic treatment, for monitoring the results of cancer e.g. the diseases of the invention therapy, for drug screening and drug development.

In one aspect the invention provides an agent capable of specific binding to BST1, or a fragment thereof, or a hybridising agent capable of hybridizing to nucleic acid encoding BST1 or an agent capable of detecting the activity of BST1 for use in treating, screening for, detecting and/or diagnosing disease, such as cancer, and especially the diseases of the invention.

Another aspect of the invention is an affinity reagent capable of specific binding to BST1 or a fragment thereof, for example an affinity reagent which contains or is conjugated to a detectable label or contains or is conjugated to a therapeutic moiety such as a cytotoxic moiety. The affinity reagent may, for example, be an antibody.

The affinity reagents for use in the invention may bind to an epitope of BST1 which comprises one or more of the portions of SEQ ID NO: 13.

Another aspect of the invention is a pharmaceutical composition comprising a therapeutically effective amount of an affinity reagent capable of specific binding to BST1 or a fragment thereof.

In another aspect the invention provides use of a BST1 polypeptide, or one or more fragments or derivatives thereof, for the treatment or prophylaxis of e.g. the diseases of the invention.

The invention also provides use of a BST1 polypeptide, one or more fragments or derivatives thereof in the manufacture of a medicament for the treatment or prophylaxis of e.g. the diseases of the invention.

In one aspect there is provided a method of treatment comprising admininstering a therapeutically effective amount of a BST1 polypeptide, one or more fragments or derivatives thereof, or one or more fragments or derivatives thereof, for the treatment or prophylaxis of e.g. the diseases of the invention.

The invention further provides a method for the treatment or prophylaxis of e.g. the diseases of the invention in a subject, or of vaccinating a subject against e.g. the diseases of the invention, which comprises the step of administering to the subject an effective amount of a BST1 polypeptide and/or one or more antigenic or immunogenic fragments thereof, for example as a vaccine.

The mammalian subject may be a non-human mammal, but is generally human, such as a human adult, i.e. a human subject at least 21 (for example at least 35, at least 50, at least 60, at least 70, or at least 80) years old.

In one aspect there is provided a composition capable of eliciting an immune response in a subject, which composition comprises a BST1 polypeptide and/or one or more antigenic or immunogenic fragments thereof, and one or more suitable adjuvants (suitable adjuvants are discussed below).

The composition capable of eliciting an immune response may for example be provided as a vaccine comprising a BST1 polypeptide or derivatives thereof, and/or one or more antigenic or immunogenic fragments thereof.

For clarity of disclosure, and not by way of limitation, the invention will be described with respect to the analysis of myeloid, breast, colorectal, kidney, lung or pancreatic tissue. However, as one skilled in the art will appreciate, the assays and techniques described below can be applied to other types of patient samples, including body fluids (e.g. blood, urine or saliva), a tissue sample from a patient at risk of having the diseases of the invention (e.g. a biopsy such as a myeloid, breast, colorectal, kidney, lung or pancreatic biopsy) or homogenate thereof. The methods and compositions of the present invention are specially suited for screening, diagnosis and prognosis of a living subject, but may also be used for postmortem diagnosis in a subject, for example, to identify family members at risk of developing the same disease.

In some embodiments, the present invention is a method for preparing an anti-BST1 antibody, said method comprising the steps of: obtaining a host cell that contains one or more nucleic acid molecules encoding the antibody of the invention; growing the host cell in a host cell culture; providing host cell culture conditions wherein the one or more nucleic acid molecules are expressed; and recovering the antibody from the host cell or from the host cell culture.

Other aspects of the invention are directed to methods of making the antibodies of the invention, comprising the steps of: immunizing a transgenic animal comprising human immunoglobulin genes with a BST1 peptide; recovering B-cells from said transgenic animal; making hybridomas from said B-cells; selecting hybridomas that express antibodies that bind BST1; and recovering said antibodies that bind BST1 from said selected hybridomas.

In other embodiments, the method of making anti-BST1 antibodies, comprises the steps of:

(a) immunizing a transgenic animal comprising human immunoglobulin genes with a BST1 peptide;

(b) recovering mRNA from the B cells of said transgenic animal;

(c) converting said mRNA to cDNA;

(d) expressing said cDNA in phages such that anti-BST1 antibodies encoded by said cDNA are presented on the surface of said phages;

(e) selecting phages that present anti-BST1 antibodies;

(f) recovering nucleic acid molecules from said selected phages that encode said anti-BST1 immunoglobulins;

(g) expressing said recovered nucleic acid molecules in a host cell; and (h) recovering antibodies from said host cell that bind BST1.

Another aspect of the invention provides use of a BST1 polypeptide, one or more immunogenic fragments or derivatives thereof for the treatment or prophylaxis of e.g. the diseases of the invention.

In another aspect, the invention provides methods of treating e.g. the diseases of the invention, comprising administering to a patient a therapeutically effective amount of a compound that modulates (e.g., upregulates or down-regulates) or complements the expression or the biological activity (or both) of the protein of the invention in patients having e.g. the diseases of the invention, in order to (a) prevent the onset or development of e.g. the diseases of the invention; (b) prevent the progression of e.g. the diseases of the invention; or (c) ameliorate the symptoms of e.g. the diseases of the invention.

According to another aspect of the invention we provide a method of detecting, diagnosing and/or screening for or monitoring the progression of e.g. the diseases of the invention or of monitoring the effect of e.g. an anti-cancer drug or therapy directed towards the diseases of the invention in a subject which comprises detecting the presence or level of BST1, or one or more fragments thereof, or the presence or level of nucleic acid encoding BST1 or the presence or level of the activity of BST1 or which comprises detecting a change in the level thereof in said subject.

According to another aspect of the invention we provide a method of detecting, diagnosing and/or screening for e.g. the diseases of the invention in a candidate subject which comprises detecting the presence of BST1, or one or more fragments thereof, or the presence of nucleic acid encoding BST1 or the presence of the activity of BST1 in said candidate subject, in which either (a) the presence of an elevated level of BST1 or said one or more fragments thereof or an elevated level of nucleic acid encoding BST1 or the presence of an elevated level of BST1 activity in the candidate subject as compared with the level in a healthy subject or (b) the presence of a detectable level of BST1 or said one or more fragments thereof or a detectable level of nucleic acid encoding BST1 or the presence of a detectable level of BST1 activity in the candidate subject as compared with a corresponding undetectable level in a healthy subject indicates the presence of e.g. the diseases of the invention in said subject.

According to another aspect of the invention we provide a method of monitoring the progression of e.g. the diseases of the invention in a subject or of monitoring the effect of e.g. an anti-cancer drug or therapy directed towards the diseases of the invention which comprises detecting the presence of BST1, or one or more fragments thereof, or the presence of nucleic acid encoding BST1 or the presence of the activity of BST1 in said candidate subject at a first time point and at a later time point, the presence of an elevated or lowered level of BST1 or said one or more fragments thereof or an elevated or lowered level of nucleic acid encoding BST1 or the presence of an elevated or lowered level of BST1 activity in the subject at the later time point as compared with the level in the subject at said first time point, indicating the progression or regression of e.g. the diseases of the invention or indicating the effect or non-effect of e.g. anti-cancer drug or therapy directed towards the diseases of the invention in said subject.

According to another aspect of the invention there is provided a method of detecting, diagnosing and/or screening for or monitoring the progression of cancer e.g. the diseases of the invention or of monitoring the effect of an anti-cancer drug or therapy directed towards the diseases of the invention in a subject which comprises detecting the presence or level of antibodies capable of immunospecific binding to BST1, or one or more epitope-containing fragments thereof or which comprises detecting a change in the level thereof in said subject.

According to another aspect of the invention there is also provided a method of detecting, diagnosing and/or screening for cancer e.g. the diseases of the invention in a subject which comprises detecting the presence of antibodies capable of immunospecific binding to BST1, or one or more epitope-containing fragments thereof in said subject, in which (a) the presence of an elevated level of antibodies capable of immunospecific binding to BST1 or said one or more epitope-containing fragments thereof in said subject as compared with the level in a healthy subject or (b) the presence of a detectable level of antibodies capable of immunospecific binding to BST1 or said one or more epitope-containing fragments thereof in said subject as compared with a corresponding undetectable level in a healthy subject indicates the presence of said cancer in said subject.

One particular method of detecting, diagnosing and/or screening for cancer, e.g. the diseases of the invention comprises:

bringing into contact with a biological sample to be tested BST1, or one or more epitope-containing fragments thereof; and detecting the presence of antibodies in the subject capable of immunospecific binding to BST1, or one or more epitope-containing fragments thereof.

According to another aspect of the invention there is provided a method of monitoring the progression of cancer, e.g. the diseases of the invention or of monitoring the effect of an anti-cancer drug or therapy directed towards the diseases of the invention in a subject which comprises detecting the presence of antibodies capable of immunospecific binding to BST1, or one or more epitope-containing fragments thereof in said subject at a first time point and at a later time point, the presence of an elevated or lowered level of antibodies capable of immunospecific binding to BST1, or one or more epitope-containing fragments thereof in said subject at the later time point as compared with the level in said subject at said first time point, indicating the progression or regression of said cancer, or the effect or non-effect of said anti-cancer drug or therapy in said subject.

The presence of antibodies capable of immunospecific binding to BST1, or one or more epitope-containing fragments thereof is typically detected by analysis of a biological sample obtained from said subject (exemplary biological samples are mentioned above, e.g. the sample is a sample of myeloid, breast, colorectal, kidney, lung or pancreatic tissue, or else a sample of blood or saliva). The method typically includes the step of obtaining said biological sample for analysis from said subject.

The antibodies that may be detected include IgA, IgM and IgG antibodies.

In any of the above methods, the level that may be detected in the candidate subject who has cancer, e.g. the diseases of the invention is 2 or more fold higher than the level in the healthy subject.

In one aspect of the invention, one-dimensional electrophoresis or other appropriate methods are used to analyze myeloid, breast, colorectal, kidney, lung or pancreatic tissue samples from a subject, preferably a living subject, in order to measure the expression of the protein of the invention for screening or diagnosis of e.g. the diseases of the invention, to determine the prognosis of a patient with any of the diseases of the invention, to monitor the effectiveness of diseases of the invention therapy, or for drug development.

As used herein, the term "Protein of the invention", or "BST1", refers to the protein illustrated in FIG. 1 detected experimentally by liquid chromatography-mass spectrometry of cancer tissue samples and FIG. 2 detected experimentally by Isotope Tagging for Absolute & Relative Quantitation. Protein derivatives of this sequence may also be useful for the same purposes as described herein.

This protein has been identified in membrane protein extracts of cancer tissue samples from cancer patients, through the methods and apparatus of the Preferred Technology described in Examples 1 and 2 (e.g. by liquid chromatography-mass spectrometry and Isotope Tagging for Absolute & Relative Quantitation tryptic digest of membrane protein extracts). Peptide sequences were compared to the SWISS-PROT and trEMBL databases (held by the Swiss Institute of Bioinformatics (SIB) and the European Bioinformatics Institute (EBI) which are available at ExPAS Bioinformatics Resource Portal), and the following entry: Q10588, ADP-ribosyl cyclase 2 was identified. The nucleotide sequence encoding this protein is found at accession number NM_004334.2, which is expressly incorporated herein by reference.

ADP-ribosyl cyclase 2 (also known as Bone marrow stromal antigen 1 (BST1) or CD157) is a lipid-anchored, bi-functional ectoenzyme that catalyses ribonucleotide cyclisation and hydrolysis. It generates the nucleotide second messengers cyclic ADP-ribose and ADP-ribose that are capable of activating calcium release and protein phosphorylation (FEBS Lett. 1994, 356(2-3):244-8). It is able to support growth of pre-B cells in a paracrine fashion, possibly through generation of NAD+ metabolites (Proc. Natl. Acad. Sci. USA 1994, 91:5325-5329; J Biol. Chem. 2005, 280:5343-5349).

Immunohistochemistry experiments (see Example 3) showed strong staining in non-small cell lung cancer.

RNA profiling and flow cytometry experiments were also conducted and showed that BST1 is expressed at high levels in circulating cancer cells of patients with acute myeloid leukaemia (AML). At these levels, an antibody with enhanced ADCC engineering would be therapeutically effective.

BST1 has been shown to internalize by MabZAP assay (see Example 9), illustrating an antibody-drug conjugate (ADC), would be therapeutically effective.

The protein of the invention is useful as are fragments particularly epitope containing fragments e.g. antigenic or immunogenic fragments thereof and derivatives thereof. Epitope containing fragments including antigenic or immunogenic fragments will typically be of length 12 amino acids or more e.g. 20 amino acids or more e.g. 50 or 100 amino acids or more. Fragments may be 95% or more of the length of the full protein e.g. 90% or more e.g. 75% or 50% or 25% or 10% or more of the length of the full protein.

Alternatively, the protein/polypeptide employed or referred to herein may be limited to those specifically recited/described in the present specification or a moiety 80, 85, 90, 91, 92, 93, 94, 95, 96, 97, 98 or 99% identical or similar thereto.

Epitope containing fragments including antigenic or immunogenic fragments will be capable of eliciting a relevant immune response in a patient. DNA encoding the protein of the invention is also useful as are fragments thereof e.g. DNA encoding fragments of the protein of the invention such as immunogenic fragments thereof. Fragments of nucleic acid (e.g. DNA) encoding the protein of the invention may be 95% or more of the length of the full coding region e.g. 90% or more e.g. 75% or 50% or 25% or 10% or more of the length of the full coding region. Fragments of nucleic acid (e.g. DNA) may be 36 nucleotides or more e.g. 60 nucleotides or more e.g. 150 or 300 nucleotides or more in length.

Derivatives of the protein of the invention include variants on the sequence in which one or more (e.g. 1-20 such as 15 amino acids, or up to 20% such as up to 10% or 5% or 1% by number of amino acids based on the total length of the protein) deletions, insertions or substitutions have been made. Substitutions may typically be conservative substitutions. Derivatives will typically have essentially the same biological function as the protein from which they are derived. Derivatives will typically be comparably antigenic or immunogenic to the protein from which they are derived. Derivatives will typically have either the ligand-binding activity, or the active receptor-complex forming ability, or preferably both, of the protein from which they are derived.

Derivatives of proteins also include chemically treated protein such as carboxymethylated, carboxyamidated, acetylated proteins, for example treated during purification.

For BST1, the detected level obtained upon analyzing tissue from subjects having e.g. the diseases of the invention relative to the detected level obtained upon analyzing tissue from subjects free from e.g. the diseases of the invention will depend upon the particular analytical protocol and detection technique that is used. Accordingly, the present invention contemplates that each laboratory will establish a reference range in subjects free from e.g. the diseases of the invention according to the analytical protocol and detection technique in use, as is conventional in the diagnostic art. Preferably, at least one control positive tissue sample from a subject known to have e.g. the diseases of the invention or at least one control negative tissue sample from a subject known to be free from e.g. the diseases of the invention (and more preferably both positive and negative control samples) are included in each batch of test samples analysed.

BST1 can be used for detection, prognosis, diagnosis, or monitoring of e.g. the diseases of the invention or for drug development. In one embodiment of the invention, tissue from a subject (e.g. a subject suspected of having the diseases of the invention) is analysed by liquid chromatography-mass spectrometry for detection of BST1. An increased abundance of BST1 in the tissue from the subject relative to tissue from a subject or subjects free from the diseases of the invention (e.g. a control sample) or a previously determined reference range indicates the presence of the diseases of the invention.

In another embodiment of the invention, tissue from a subject (e.g. a subject suspected of having the diseases of the invention) is analysed by Isotope Tagging for Absolute & Relative Quantitation for detection of BST1. An increased abundance of BST1 in the tissue from the subject relative to tissue from a subject or subjects free from the diseases of the invention (e.g. a control sample) or a previously determined reference range indicates the presence of the diseases of the invention.

In relation to fragments, epitope containing fragments, immunogenic fragments or antigenic fragments of BST1: for the relevant cancer applications, in one aspect of the invention these comprise the sequences identified as tryptic sequences in Examples 1 and 2.

As used herein, BST1 is "isolated" when it is present in a preparation that is substantially free of contaminating proteins, i.e. a preparation in which less than 10% (for example less than 5%, such as less than 1%) of the total protein present is contaminating protein(s). A contaminating protein is a protein having a significantly different amino acid sequence from that of isolated BST1, as determined by mass spectral analysis. As used herein, a "significantly different" sequence is one that permits the contaminating protein to be resolved from BST1 by mass spectral analysis, performed according to the Reference Protocol described herein in Example 1 and 2.

Thus in one aspect the invention provides a pharmaceutical composition for the treatment of e.g. the diseases of the invention comprising a therapeutically effective amount of a BST1 polypeptide (particularly those defined above) or an immunogenic fragment thereof and an adjuvant.

BST1 can be assayed by any method known to those skilled in the art, including but not limited to, the Preferred Technologies described herein, kinase assays, enzyme assays, binding assays and other functional assays, immunoassays, and western blotting.

Alternatively, BST1 can be detected in an immunoassay. In one embodiment, an immunoassay is performed by contacting a sample from a subject to be tested with an anti-BST1 antibody (or other affinity reagent) under conditions such that binding (e.g. immunospecific binding) can occur if BST1 is present, and detecting or measuring the amount of any binding (e.g. immunospecific binding) by the agent. BST1 binding agents can be produced by the methods and techniques taught herein. In a particular embodiment, BST1 is analysed using immunohistochemistry.

BST1 may be detected by virtue of the detection of a fragment thereof e.g. an epitope containing (e.g. an immunogenic or antigenic) fragment thereof. Fragments may have a length of at least 10, more typically at least 20 amino acids e.g. at least 50 or 100 amino acids e.g. at least 150 or 200 amino acids; e.g. at least 300 or 500 amino acids; e.g. at least 700 or 900 amino acids.

In one embodiment, binding of an affinity reagent (e.g. an antibody) in tissue sections can be used to detect aberrant BST1 localization or an aberrant level of BST1. In a specific embodiment, an antibody (or other affinity reagent) to BST1 can be used to assay a patient tissue (e.g. a myeloid, breast, colorectal, kidney, lung or pancreatic tissue) for the level of BST1 where an aberrant level of BST1 is indicative of the diseases of the invention. As used herein, an "aberrant level" means a level that is increased compared with the level in a subject free from the diseases of the invention or a reference level.

Any suitable immunoassay can be used, including, without limitation, competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays and protein A immunoassays.

For example, BST1 can be detected in a fluid sample (e.g. blood, urine, or saliva) by means of a two-step sandwich assay. In the first step, a capture reagent (e.g. an anti-BST1 antibody or other affinity reagent) is used to capture BST1. The capture reagent can optionally be immobilized on a solid phase. In the second step, a directly or indirectly labeled detection reagent is used to detect the captured BST1. In one embodiment, the detection reagent is a lectin. Any lectin can be used for this purpose that preferentially binds to BST1 rather than to other isoforms that have the same core protein as BST1 or to other proteins that share the antigenic determinant recognized by the antibody. In a preferred embodiment, the chosen lectin binds BST1 with at least 2-fold greater affinity, more preferably at least 5-fold greater affinity, still more preferably at least 10-fold greater affinity, than to said other isoforms that have the same core protein as BST1 or to said other proteins that share the antigenic determinant recognized by the affinity reagent. Based on the present description, a lectin that is suitable for detecting BST1 can readily be identified by methods well known in the art, for instance upon testing one or more lectins enumerated in Table I on pages 158-159 of Sumar et al., Lectins as Indicators of Disease-Associated Glycoforms, In: Gabius H-J & Gabius S (eds.), 1993, Lectins and Glycobiology, at pp. 158-174 (which is incorporated herein by reference in its entirety). In an alternative embodiment, the detection reagent is an antibody (or other affinity reagent), e.g. an antibody that specifically (e.g. immunospecifically) detects other post-translational modifications, such as an antibody that immunospecifically binds to phosphorylated amino acids. Examples of such antibodies include those that bind to phosphotyrosine (BD Transduction Laboratories, catalog nos.: P11230-050/P11230-150; P11120; P38820; P39020), those that bind to phosphoserine (Zymed Laboratories Inc., South San Francisco, Calif., catalog no. 61-8100) and those that bind to phosphothreonine (Zymed Laboratories Inc., South San Francisco, Calif., catalogue nos. 71-8200, 13-9200).

If desired, a gene encoding BST1, a related gene, or related nucleic acid sequences or subsequences, including complementary sequences, can also be used in hybridization assays. A nucleotide encoding BST1, or subsequences thereof comprising at least 8 nucleotides, preferably at least 12 nucleotides, and most preferably at least 15 nucleotides can be used as a hybridization probe. Hybridization assays can be used for detection, prognosis, diagnosis, or monitoring of conditions, disorders, or disease states, associated with aberrant expression of the gene encoding BST1, or for differential diagnosis of subjects with signs or symptoms suggestive of e.g. the diseases of the invention. In particular, such a hybridization assay can be carried out by a method comprising contacting a subject's sample containing nucleic acid with a nucleic acid probe capable of hybridizing to a DNA or RNA that encodes BST1, under conditions such that hybridization can occur, and detecting or measuring any resulting hybridization.

Hence nucleic acid encoding BST1 (e.g. DNA or more suitably RNA) may be detected, for example, using a hybridizing agent capable of hybridizing to nucleic acid encoding BST1.

One such exemplary method comprises:
contacting one or more oligonucleotide probes comprising 10 or more consecutive nucleotides complementary to a nucleotide sequence encoding BST1, with an RNA obtained from a biological sample from the subject or with cDNA copied from the RNA, wherein said contacting occurs under conditions that permit hybridization of the probe to the nucleotide sequence if present;

detecting hybridization, if any, between the probe and the nucleotide sequence; and comparing the hybridization, if any, detected in step (b) with the hybridization detected in a control sample, or with a previously determined reference range.

The invention also provides diagnostic kits, comprising an anti-BST1 antibody (or other affinity reagent). In addition, such a kit may optionally comprise one or more of the following: (1) instructions for using the anti-BST1 affinity reagent for diagnosis, prognosis, therapeutic monitoring or any combination of these applications; (2) a labeled binding partner to the affinity reagent; (3) a solid phase (such as a reagent strip) upon which the anti-BST1 affinity reagent is immobilized; and (4) a label or insert indicating regulatory approval for diagnostic, prognostic or therapeutic use or any combination thereof. If no labeled binding partner to the affinity reagent is provided, the anti-BST1 affinity reagent itself can be labeled with a detectable marker, e.g. a chemiluminescent, enzymatic, fluorescent, or radioactive moiety.

The invention also provides a kit comprising a nucleic acid probe capable of hybridizing to nucleic acid, suitably RNA, encoding BST1. In a specific embodiment, a kit comprises one or more containers a pair of primers (e.g. each in the size range of 6-30 nucleotides, more preferably 10-30 nucleotides and still more preferably 10-20 nucleotides) that under appropriate reaction conditions can prime amplification of at least a portion of a nucleic acid encoding BST1, such as by polymerase chain reaction (see, e.g. Innis et al., 1990, PCR Protocols, Academic Press, Inc., San Diego, Calif.), ligase chain reaction (see EP 320,308) use of Qβ replicase, cyclic probe reaction, or other methods known in the art.

A kit can optionally further comprise a predetermined amount of BST1 or a nucleic acid encoding BST1, e.g. for use as a standard or control.

The biological sample used can be from any source such as a serum sample or a tissue sample e.g. myeloid, breast, colorectal, kidney, lung or pancreatic tissue. For instance, when looking for evidence of metastatic the diseases of the invention, one would look at major sites of the diseases of the invention metastasis, e.g. the liver, lungs and bones for breast cancer; the liver, peritoneal cavity, pelvis, retroperitoneum and lungs for colorectal cancer; the bones, lungs and liver for kidney cancer; the brain, liver, bones and adrenal glands for lung cancer and the liver for pancreatic cancer.

Alternatively the presence of BST1, or one or more fragments thereof, or the presence of nucleic acid encoding BST1 or the presence of the activity of BST1 may be detected by analysis in situ.

In certain embodiments, methods of diagnosis described herein may be at least partly, or wholly, performed in vitro.

Suitably the presence of BST1, or one or more fragments thereof, or the presence of nucleic acid encoding BST1 or the presence of the activity of BST1 is detected quantitatively.

For example, quantitatively detecting may comprise:

contacting a biological sample with an affinity reagent that is specific for BST1, said affinity reagent optionally being conjugated to a detectable label; and detecting whether binding has occurred between the affinity reagent and at least one species in the sample, said detection being performed either directly or indirectly.

Alternatively the presence of BST1, or one or more fragments thereof, or the presence of nucleic acid encoding BST1 or the presence of the activity of BST1 may be detected quantitatively by means involving use of an imaging technology.

In another embodiment, the method of the invention involves use of immunohistochemistry on e.g. myeloid, breast, colorectal, kidney, lung or pancreatic tissue sections in order to determine the presence of BST1, or one or more fragments thereof, or the presence of nucleic acid encoding BST1 or the presence of the activity of BST1, and thereby to localise e.g. the diseases of the invention cells.

In one embodiment the presence of BST1 or one or more epitope-containing fragments thereof is detected, for example using an affinity reagent capable of specific binding to BST1 or one or more fragments thereof, such as an antibody.

In another embodiment the activity of BST1 is detected. ADP-ribosyl cyclase 2 and its homolog, CD38, appear to act as receptors, generating second messenger metabolites that induce intracellular Ca2+ release via the ryanodine receptor (Biochem Biophys Res Commun 1996, 228(3):838-45). It may also act via CD11b integrin to effect Ca2+ release through the PI-3 Kinase pathway (J Biol Regul Homeost Agents. 2007; 21(1-2):5-11).

Use in Clinical Studies

The diagnostic methods and compositions of the present invention can assist in monitoring a clinical study, e.g. to evaluate drugs for therapy of the diseases of the invention. In one embodiment, candidate molecules are tested for their ability to restore BST1 levels in a subject having e.g. the diseases of the invention to levels found in subjects free from the diseases of the invention or, in a treated subject, to preserve BST1 levels at or near non-acute myeloid leukemia, non-breast cancer, non-colorectal cancer, non-kidney cancer, non-lung cancer or non-pancreatic cancer values.

In another embodiment, the methods and compositions of the present invention are used to screen candidates for a clinical study to identify individuals having e.g. the diseases of the invention; such individuals can then be excluded from the study or can be placed in a separate cohort for treatment or analysis.

Production of Protein of the Invention and Corresponding Nucleic Acid

In one aspect the invention provides a method of treating or preventing e.g. the disease of the invention, comprising administering to a subject in need of such treatment or prevention a therapeutically effective amount of nucleic acid encoding BST1 or one or more fragments or derivatives thereof, for example in the form of a vaccine.

In another aspect there is provided a method of treating or preventing e.g. the diseases of the invention comprising administering to a subject in need of such treatment or prevention a therapeutically effective amount of nucleic acid that inhibits the function or expression of BST1.

The methods (and/or other DNA aspects disclosed herein) of the invention may, for example include wherein the nucleic acid is a BST1 anti-sense nucleic acid or ribozyme.

Thus the invention includes the use of nucleic acid encoding BST1 or one or more fragments or derivatives thereof, in the manufacture of a medicament for treating or preventing e.g. the diseases of the invention.

There is also provided the use of nucleic acid that inhibits the function or expression of BST1 in the manufacture of a medicament for treating or preventing e.g. the diseases of the invention.

A DNA employed in the present invention can be obtained by isolation as a cDNA fragment from cDNA libraries using as starter materials commercial mRNAs and determining and identifying the nucleotide sequences thereof. That is, specifically, clones are randomly isolated from cDNA libraries, which are prepared according to Ohara et al.'s method (*DNA Research* Vol. 4, 53-59 (1997)). Next, through hybridization, duplicated clones (which appear repeatedly) are removed and then in vitro transcription and translation are carried out. Nucleotide sequences of both termini of clones, for which products of 50 kDa or more are confirmed, are determined.

Furthermore, databases of known genes are searched for homology using the thus obtained terminal nucleotide sequences as queries.

In addition to the above screening method, the 5' and 3' terminal sequences of cDNA are related to a human genome sequence. Then an unknown long-chain gene is confirmed in a region between the sequences, and the full-length of the cDNA is analyzed. In this way, an unknown gene that is unable to be obtained by a conventional cloning method that depends on known genes can be systematically cloned.

Moreover, all of the regions of a human-derived gene containing a DNA of the present invention can also be prepared using a PCR method such as RACE while paying sufficient attention to prevent artificial errors from taking place in short fragments or obtained sequences. As described above, clones having DNA of the present invention can be obtained.

In another means for cloning DNA of the present invention, a synthetic DNA primer having an appropriate nucleotide sequence of a portion of a polypeptide of the present invention is produced, followed by amplification by the PCR method using an appropriate library. Alternatively, selection can be carried out by hybridization of the DNA of the present invention with a DNA that has been incorporated into an appropriate vector and labeled with a DNA fragment or a synthetic DNA encoding some or all of the regions of the polypeptide of the present invention. Hybridization can be carried out by, for example, the method described in Current Protocols in Molecular Biology (edited by Frederick M. Ausubel et al., 1987). DNA of the present invention may be any DNA, as long as they contain nucleotide sequences encoding the polypeptides of the present invention as described above. Such a DNA may be a cDNA identified and isolated from cDNA libraries or the like that are derived from myeloid, breast, colorectal, kidney, lung or pancreatic tissue. Such a DNA may also be a synthetic DNA or the like. Vectors for use in library construction may be any of bacteriophages, plasmids, cosmids, phargemids, or the like. Furthermore, by the use of a total RNA fraction or a mRNA fraction prepared from the above cells and/or tissues, amplification can be carried out by a direct reverse transcription coupled polymerase chain reaction (hereinafter abbreviated as "RT-PCR method").

DNA encoding the above polypeptide consisting of an amino acid sequence that is substantially identical to the amino acid sequence of BST1 or DNA encoding the above polypeptide consisting of an amino acid sequence derived from the amino acid sequence of BST1 by deletion, substitution, or addition of one or more amino acids composing a portion of the amino acid sequence can be easily produced by an appropriate combination of, for example, a site-directed mutagenesis method, a gene homologous recombination method, a primer elongation method, and the PCR method known by persons skilled in the art. In addition, at this time, a possible method for causing a polypeptide to have substantially equivalent biological activity is substitution of homologous amino acids (e.g. polar and nonpolar amino acids, hydrophobic and hydrophilic amino acids, positively-charged and negatively charged amino acids, and aromatic amino acids) among amino acids composing the polypeptide. Furthermore, to maintain substantially equivalent biological activity, amino acids within functional domains contained in the polypeptide of the present invention are preferably conserved.

Furthermore, examples of DNA of the present invention include DNA comprising a nucleotide sequence that encodes the amino acid sequence of BST1 and DNA hybridizing under stringent conditions to the DNA and encoding a polypeptide (protein) having biological activity (function) equivalent to the function of the polypeptide consisting of the amino acid sequence of BST1. Under such conditions, an example of such DNA capable of hybridizing to DNA comprising the nucleotide sequence that encodes the amino acid sequence of BST1 is DNA comprising a nucleotide sequence that has a degree of overall mean homology with the entire nucleotide sequence of the DNA, such as approximately 80% or more, preferably approximately 90% or more, and more preferably approximately 95% or more. Hybridization can be carried out according to a method known in the art such as a method described in Current Protocols in Molecular Biology (edited by Frederick M. Ausubel et al., 1987) or a method according thereto. Here, "stringent conditions" are, for example, conditions of approximately "1*SSC, 0.1% SDS, and 37° C., more stringent conditions of approximately "0.5*SSC, 0.1% SDS, and 42° C., or even more stringent conditions of approximately "0.2*SSC, 0.1% SDS, and 65° C. With more stringent hybridization conditions, the isolation of a DNA having high homology with a probe sequence can be expected. The above combinations of SSC, SDS, and temperature conditions are given for illustrative purposes. Stringency similar to the above can be achieved by persons skilled in the art using an appropriate combination of the above factors or other factors (for example, probe concentration, probe length, and reaction time for hybridization) for determination of hybridization stringency.

A cloned DNA of the present invention can be directly used or used, if desired, after digestion with a restriction enzyme or addition of a linker, depending on purposes. The DNA may have ATG as a translation initiation codon at the 5' terminal side and have TAA, TGA, or TAG as a translation termination codon at the 3' terminal side. These translation initiation and translation termination codons can also be added using an appropriate synthetic DNA adapter.

In the methods/uses of the invention, BST1 may for example be provided in isolated form, such as where the BST1 polypeptide has been purified to at least to some extent. BST1 polypeptide may be provided in substantially pure form, that is to say free, to a substantial extent, from other proteins. BST1 polypeptide can also be produced using recombinant methods, synthetically produced or produced by a combination of these methods. BST1 can be easily prepared by any method known by persons skilled in the art, which involves producing an expression vector containing appropriate DNA of the present invention or a gene containing a DNA of the present invention, culturing a transformant transformed using the expression vector, generating and accumulating a relevant polypeptide of the present invention or a recombinant protein containing the polypeptide, and then collecting the resultant.

Recombinant BST1 polypeptide may be prepared by processes well known in the art from genetically engineered host cells comprising expression systems. Accordingly, the present invention also relates to expression systems which comprise a BST1 polypeptide or nucleic acid, to host cells which are genetically engineered with such expression systems and to the production of BST1 polypeptide by recombinant techniques. For recombinant BST1 polypeptide production, host cells can be genetically engineered to incorporate expression systems or portions thereof for nucleic acids. Such incorporation can be performed using methods well known in the art, such as, calcium phosphate transfection, DEAD-dextran mediated transfection, transvection, microinjection, cationic lipid-mediated transfection, electroporation, transduction, scrape loading, ballistic introduction or infection (see e.g. Davis et al., Basic Methods in Molecular Biology, 1986 and Sambrook et al., Molecular Cloning: A Laboratory Manual, 2nd Ed., Cold Spring Harbour laboratory Press, Cold Spring Harbour, N.Y., 1989).

As host cells, for example, bacteria of the genus *Escherichia, Streptococci, Staphylococci, Streptomyces*, bacteria of the genus *Bacillus*, yeast, *Aspergillus* cells, insect cells, insects, and animal cells are used. Specific examples of bacteria of the genus *Escherichia*, which are used herein, include *Escherichia coli* K12 and DH1 (*Proc. Natl. Acad. Sci. U.S.A.*, Vol. 60, 160 (1968)), JM103 (*Nucleic Acids Research*, Vol. 9, 309 (1981)), JA221 (*Journal of Molecular Biology*, Vol. 120, 517 (1978)), and HB101 (*Journal of Molecular Biology*, Vol. 41, 459 (1969)). As bacteria of the genus *Bacillus*, for example, *Bacillus subtilis* MI114 (*Gene*, Vol. 24, 255 (1983)) and 207-21 (*Journal of Biochemistry*, Vol. 95, 87 (1984)) are used. As yeast, for example, *Saccaromyces cerevisiae* AH22, AH22R-, NA87-11A, DKD-5D, and 20B-12, *Schizosaccaromyces pombe* NCYC1913 and NCYC2036, and *Pichia pastoris* are used. As insect cells, for example, *Drosophila* S2 and *Spodoptera* Sf9 cells are used. As animal cells, for example, COS-7 and Vero monkey cells, CHO Chinese hamster cells (hereinafter abbreviated as CHO cells), dhfr-gene-deficient CHO cells, mouse L cells, mouse AtT-20 cells, mouse myeloma cells, rat GH3 cells, human FL cells, COS, HeLa, C127, 3T3, HEK 293, BHK and Bowes melanoma cells are used.

Cell-free translation systems can also be employed to produce recombinant polypeptides (e.g. rabbit reticulocyte lysate, wheat germ lysate, SP6/T7 in vitro T&T and RTS 100 *E. Coli* HY transcription and translation kits from Roche Diagnostics Ltd., Lewes, UK and the TNT Quick coupled Transcription/Translation System from Promega UK, Southampton, UK).

The expression vector can be produced according to a method known in the art. For example, the vector can be produced by (1) excising a DNA fragment containing a DNA of the present invention or a gene containing a DNA of the present invention and (2) ligating the DNA fragment downstream of the promoter in an appropriate expression vector. A wide variety of expression systems can be used, such as and without limitation, chromosomal, episomal and virus-derived systems, e.g. plasmids derived from *Escherichia coli* (e.g. pBR322, pBR325, pUC18, and pUC118), plasmids derived from *Bacillus subtilis* (e.g. pUB110, pTP5, and pC194), from bacteriophage, from transposons, from yeast episomes (e.g. pSH19 and pSH15), from insertion elements, from yeast chromosomal elements, from viruses such as baculoviruses, papova viruses such as SV40, vaccinia viruses, adenoviruses, fowl pox viruses, pseudorabies viruses and retroviruses, and vectors derived from combinations thereof, such as those derived from plasmid and bacteriophage (such as [lambda] phage) genetic elements, such as cosmids and phagemids. The expression systems may contain control regions that regulate as well as engender expression. Promoters to be used in the present invention may be any promoters as long as they are appropriate for hosts to be used for gene expression. For example, when a host is *Escherichia coli*, a trp promoter, a lac promoter, a recA promoter, a pL promoter, an lpp promoter, and the like are preferred. When a host is *Bacillus subtilis*, an SPO1 promoter, an SPO2 promoter, a penP promoter, and the like are preferred. When a host is yeast, a PHO5 promoter, a PGK promoter, a GAP promoter, an ADH promoter, and the like are preferred. When an animal cell is used as a host, examples of promoters for use in this case include an SRa promoter, an SV40 promoter, an LTR promoter, a CMV promoter, and an HSV-TK promoter. Generally, any system or vector that is able to maintain, propagate or express a nucleic acid to produce a polypeptide in a host may be used.

The appropriate nucleic acid sequence may be inserted into an expression system by any variety of well known and routine techniques, such as those set forth in Sambrook et al., supra. Appropriate secretion signals may be incorporated into the BST1 polypeptide to allow secretion of the translated protein into the lumen of the endoplasmic reticulum, the periplasmic space or the extracellular environment. These signals may be endogenous to the BST1 polypeptide or they may be heterologous signals. Transformation of the host cells can be carried out according to methods known in the art. For example, the following documents can be referred to: *Proc. Natl. Acad. Sci. U.S.A.*, Vol. 69, 2110 (1972); *Gene*, Vol. 17, 107 (1982); *Molecular & General Genetics*, Vol. 168, 111 (1979); *Methods in Enzymology*, Vol. 194, 182-187 (1991); Proc. Natl. Acad. Sci. U.S.A.), Vol. 75, 1929 (1978); Cell Technology, separate volume 8, New Cell Technology, Experimental Protocol. 263-267 (1995) (issued by Shujunsha); and *Virology*, Vol. 52, 456 (1973). The thus obtained transformant transformed with an expression vector containing a DNA of the present invention or a gene containing a DNA of the present invention can be cultured according to a method known in the art. For example, when hosts are bacteria of the genus *Escherichia*, the bacteria are generally cultured at approximately 15° C. to 43° C. for approximately 3 to 24 hours. If necessary, aeration or agitation can also be added. When hosts are bacteria of the genus *Bacillus*, the bacteria are generally cultured at approximately 30° C. to 40° C. for approximately 6 to 24 hours. If necessary, aeration or agitation can also be added. When transformants whose hosts are yeast are cultured, culture is generally carried out at approximately 20° C. to 35° C. for approximately 24 to 72 hours using media with pH adjusted to be approximately 5 to 8. If necessary, aeration or agitation can also be added. When transformants whose hosts are animal cells are cultured, the cells are generally cultured at approximately 30° C. to 40° C. for approximately 15 to 60 hours using media with the pH adjusted to be approximately 6 to 8. If necessary, aeration or agitation can also be added.

If a BST1 polypeptide is to be expressed for use in cell-based screening assays, it is preferred that the polypeptide be produced at the cell surface. In this event, the cells may be harvested prior to use in the screening assay. If the BST1 polypeptide is secreted into the medium, the medium can be recovered in order to isolate said polypeptide. If produced intracellularly, the cells must first be lysed before the BST1 polypeptide is recovered.

BST1 polypeptide can be recovered and purified from recombinant cell cultures or from other biological sources by well known methods including, ammonium sulphate or ethanol precipitation, acid extraction, anion or cation exchange chromatography, phosphocellulose chromatography, affinity chromatography, hydrophobic interaction chromatography, hydroxylapatite chromatography, molecular sieving chromatography, centrifugation methods, electrophoresis methods and lectin chromatography. In one embodiment, a combination of these methods is used. In another embodiment, high performance liquid chromatography is used. In a further embodiment, an antibody which specifically binds to a BST1 polypeptide can be used to deplete a sample comprising a BST1 polypeptide of said polypeptide or to purify said polypeptide.

To separate and purify a polypeptide or a protein of the present invention from the culture products, for example, after culture, microbial bodies or cells are collected by a known method, they are suspended in an appropriate buffer, the microbial bodies or the cells are disrupted by, for example, ultrasonic waves, lysozymes, and/or freeze-thawing, the resultant is then subjected to centrifugation or filtration, and then a crude extract of the protein can be obtained. The buffer may also contain a protein denaturation agent such as urea or guanidine hydrochloride or a surfactant such as Triton X-100™. When the protein is secreted in a culture solution, microbial bodies or cells and a supernatant are separated by a known method after the completion of culture and then the supernatant is collected. The protein contained in the thus obtained culture supernatant or the extract can be purified by an appropriate combination of known separation and purification methods. The thus obtained polypeptide (protein) of the present invention can be converted into a salt by a known method or a method according thereto. Conversely, when the polypeptide (protein) of the present invention is obtained in the form of a salt, it can be converted into a free protein or peptide or another salt by a known method or a method according thereto. Moreover, an appropriate protein modification enzyme such as trypsin or chymotrypsin is caused to act on a protein produced by a recombinant before or after purification, so that modification can be arbitrarily added or a polypeptide can be partially removed. The presence of a polypeptide (protein) of the present invention or a salt thereof can be measured by various binding assays, enzyme immunoassays using specific antibodies, and the like.

Techniques well known in the art may be used for refolding to regenerate native or active conformations of the BST1 polypeptide when the polypeptide has been denatured during isolation and or purification. In the context of the present invention, BST1 polypeptide can be obtained from a biological sample from any source, such as and without limitation, a blood sample or tissue sample, e.g. a myeloid, breast, colorectal, kidney, lung or pancreatic tissue sample.

BST1 polypeptide may be in the form of a "mature protein" or may be part of a larger protein such as a fusion protein. It is often advantageous to include an additional amino acid sequence which contains secretory or leader sequences, a pre-, pro- or prepro-protein sequence, or a sequence which aids in purification such as an affinity tag, for example, but without limitation, multiple histidine residues, a FLAG tag, HA tag or myc tag.

BST1 may, for example, be fused with a heterologous fusion partner such as the surface protein, known as protein D from *Haemophilus Influenza* B, a non-structural protein from influenzae virus such as NS1, the S antigen from Hepatitis B or a protein known as LYTA such as the C terminal thereof.

An additional sequence that may provide stability during recombinant production may also be used. Such sequences may be optionally removed as required by incorporating a cleavable sequence as an additional sequence or part thereof. Thus, a BST1 polypeptide may be fused to other moieties including other polypeptides or proteins (for example, glutathione S-transferase and protein A). Such a fusion protein can be cleaved using an appropriate protease, and then separated into each protein. Such additional sequences and affinity tags are well known in the art. In addition to the above, features known in the art, such as an enhancer, a splicing signal, a polyA addition signal, a selection marker, and an SV40 replication origin can be added to an expression vector, if desired.

Production of Affinity Reagents to BST1

According to those in the art, there are three main types of immunoaffinity reagent—monoclonal antibodies, phage display antibodies and smaller antibody-derived molecules such as Affibodies, Domain Antibodies (dAbs), Nanobodies, UniBodies, DARPins, Anticalins, Duocalins, Avimers or Versabodies. In general in applications according to the present invention where the use of antibodies is stated, other affinity reagents (e.g. Affibodies, Domain Antibodies, Nanobodies, UniBodies, DARPins, Anticalins, Duocalins, Avimers or Versabodies) may be employed. Such substances may be said to be capable of immunospecific binding to BST1. Where appropriate the term "affinity agent" shall be construed to embrace immunoaffinity reagents and other substances capable of specific binding to BST1 including but not limited to ligands, lectins, streptavidins, antibody mimetics and synthetic binding agents.

Production of Antibodies to BST1

According to the invention BST1, a BST1 analog, a BST1-related protein or a fragment or derivative of any of the foregoing may be used as an immunogen to generate antibodies which immunospecifically bind such an immunogen. Such immunogens can be isolated by any convenient means, including the methods described above. The term "antibody" as used herein refers to a peptide or polypeptide derived from, modeled after or substantially encoded by an immunoglobulin gene or immunoglobulin genes, or fragments thereof, capable of specifically binding an antigen or epitope. See, e.g. *Fundamental Immunology*, 3$^{rd}$ Edition, W. E. Paul, ed., Raven Press, N.Y. (1993); Wilson (1994) *J. Immunol. Methods* 175:267-273; Yarmush (1992) *J. Biochem. Biophys. Methods* 25:85-97. The term antibody includes antigen-binding portions, i.e., "antigen binding sites" (e.g. fragments, subsequences, complementarity determining regions (CDRs)) that retain capacity to bind antigen, including (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Single chain antibodies are also included by reference in the term "antibody". Antibodies of the invention include, but are not limited to polyclonal, monoclonal, bispecific, humanized or chimeric antibodies, single chain antibodies, Fab fragments and F(ab')$_2$ fragments, fragments produced by a Fab expression library, anti-idiotypic (anti-Id) antibodies, and epitope-binding fragments of any of the above. The immunoglobulin molecules of the invention can be of any class (e.g. IgG, IgE, IgM, IgD and IgA such as IgG) or subclass of immunoglobulin molecule.

The term "specifically binds" (or "immunospecifically binds") is not intended to indicate that an antibody binds exclusively to its intended target. Rather, an antibody "specifically binds" if its affinity for its intended target is typically about 5-fold greater when compared to its affinity for a non-target molecule. Suitably there is no significant cross-reaction or cross-binding with undesired substances, especially naturally occurring proteins or tissues of a healthy person or animal. Preferably the affinity of the antibody will be at least about 5 fold, preferably 10 fold, more preferably 25-fold, even more preferably 50-fold, and most preferably 100-fold or more, greater for a target molecule than its affinity for a non-target molecule. In some embodiments, specific binding between an antibody or other binding agent and an antigen means a binding affinity of at least $10^6$ $M^{-1}$. Antibodies may, for example, bind with affinities of at least about $10^7$ $M^{-1}$, and preferably between about $10^8$ $M^{-1}$ to about $10^9$ $M^{-1}$, about $10^9$ $M^{-1}$ to about $10^{10}$ $M^{-1}$, or about $10^{10}$ $M^{-1}$ to about $10^{11}$ $M^{-1}$.

Affinity is calculated as $K_d=k_{off}/k_{on}$ ($k_{off}$ is the dissociation rate constant, $k_{on}$ is the association rate constant and $K_d$ is the equilibrium constant. Affinity can be determined at equilibrium by measuring the fraction bound (r) of labeled ligand at various concentrations (c). The data are graphed using the Scatchard equation: $r/c=K(n-r)$:

where
r=moles of bound ligand/mole of receptor at equilibrium;
c=free ligand concentration at equilibrium;
K=equilibrium association constant; and
n=number of ligand binding sites per receptor molecule By graphical analysis, r/c is plotted on the Y-axis versus r on the X-axis thus producing a Scatchard plot. The affinity is the negative slope of the line. $k_{off}$ can be determined by competing bound labeled ligand with unlabeled excess ligand (see, e.g. U.S. Pat. No. 6,316,409). The affinity of a targeting agent for its target molecule is for example at least about $1\times10^{-6}$ moles/liter, such as at least about $1\times10^{-7}$ moles/liter, such as at least about $1\times10^{-8}$ moles/liter, especially at least about $1\times10^{-9}$ moles/liter, and particularly at least about $1\times10^{-10}$ moles/liter. Antibody affinity measurement by Scatchard analysis is well known in the art. See, e.g. van Erp et al., *J. Immunoassay* 12: 425-43, 1991; Nelson and Griswold, *Comput. Methods Programs Biomed.* 27: 65-8, 1988.

In one embodiment, antibodies that recognize gene products of genes encoding BST1 are publicly available. In another embodiment, methods known to those skilled in the art are used to produce antibodies that recognize BST1, a BST1 analog, a BST1-related polypeptide, or a fragment or derivative of any of the foregoing. One skilled in the art will recognize that many procedures are available for the production of antibodies, for example, as described in Antibodies, A Laboratory Manual, Ed Harlow and David Lane, Cold Spring Harbor Laboratory (1988), Cold Spring Harbor, N.Y. One skilled in the art will also appreciate that binding fragments or Fab fragments which mimic antibodies can also be prepared from genetic information by various procedures (Antibody Engineering: A Practical Approach (Borrebaeck, C., ed.), 1995, Oxford University Press, Oxford; J. Immunol. 149, 3914-3920 (1992)).

In one embodiment of the invention, antibodies to a specific domain of BST1 are produced. In a specific embodiment, hydrophilic fragments of BST1 are used as immunogens for antibody production.

In the production of antibodies, screening for the desired antibody can be accomplished by techniques known in the art, e.g. ELISA (enzyme-linked immunosorbent assay). For example, to select antibodies which recognize a specific domain of BST1, one may assay generated hybridomas for a product which binds to a BST1 fragment containing such domain. For selection of an antibody that specifically binds a first BST1 homolog but which does not specifically bind to (or binds less avidly to) a second BST1 homolog, one can select on the basis of positive binding to the first BST1 homolog and a lack of binding to (or reduced binding to) the second BST1 homolog. Similarly, for selection of an antibody that specifically binds BST1 but which does not specifically bind to (or binds less avidly to) a different isoform of the same protein (such as a different glycoform having the same core peptide as BST1), one can select on the basis of positive binding to BST1 and a lack of binding to (or reduced binding to) the different isoform (e.g. a different glycoform). Thus, the present invention provides an antibody (such as a monoclonal antibody) that binds with greater affinity (for example at least 2-fold, such as at least 5-fold, particularly at least 10-fold greater affinity) to BST1 than to a different isoform or isoforms (e.g. glycoforms) of BST1.

Polyclonal antibodies which may be used in the methods of the invention are heterogeneous populations of antibody molecules derived from the sera of immunized animals. Unfractionated immune serum can also be used. Various procedures known in the art may be used for the production of polyclonal antibodies to BST1, a fragment of BST1, a BST1-related polypeptide, or a fragment of a BST1-related polypeptide. For example, one way is to purify polypeptides of interest or to synthesize the polypeptides of interest using, e.g. solid phase peptide synthesis methods well known in the art. See, e.g. *Guide to Protein Purification*, Murray P. Deutcher, ed., *Meth. Enzymol.* Vol 182 (1990); Solid Phase Peptide Synthesis, Greg B. Fields ed., *Meth. Enzymol.* Vol 289 (1997); Kiso et al., *Chem. Pharm. Bull.* (Tokyo) 38: 1192-99, 1990; Mostafavi et al., *Biomed. Pept. Proteins Nucleic Acids* 1: 255-60, 1995; Fujiwara et al., *Chem. Pharm. Bull.* (Tokyo) 44: 1326-31, 1996. The selected polypeptides may then be used to immunize by injection various host animals, including but not limited to rabbits, mice, rats, etc., to generate polyclonal or monoclonal antibodies. If BST1 is purified by gel electrophoresis, BST1 can be used for immunization with or without prior extraction from the polyacrylamide gel. Various adjuvants (i e immunostimulants) may be used to enhance the immunological response, depending on the host species, including, but not limited to, complete or incomplete Freund's adjuvant, a mineral gel such as aluminum hydroxide, surface active substance such as lysolecithin, pluronic polyol, a polyanion, a peptide, an oil emulsion, keyhole limpet hemocyanin, dinitrophenol, and an adjuvant such as BCG (bacille Calmette-Guerin) or *corynebacterium parvum*. Additional adjuvants are also well known in the art.

For preparation of monoclonal antibodies (mAbs) directed toward BST1, a fragment of BST1, a BST1-related polypeptide, or a fragment of a BST1-related polypeptide, any technique which provides for the production of antibody molecules by continuous cell lines in culture may be used. For example, the hybridoma technique originally developed by Kohler and Milstein (1975, Nature 256:495-497), as well as the trioma technique, the human B-cell hybridoma technique (Kozbor et al., 1983, Immunology Today 4:72), and the EBV-hybridoma technique to produce human monoclonal antibodies (Cole et al., 1985, in Monoclonal Antibodies and Cancer Therapy, Alan R. Liss, Inc., pp. 77-96). Such antibodies may be of any immunoglobulin class including IgG, IgM, IgE, IgA, IgD and any subclass thereof. The hybridoma producing the mAbs of the invention may be cultivated in vitro or in vivo. In an additional embodiment of the invention, monoclonal antibodies can be produced in germ-free animals utilizing known technology (PCT/US90/02545, incorporated herein by reference).

The monoclonal antibodies include but are not limited to human monoclonal antibodies and chimeric monoclonal antibodies (e.g. human-mouse chimeras). A chimeric antibody is a molecule in which different portions are derived from different animal species, such as those having a human immunoglobulin constant region and a variable region derived from a murine mAb. (See, e.g. Cabilly et al., U.S. Pat. No. 4,816,567; and Boss et al., U.S. Pat. No. 4,816,397, which are incorporated herein by reference in their entirety.) Humanized antibodies are antibody molecules from non-human species having one or more complementarity determining regions (CDRs) from the non-human species and a framework region from a human immunoglobulin molecule. (See, e.g. Queen, U.S. Pat. No. 5,585,089, which is incorporated herein by reference in its entirety.)

Chimeric and humanized monoclonal antibodies can be produced by recombinant DNA techniques known in the art, for example using methods described in PCT Publication No. WO 87/02671; European Patent Application 184,187; European Patent Application 171,496; European Patent Application 173,494; PCT Publication No. WO 86/01533; U.S. Pat. No. 4,816,567; European Patent Application 125,023; Better et al., 1988, *Science* 240:1041-1043; Liu et al., 1987, *Proc. Natl. Acad. Sci. USA* 84:3439-3443; Liu et al., 1987, *J. Immunol.* 139:3521-3526; Sun et al., 1987, *Proc. Natl. Acad. Sci. USA* 84:214-218; Nishimura et al., 1987, *Canc. Res.* 47:999-1005; Wood et al., 1985, *Nature* 314:446-449; and Shaw et al., 1988, *J. Natl. Cancer Inst.* 80:1553-1559; Morrison, 1985, *Science* 229:1202-1207; Oi et al., 1986, *BioTechniques* 4:214; U.S. Pat. No. 5,225,539; Jones et al., 1986, *Nature* 321:552-525; Verhoeyan et al. (1988) *Science* 239:1534; and Beidler et al., 1988, *J. Immunol.* 141:4053-4060.

Completely human antibodies are particularly desirable for therapeutic treatment of human subjects. Such antibodies can be produced using transgenic mice which are incapable of expressing endogenous immunoglobulin heavy and light chain genes, but which can express human heavy and light chain genes. The transgenic mice are immunized in the normal fashion with a selected antigen, e.g. all or a portion of BST1. Monoclonal antibodies directed against the antigen can be obtained using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar (1995, *Int. Rev. Immunol.* 13:65-93). For a detailed discussion of this technology for producing human antibodies and human monoclonal antibodies and protocols for producing such antibodies, see, e.g. U.S. Pat. Nos. 5,625,126; 5,633,425; 5,569,825; 5,661,016; and 5,545,806. In addition, companies such as Abgenix, Inc. (Freemont, Calif.) and Genpharm (San Jose, Calif.) can be engaged to provide human antibodies directed against a selected antigen using technology similar to that described above.

Completely human antibodies which recognize a selected epitope can be generated using a technique referred to as "guided selection". In this approach a selected non-human monoclonal antibody, e.g. a mouse antibody, is used to guide the selection of a completely human antibody recognizing the same epitope. (Jespers et al. (1994) *BioTechnology* 12:899-903).

The antibodies of the present invention can also be generated by the use of phage display technology to produce and screen libraries of polypeptides for binding to a selected target. See, e.g. Cwirla et al., *Proc. Natl. Acad. Sci. USA* 87, 6378-82, 1990; Devlin et al., *Science* 249, 404-6, 1990, Scott and Smith, *Science* 249, 386-88, 1990; and Ladner et al., U.S. Pat. No. 5,571,698. A basic concept of phage display methods is the establishment of a physical association between DNA encoding a polypeptide to be screened and the polypeptide. This physical association is provided by the phage particle, which displays a polypeptide as part of a capsid enclosing the phage genome which encodes the polypeptide. The establishment of a physical association between polypeptides and their genetic material allows simultaneous mass screening of very large numbers of phage bearing different polypeptides. Phage displaying a polypeptide with affinity to a target bind to the target and these phage are enriched by affinity screening to the target. The identity of polypeptides displayed from these phage can be determined from their respective genomes. Using these methods a polypeptide identified as having a binding affinity for a desired target can then be synthesized in bulk by conventional means. See, e.g. U.S. Pat. No. 6,057,098, which is hereby incorporated in its entirety, including all tables, figures, and claims. In particular, such phage can be utilized to display antigen binding domains expressed from a repertoire or combinatorial antibody library (e.g. human or murine). Phage expressing an antigen binding domain that binds the antigen of interest can be selected or identified with antigen, e.g. using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Phage display methods that can be used to make the antibodies of the present invention include those disclosed in Brinkman et al., *J. Immunol. Methods* 182:41-50 (1995); Ames et al., *J. Immunol. Methods* 184:177-186 (1995); Kettleborough et al., *Eur. J. Immunol.* 24:952-958 (1994); Persic et al., *Gene* 187 9-18 (1997); Burton et al., *Advances in Immunology* 57:191-280 (1994); PCT Application No. PCT/GB91/01134; PCT Publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g. as described in detail below. For example, techniques to recombinantly produce Fab, Fab' and F(ab')$_2$ fragments can also be employed using methods known in the art such as those disclosed in PCT publication WO 92/22324; Mullinax et al., BioTechniques 12(6):864-869 (1992); and Sawai et al., AJRI 34:26-34 (1995); and Better et al., Science 240:1041-1043 (1988) (said references incorporated by reference in their entireties).

Examples of techniques which can be used to produce single-chain Fvs and antibodies include those described in U.S. Pat. Nos. 4,946,778 and 5,258,498; Huston et al., *Methods in Enzymology* 203:46-88 (1991); Shu et al., *PNAS* 90:7995-7999 (1993); and Skerra et al., *Science* 240:1038-1040 (1988).

The invention further provides for the use of bispecific antibodies, which can be made by methods known in the art. Traditional production of full length bispecific antibodies is based on the coexpression of two immunoglobulin heavy chain-light chain pairs, where the two chains have different specificities (Milstein et al., 1983, Nature 305:537-539). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, published 13 May 1993, and in Traunecker et al., 1991, EMBO J. 10:3655-3659.

According to a different and more preferred approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690 published Mar. 3, 1994. For further details for generating bispecific antibodies see, for example, Suresh et al., Methods in Enzymology, 1986, 121:210.

The invention provides functionally active fragments, derivatives or analogs of the anti-BST1 immunoglobulin molecules. Functionally active means that the fragment, derivative or analog is able to elicit anti-anti-idiotype antibodies (i.e., tertiary antibodies) that recognize the same antigen that is recognized by the antibody from which the fragment, derivative or analog is derived. Specifically, in a preferred embodiment the antigenicity of the idiotype of the immunoglobulin molecule may be enhanced by deletion of framework and CDR sequences that are C-terminal to the CDR sequence that specifically recognizes the antigen. To determine which CDR sequences bind the antigen, synthetic peptides containing the CDR sequences can be used in binding assays with the antigen by any binding assay method known in the art.

The present invention provides antibody fragments such as, but not limited to, F(ab')$_2$ fragments and Fab fragments. Antibody fragments which recognize specific epitopes may be generated by known techniques. F(ab')$_2$ fragments consist of the variable region, the light chain constant region and the CH1 domain of the heavy chain and are generated by pepsin digestion of the antibody molecule. Fab fragments are generated by reducing the disulfide bridges of the F(ab')$_2$ fragments. The invention also provides heavy chain and light chain dimers of the antibodies of the invention, or any minimal fragment thereof such as Fvs or single chain antibodies (SCAs) (e.g. as described in U.S. Pat. No. 4,946,778; Bird, 1988, *Science* 242:423-42; Huston et al., 1988, *Proc. Natl. Acad. Sci. USA* 85:5879-5883; and Ward et al., 1989, *Nature* 334:544-54), or any other molecule with the same specificity as the antibody of the invention. Single chain antibodies are formed by linking the heavy and light chain fragments of the Fv region via an amino acid bridge, resulting in a single chain polypeptide. Techniques for the assembly of functional Fv fragments in *E. coli* may be used (Skerra et al., 1988, *Science* 242:1038-1041).

In other embodiments, the invention provides fusion proteins of the immunoglobulins of the invention (or functionally active fragments thereof), for example in which the immunoglobulin is fused via a covalent bond (e.g. a peptide bond), at either the N-terminus or the C-terminus to an amino acid sequence of another protein (or portion thereof, preferably at least 10, 20 or 50 amino acid portion of the protein) that is not the immunoglobulin. Preferably the immunoglobulin, or fragment thereof, is covalently linked to the other protein at the N-terminus of the constant domain. As stated above, such fusion proteins may facilitate purification, increase half-life in vivo, and enhance the delivery of an antigen across an epithelial barrier to the immune system.

The immunoglobulins of the invention include analogs and derivatives that are modified, i.e., by the covalent attachment of any type of molecule as long as such covalent attachment does not impair immunospecific binding. For example, but not by way of limitation, the derivatives and analogs of the immunoglobulins include those that have been further modified, e.g. by glycosylation, acetylation, pegylation, phosphylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, etc. Additionally, the analog or derivative may contain one or more non-classical amino acids.

The foregoing antibodies can be used in methods known in the art relating to the localization and activity of BST1, e.g., for imaging this protein, measuring levels thereof in appropriate physiological samples, in diagnostic methods, etc.

Production of Affibodies to BST1

Affibody molecules represent a new class of affinity proteins based on a 58-amino acid residue protein domain, derived from one of the IgG-binding domains of staphylococcal protein A. This three helix bundle domain has been used as a scaffold for the construction of combinatorial phagemid libraries, from which Affibody variants that target the desired molecules can be selected using phage display technology (Nord K, Gunneriusson E, Ringdahl J, Stahl S, Uhlen M, Nygren P A, Binding proteins selected from combinatorial libraries of an α-helical bacterial receptor domain, *Nat Biotechnol* 1997; 15:772-7. Ronmark J, Gronlund H, Uhlen M, Nygren P A, Human immunoglobulin A (IgA)-specific ligands from combinatorial engineering of protein A, *Eur J Biochem* 2002; 269:2647-55.). The simple, robust structure of Affibody molecules in combination with their low molecular weight (6 kDa), make them suitable for a wide variety of applications, for instance, as detection reagents (Ronmark J, Hansson M, Nguyen T, et al, Construction and characterization of Affibody-Fc chimeras produced in *Escherichia coli*, *J Immunol Methods* 2002; 261: 199-211) and to inhibit receptor interactions (Sandstorm K, Xu Z, Forsberg G, Nygren P A, Inhibition of the CD28-CD80 co-stimulation signal by a CD28-binding Affibody ligand developed by combinatorial protein engineering, *Protein Eng* 2003; 16:691-7). Further details of Affibodies and methods of production thereof may be obtained by reference to U.S. Pat. No. 5,831,012 which is herein incorporated by reference in its entirety.

Labelled Affibodies may also be useful in imaging applications for determining abundance of Isoforms.

Production of Domain Antibodies to BST1

References to antibodies herein embrace references to Domain Antibodies. Domain Antibodies (dAbs) are the smallest functional binding units of antibodies, corresponding to the variable regions of either the heavy (VH) or light (VL) chains of human antibodies. Domain Antibodies have a molecular weight of approximately 13 kDa. Domantis has developed a series of large and highly functional libraries of fully human VH and VL dAbs (more than ten billion different sequences in each library), and uses these libraries to select dAbs that are specific to therapeutic targets. In contrast to many conventional antibodies, Domain Antibodies are well expressed in bacterial, yeast, and mammalian cell systems. Further details of domain antibodies and methods of production thereof may be obtained by reference to U.S. Pat. Nos. 6,291,158; 6,582,915; 6,593,081; 6,172,197; 6,696,245; US Serial No. 2004/0110941; European patent application No. 1433846 and European Patents 0368684 & 0616640; WO05/035572, WO04/101790, WO04/081026, WO04/058821, WO04/003019 and WO03/002609, each of which is herein incorporated by reference in its entirety.

Production of Nanobodies to BST1

Nanobodies are antibody-derived therapeutic proteins that contain the unique structural and functional properties of naturally-occurring heavy-chain antibodies. These heavy-chain antibodies contain a single variable domain (VHH) and two constant domains ($C_H2$ and $C_H3$). Importantly, the cloned and isolated VHH domain is a perfectly stable polypeptide harbouring the full antigen-binding capacity of the original heavy-chain antibody. Nanobodies have a high homology with the $V_H$ domains of human antibodies and can be further humanised without any loss of activity. Importantly, Nanobodies have a low immunogenic potential, which has been confirmed in primate studies with Nanobody lead compounds.

Nanobodies combine the advantages of conventional antibodies with important features of small molecule drugs. Like conventional antibodies, Nanobodies show high target specificity, high affinity for their target and low inherent toxicity. However, like small molecule drugs they can inhibit enzymes and readily access receptor clefts. Furthermore, Nanobodies are extremely stable, can be administered by means other than injection (see e.g. WO 04/041867, which is herein incorporated by reference in its entirety) and are easy to manufacture. Other advantages of Nanobodies include recognising uncommon or hidden epitopes as a result of their small size, binding into cavities or active sites of protein targets with high affinity and selectivity due to their unique 3-dimensional, drug format flexibility, tailoring of half-life and ease and speed of drug discovery.

Nanobodies are encoded by single genes and are efficiently produced in almost all prokaryotic and eukaryotic hosts e.g. *E. coli* (see e.g. U.S. Pat. No. 6,765,087, which is herein incorporated by reference in its entirety), moulds (for example *Aspergillus* or *Trichoderma*) and yeast (for example *Saccharomyces, Kluyveromyces, Hansenula* or *Pichia*) (see e.g. U.S. Pat. No. 6,838,254, which is herein incorporated by reference in its entirety). The production process is scalable and multi-kilogram quantities of Nanobodies have been produced. Because Nanobodies exhibit a superior stability compared with conventional antibodies, they can be formulated as a long shelf-life, ready-to-use solution.

The Nanoclone method (see e.g. WO 06/079372, which is herein incorporated by reference in its entirety) is a proprietary method for generating Nanobodies against a desired target, based on automated high-throughput selection of B-cells.

Production of UniBodies to BST1

UniBodies are another antibody fragment technology; however this one is based upon the removal of the hinge region of IgG4 antibodies. The deletion of the hinge region results in a molecule that is essentially half the size of traditional IgG4 antibodies and has a univalent binding region rather than the bivalent binding region of IgG4 antibodies. It is also well known that IgG4 antibodies are inert and thus do not interact with the immune system, which may be advantageous for the treatment of diseases where an immune response is not desired, and this advantage is passed onto UniBodies. For example, UniBodies may function to inhibit or silence, but not kill, the cells to which they are bound. Additionally, UniBody binding to cancer cells do not stimulate them to proliferate. Furthermore, because UniBodies are about half the size of traditional IgG4 antibodies, they may show better distribution over larger solid tumors with potentially advantageous efficacy. UniBodies are cleared from the body at a similar rate to whole IgG4 antibodies and are able to bind with a similar affinity for their antigens as whole antibodies. Further details of UniBodies may be obtained by reference to patent WO2007/059782, which is herein incorporated by reference in its entirety.

Production of DARPins to BST1

DARPins (Designed Ankyrin Repeat Proteins) are one example of an antibody mimetic DRP (Designed Repeat Protein) technology that has been developed to exploit the binding abilities of non-antibody polypeptides. Repeat proteins such as ankyrin or leucine-rich repeat proteins, are ubiquitous binding molecules, which occur, unlike antibodies, intra- and extracellularly. Their unique modular architecture features repeating structural units (repeats), which stack together to form elongated repeat domains displaying variable and modular target-binding surfaces. Based on this modularity, combinatorial libraries of polypeptides with highly diversified binding specificities can be generated. This strategy includes the consensus design of self-compatible repeats displaying variable surface residues and their random assembly into repeat domains.

DARPins can be produced in bacterial expression systems at very high yields and they belong to the most stable proteins known. Highly specific, high-affinity DARPins to a broad range of target proteins, including human receptors, cytokines, kinases, human proteases, viruses and membrane proteins, have been selected. DARPins having affinities in the single-digit nanomolar to picomolar range can be obtained.

DARPins have been used in a wide range of applications, including ELISA, sandwich ELISA, flow cytometric analysis (FACS), immunohistochemistry (IHC), chip applications, affinity purification or Western blotting. DARPins also proved to be highly active in the intracellular compartment for example as intracellular marker proteins fused to green fluorescent protein (GFP). DARPins were further used to inhibit viral entry with IC50 in the pM range. DARPins are not only ideal to block protein-protein interactions, but also to inhibit enzymes. Proteases, kinases and transporters have been successfully inhibited, most often an allosteric inhibition mode. Very fast and specific enrichments on the tumor and very favorable tumor to blood ratios make DARPins well suited for in vivo diagnostics or therapeutic approaches.

Additional information regarding DARPins and other DRP technologies can be found in US Patent Application Publication No. 2004/0132028, and International Patent Application Publication No. WO02/20565, both of which are hereby incorporated by reference in their entirety.

Production of Anticalins to BST1

Anticalins are an additional antibody mimetic technology, however in this case the binding specificity is derived from lipocalins, a family of low molecular weight proteins that are naturally and abundantly expressed in human tissues and body fluids. Lipocalins have evolved to perform a range of functions in vivo associated with the physiological transport and storage of chemically sensitive or insoluble compounds. Lipocalins have a robust intrinsic structure comprising a highly conserved β-barrel which supports four loops at one terminus of the protein. These loops form the entrance to a binding pocket and conformational differences in this part of the molecule account for the variation in binding specificity between individual lipocalins.

While the overall structure of hypervariable loops supported by a conserved β-sheet framework is reminiscent of immunoglobulins, lipocalins differ considerably from antibodies in terms of size, being composed of a single polypeptide chain of 160-180 amino acids which is marginally larger than a single immunoglobulin domain.

Lipocalins are cloned and their loops are subjected to engineering in order to create Anticalins. Libraries of structurally diverse Anticalins have been generated and Anticalin display allows the selection and screening of binding function, followed by the expression and production of soluble protein for further analysis in prokaryotic or eukaryotic systems. Studies have successfully demonstrated that Anticalins can be developed that are specific for virtually any human target protein; they can be isolated and binding affinities in the nanomolar or higher range can be obtained.

Anticalins can also be formatted as dual targeting proteins, so-called Duocalins. A Duocalin binds two separate therapeutic targets in one easily produced monomeric protein using standard manufacturing processes while retaining target specificity and affinity regardless of the structural orientation of its two binding domains.

Modulation of multiple targets through a single molecule is particularly advantageous in diseases known to involve more than a single causative factor. Moreover, bi- or multivalent binding formats such as Duocalins have significant potential in targeting cell surface molecules in disease, mediating agonistic effects on signal transduction pathways or inducing enhanced internalization effects via binding and clustering of cell surface receptors. Furthermore, the high intrinsic stability of Duocalins is comparable to monomeric Anticalins, offering flexible formulation and delivery potential for Duocalins.

Additional information regarding Anticalins can be found in U.S. Pat. No. 7,250,297 and International Patent Application Publication No. WO 99/16873, both of which are hereby incorporated by reference in their entirety.

Production of Avimers to BST1

Avimers are evolved from a large family of human extracellular receptor domains by in vitro exon shuffling and phage display, generating multidomain proteins with binding and inhibitory properties. Linking multiple independent binding domains has been shown to create avidity and results in improved affinity and specificity compared with conventional single-epitope binding proteins. Other potential advantages include simple and efficient production of multitarget-specific molecules in Escherichia coli, improved thermostability and resistance to proteases. Avimers with sub-nanomolar affinities have been obtained against a variety of targets.

Additional information regarding Avimers can be found in US Patent Application Publication Nos. 2006/0286603, 2006/0234299, 2006/0223114, 2006/0177831, 2006/0008844, 2005/0221384, 2005/0164301, 2005/0089932, 2005/0053973, 2005/0048512, 2004/0175756, all of which are hereby incorporated by reference in their entirety.

Production of Versabodies to BST1

Versabodies are small proteins of 3-5 kDa with >15% cysteines, which form a high disulfide density scaffold, replacing the hydrophobic core that typical proteins have. The replacement of a large number of hydrophobic amino acids, comprising the hydrophobic core, with a small number of disulfides results in a protein that is smaller, more hydrophilic (less aggregation and non-specific binding), more resistant to proteases and heat, and has a lower density of T-cell epitopes, because the residues that contribute most to MHC presentation are hydrophobic. All four of these properties are well-known to affect immunogenicity, and together they are expected to cause a large decrease in immunogenicity.

The inspiration for Versabodies comes from the natural injectable biopharmaceuticals produced by leeches, snakes, spiders, scorpions, snails, and anemones, which are known to exhibit unexpectedly low immunogenicity. Starting with selected natural protein families, by design and by screening the size, hydrophobicity, proteolytic antigen processing, and epitope density are minimized to levels far below the average for natural injectable proteins.

Given the structure of Versabodies, these antibody mimetics offer a versatile format that includes multi-valency, multi-specificity, a diversity of half-life mechanisms, tissue targeting modules and the absence of the antibody Fc region. Furthermore, Versabodies are manufactured in E. coli at high yields, and because of their hydrophilicity and small size, Versabodies are highly soluble and can be formulated to high concentrations. Versabodies are exceptionally heat stable (they can be boiled) and offer extended shelf-life.

Additional information regarding Versabodies can be found in US Patent Application Publication No. 2007/0191272 which is hereby incorporated by reference in its entirety.

Expression of Affinity Reagents

Expression of Antibodies

The antibodies of the invention can be produced by any method known in the art for the synthesis of antibodies, in particular, by chemical synthesis or by recombinant expression, and are preferably produced by recombinant expression techniques.

Recombinant expression of antibodies, or fragments, derivatives or analogs thereof, requires construction of a nucleic acid that encodes the antibody. If the nucleotide sequence of the antibody is known, a nucleic acid encoding the antibody may be assembled from chemically synthesized oligonucleotides (e.g. as described in Kutmeier et al., 1994, *BioTechniques* 17:242), which, briefly, involves the synthesis of overlapping oligonucleotides containing portions of the sequence encoding antibody, annealing and ligation of those oligonucleotides, and then amplification of the ligated oligonucleotides by PCR.

Alternatively, the nucleic acid encoding the antibody may be obtained by cloning the antibody. If a clone containing the nucleic acid encoding the particular antibody is not available, but the sequence of the antibody molecule is known, a nucleic acid encoding the antibody may be obtained from a suitable source (e.g. an antibody cDNA library, or cDNA library generated from any tissue or cells expressing the antibody) by PCR amplification using synthetic primers hybridizable to the 3' and 5' ends of the sequence or by cloning using an oligonucleotide probe specific for the particular gene sequence.

If an antibody molecule that specifically recognizes a particular antigen is not available (or a source for a cDNA library for cloning a nucleic acid encoding such an antibody), antibodies specific for a particular antigen may be generated by any method known in the art, for example, by immunizing an animal, such as a rabbit, to generate polyclonal antibodies or, for example, by generating monoclonal antibodies. Alternatively, a clone encoding at least the Fab portion of the antibody may be obtained by screening Fab expression libraries (e.g. as described in Huse et al., 1989, *Science* 246:1275-1281) for clones of Fab fragments that bind the specific antigen or by screening antibody libraries (See, e.g. Clackson et al., 1991, Nature 352:624; Hane et al., 1997 *Proc. Natl. Acad. Sci. USA* 94:4937).

Once a nucleic acid encoding at least the variable domain of the antibody molecule is obtained, it may be introduced into a vector containing the nucleotide sequence encoding the constant region of the antibody molecule (see, e.g. PCT Publication WO 86/05807; PCT Publication WO 89/01036; and U.S. Pat. No. 5,122,464). Vectors containing the complete light or heavy chain for co-expression with the nucleic acid to allow the expression of a complete antibody molecule are also available. Then, the nucleic acid encoding the antibody can be used to introduce the nucleotide substitution(s) or deletion(s) necessary to substitute (or delete) the one or more variable region cysteine residues participating in an intrachain disulfide bond with an amino acid residue that does not contain a sulfhydyl group. Such modifications can be carried out by any method known in the art for the introduction of specific mutations or deletions in a nucleotide sequence, for example, but not limited to, chemical mutagenesis, in vitro site directed mutagenesis (Hutchinson et al., 1978, *J. Biol. Chem.* 253:6551), PCR based methods, etc.

In addition, techniques developed for the production of "chimeric antibodies" (Morrison et al., 1984, *Proc. Natl. Acad. Sci. USA* 81:851-855; Neuberger et al., 1984, *Nature* 312:604-608; Takeda et al., 1985, *Nature* 314:452-454) by splicing genes from a mouse antibody molecule of appropriate antigen specificity together with genes from a human antibody molecule of appropriate biological activity can be used. As described supra, a chimeric antibody is a molecule in which different portions are derived from different animal species, such as those having a variable region derived from a murine mAb and a human antibody constant region, e.g. humanized antibodies.

Once a nucleic acid encoding an antibody molecule of the invention has been obtained, the vector for the production of the antibody molecule may be produced by recombinant DNA technology using techniques well known in the art. Thus, methods for preparing the protein of the invention by expressing nucleic acid containing the antibody molecule sequences are described herein. Methods which are well known to those skilled in the art can be used to construct expression vectors containing an antibody molecule coding sequences and appropriate transcriptional and translational control signals. These methods include, for example, in vitro recombinant DNA techniques, synthetic techniques, and in vivo genetic recombination. See, for example, the techniques described in Sambrook et al. (1990, Molecular Cloning, A Laboratory Manual, $2^{nd}$ Ed., Cold Spring Harbor Laboratory, Cold Spring Harbor, N.Y.) and Ausubel et al. (eds., 1998, Current Protocols in Molecular Biology, John Wiley & Sons, NY).

The expression vector is transferred to a host cell by conventional techniques and the transfected cells are then cultured by conventional techniques to produce an antibody of the invention.

The host cells used to express a recombinant antibody of the invention may be either bacterial cells such as *Escherichia coli*, or, preferably, eukaryotic cells, especially for the expression of whole recombinant antibody molecule. In particular, mammalian cells such as Chinese hamster ovary cells (CHO), in conjunction with a vector such as the major intermediate early gene promoter element from human cytomegalovirus are an effective expression system for antibodies (Foecking et al., 1986, *Gene* 45:101; Cockett et al., 1990, *BioTechnology* 8:2).

A variety of host-expression vector systems may be utilized to express an antibody molecule of the invention. Such host-expression systems represent vehicles by which the coding sequences of interest may be produced and subsequently purified, but also represent cells which may, when transformed or transfected with the appropriate nucleotide coding sequences, express the antibody molecule of the invention in situ. These include but are not limited to microorganisms such as bacteria (e.g. *E. coli, B. subtilis*) transformed with recombinant bacteriophage DNA, plasmid DNA or cosmid DNA expression vectors containing antibody coding sequences; yeast (e.g. *Saccharomyces, Pichia*) transformed with recombinant yeast expression vectors containing antibody coding sequences; insect cell systems infected with recombinant virus expression vectors (e.g. baculovirus) containing the antibody coding sequences; plant cell systems infected with recombinant virus expression vectors (e.g. cauliflower mosaic virus, CaMV; tobacco mosaic virus, TMV) or transformed with recombinant plasmid expression vectors (e.g. Ti plasmid) containing antibody coding sequences; or mammalian cell systems (e.g. COS, CHO, BHK, 293, 3T3 cells) harboring recombinant expression constructs containing promoters derived from the genome of mammalian cells (e.g. metallothionein promoter) or from mammalian viruses (e.g. the adenovirus late promoter; the vaccinia virus 7.5K promoter).

In bacterial systems, a number of expression vectors may be advantageously selected depending upon the use intended for the antibody molecule being expressed. For example, when a large quantity of such a protein is to be produced, for the generation of pharmaceutical compositions comprising an antibody molecule, vectors which direct the expression of high levels of fusion protein products that are readily purified may be desirable. Such vectors include, but are not limited, to the *E. coli* expression vector pUR278 (Ruther et al., 1983, *EMBO J.* 2:1791), in which the antibody coding sequence may be ligated individually into the vector in frame with the lac Z coding region so that a fusion protein is produced; pIN vectors (Inouye & Inouye, 1985, *Nucleic Acids Res.* 13:3101-3109; Van Heeke & Schuster, 1989, *J. Biol. Chem.* 24:5503-5509); and the like. The pGEX vectors may also be used to express foreign polypeptides as fusion proteins with glutathione S-transferase (GST). In general, such fusion proteins are soluble and can easily be purified from lysed cells by adsorption and binding to a matrix glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter). In mammalian host cells, a number of viral-based expression systems (e.g. an adenovirus expression system) may be utilized.

As discussed above, a host cell strain may be chosen which modulates the expression of the inserted sequences, or modifies and processes the gene product in the specific fashion desired. Such modifications (e.g. glycosylation) and processing (e.g. cleavage) of protein products may be important for the function of the protein.

For long-term, high-yield production of recombinant antibodies, stable expression is preferred. For example, cell lines that stably express an antibody of interest can be produced by transfecting the cells with an expression vector comprising the nucleotide sequence of the antibody and the nucleotide sequence of a selectable (e.g. neomycin or hygromycin), and selecting for expression of the selectable marker. Such engineered cell lines may be particularly useful in screening and evaluation of compounds that interact directly or indirectly with the antibody molecule.

The expression levels of the antibody molecule can be increased by vector amplification (for a review, see Bebbington and Hentschel, The use of vectors based on gene amplification for the expression of cloned genes in mammalian cells in DNA cloning, Vol. 3. (Academic Press, New York, 1987). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., 1983, *Mol. Cell. Biol.* 3:257).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes both heavy and light chain polypeptides. In such situations, the light chain should be placed before the heavy chain to avoid an excess of toxic free heavy chain (Proudfoot, 1986, *Nature* 322:52; Kohler, 1980, *Proc. Natl. Acad. Sci. USA* 77:2197). The coding sequences for the heavy and light chains may comprise cDNA or genomic DNA.

Once the antibody molecule of the invention has been recombinantly expressed, it may be purified by any method known in the art for purification of an antibody molecule, for example, by chromatography (e.g. ion exchange chromatography, affinity chromatography such as with protein A or specific antigen, and sizing column chromatography), centrifugation, differential solubility, or by any other standard technique for the purification of proteins.

Alternatively, any fusion protein may be readily purified by utilizing an antibody specific for the fusion protein being expressed. For example, a system described by Janknecht et al. allows for the ready purification of non-denatured fusion proteins expressed in human cell lines (Janknecht et al., 1991, Proc. Natl. Acad. Sci. USA 88:8972-897). In this system, the gene of interest is subcloned into a vaccinia recombination plasmid such that the open reading frame of the gene is translationally fused to an amino-terminal tag consisting of six histidine residues. The tag serves as a matrix binding domain for the fusion protein. Extracts from cells infected with recombinant vaccinia virus are loaded onto $Ni^{2+}$ nitriloacetic acid-agarose columns and histidine-tagged proteins are selectively eluted with imidazole-containing buffers.

The antibodies that are generated by these methods may then be selected by first screening for affinity and specificity with the purified polypeptide of interest and, if required, comparing the results to the affinity and specificity of the antibodies with polypeptides that are desired to be excluded from binding. The screening procedure can involve immobilization of the purified polypeptides in separate wells of microtiter plates. The solution containing a potential antibody or groups of antibodies is then placed into the respective microtiter wells and incubated for about 30 min to 2 h. The microtiter wells are then washed and a labeled secondary antibody (for example, an anti-mouse antibody conjugated to alkaline phosphatase if the raised antibodies are mouse antibodies) is added to the wells and incubated for about 30 min and then washed. Substrate is added to the wells and a color reaction will appear where antibody to the immobilized polypeptide(s) is present.

The antibodies so identified may then be further analyzed for affinity and specificity in the assay design selected. In the development of immunoassays for a target protein, the purified target protein acts as a standard with which to judge the sensitivity and specificity of the immunoassay using the antibodies that have been selected. Because the binding affinity of various antibodies may differ; certain antibody pairs (e.g. in sandwich assays) may interfere with one another sterically, etc., assay performance of an antibody may be a more important measure than absolute affinity and specificity of an antibody.

Those skilled in the art will recognize that many approaches can be taken in producing antibodies or binding fragments and screening and selecting for affinity and specificity for the various polypeptides, but these approaches do not change the scope of the invention.

For therapeutic applications, antibodies (particularly monoclonal antibodies) may suitably be human or humanized animal (e.g. mouse) antibodies Animal antibodies may be raised in animals using the human protein (e.g. BST1) as immunogen. Humanisation typically involves grafting CDRs identified thereby into human framework regions. Normally some subsequent retromutation to optimize the conformation of chains is required. Such processes are known to persons skilled in the art.

Expression of Affibodies

The construction of affibodies has been described elsewhere (Ronnmark J, Gronlund H, Uhlen, M., Nygren P. A, Human immunoglobulin A (IgA)-specific ligands from combinatorial engineering of protein A, 2002, *Eur. J. Biochem.* 269, 2647-2655.), including the construction of Affibody phage display libraries (Nord, K., Nilsson, J., Nilsson, B., Uhlen, M. & Nygren, P. A, A combinatorial library of an a-helical bacterial receptor domain, 1995, *Protein Eng.* 8, 601-608. Nord, K., Gunneriusson, E., Ringdahl, J., Stahl, S., Uhlen, M. & Nygren, P. A, Binding proteins selected from combinatorial libraries of an a-helical bacterial receptor domain, 1997, *Nat. Biotechnol.* 15, 772-777.)

The biosensor analyses to investigate the optimal Affibody variants using biosensor binding studies has also been described elsewhere (Ronnmark J, Gronlund H, Uhlen, M., Nygren P. A, Human immunoglobulin A (IgA)-specific ligands from combinatorial engineering of protein A, 2002, *Eur. J. Biochem.* 269, 2647-2655.).

Affinity Reagent Modifications

In a preferred embodiment, anti-BST1 affinity reagents such as antibodies or fragments thereof are conjugated to a diagnostic moiety (such as a detectable label) or a therapeutic moiety. The antibodies can be used for diagnosis or to determine the efficacy of a given treatment regimen. Detection can be facilitated by coupling the antibody to a detectable substance (label). Examples of detectable substances include various enzymes, prosthetic groups, fluorescent materials, luminescent materials, bioluminescent materials, radioactive nuclides, positron emitting metals (for use in positron emission tomography), and nonradioactive paramagnetic metal ions. See generally U.S. Pat. No. 4,741,900 for metal ions which can be conjugated to antibodies for use as diagnostics according to the present invention. Suitable enzymes include horseradish peroxidase, alkaline phosphatase, beta-galactosidase, or acetylcholinesterase; suitable prosthetic groups include streptavidin, avidin and biotin; suitable fluorescent materials include umbelliferone, fluorescein, fluorescein isothiocyanate, rhodamine, dichlorotriazinylamine fluorescein, dansyl chloride and phycoerythrin; suitable luminescent materials include luminol; suitable bioluminescent materials include luciferase, luciferin, and aequorin; and suitable radioactive nuclides include $^{125}I$, $^{131}I$, $^{111}In$ and $^{99}Tc$. $^{68}Ga$ may also be employed.

As indicated above affinity reagents, such as antibodies for use in the invention, may be conjugated to a therapeutic moiety, such as a cytotoxin, a drug (e.g., an immunosuppressant) or a radiotoxin. Such conjugates are referred to herein as "immunoconjugates". Immunoconjugates that include one or more cytotoxins are referred to as "immunotoxins". A cytotoxin or cytotoxic agent includes any agent that is detrimental to (e.g., kills) cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents also include, for example, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

Other preferred examples of therapeutic cytotoxins that can be conjugated to an antibody of the invention include duocarmycins, calicheamicins, maytansines and auristatins, and derivatives thereof. An example of a calicheamicin antibody conjugate is commercially available (Mylotarg®; American Home Products).

Cytotoxins can be conjugated to antibodies of the invention using linker technology available in the art. Examples of linker types that have been used to conjugate a cytotoxin to an antibody include, but are not limited to, hydrazones, thioethers, esters, disulfides and peptide-containing linkers. A linker can be chosen that is, for example, susceptible to cleavage by low pH within the lysosomal compartment or susceptible to cleavage by proteases, such as proteases preferentially expressed in tumor tissue such as cathepsins (e.g., cathepsins B, C, D).

Examples of cytotoxins are described, for example, in U.S. Pat. Nos. 6,989,452, 7,087,600, and 7,129,261, and in PCT Application Nos. PCT/US2002/17210, PCT/US2005/017804, PCT/US2006/37793, PCT/US2006/060050, PCT/US2006/060711, WO2006/110476, and in U.S. Patent Application No. 60/891,028, all of which are incorporated herein by reference in their entirety. For further discussion of types of cytotoxins, linkers and methods for conjugating therapeutic agents to antibodies, see also Saito, G. et al. (2003) *Adv. Drug Deliv. Rev.* 55:199-215; Trail, P. A. et al. (2003) *Cancer Immunol. Immunother.* 52:328-337; Payne, G. (2003) *Cancer Cell* 3:207-212; Allen, T. M. (2002) *Nat. Rev. Cancer* 2:750-763; Pastan, I. and Kreitman, R. J. (2002) *Curr. Opin. Investig. Drugs* 3:1089-1091; Senter, P. D. and Springer, C. J. (2001) *Adv. Drug Deliv. Rev.* 53:247-264.

Affinity reagents can also be conjugated to a radioactive isotope to generate cytotoxic radiopharmaceuticals, also referred to as radioimmunoconjugates. Examples of radioactive isotopes that can be conjugated to antibodies for use diagnostically or therapeutically include, but are not limited to, iodine131, indium111, yttrium90 and lutetium177. Method for preparing radioimmunoconjugates are established in the art. Examples of radioimmunoconjugates are commercially available, including Zevalin® (IDEC Pharmaceuticals) and Bexxar® (Corixa Pharmaceuticals), and similar methods can be used to prepare radioimmunoconjugates using the antibodies of the invention.

The conjugates can be used to modify a given biological response, and the drug moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, pseudomonas exotoxin, or diphtheria toxin; a protein such as tumor necrosis factor or interferon-γ; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors. Senter P. D. (2009) *Curr. Opin. Chem. Biol.* 13(3):235-244; Kovtun et al. (2010) *Cancer Res.* 70(6): 2528-2537.

Techniques for conjugating such therapeutic moieties to antibodies are well known, see, e.g., Amon et al., "Monoclonal Antibodies For Immunotargeting Of Drugs In Cancer Therapy," in *Monoclonal Antibodies And Cancer Therapy*, Reisfeld et al. (eds.), pp. 243-56 (Alan R. Liss, Inc. 1985); Hellstrom et al., "Antibodies For Drug Delivery," in *Controlled Drug Delivery* (2nd Ed.), Robinson et al. (eds.), pp. 623-53 (Marcel Dekker, Inc. 1987); Thorpe, "Antibody Carriers Of Cytotoxic Agents In Cancer Therapy: A Review," in *Monoclonal Antibodies '84: Biological And Clinical Applications*, Pinchera et al. (eds.), pp. 475-506 (1985); "Analysis, Results, And Future Prospective Of The Therapeutic Use Of Radiolabeled Antibody In Cancer Therapy," in *Monoclonal Antibodies For Cancer Detection And Therapy*, Baldwin et al. (eds.), pp. 303-16 (Academic Press 1985), and Thorpe et al., *Immunol. Rev.*, 62:119-58 (1982).

Alternatively, an antibody can be conjugated to a second antibody to form an antibody heteroconjugate as described by Segal in U.S. Pat. No. 4,676,980.

An antibody with or without a therapeutic moiety conjugated to it can be used as a therapeutic that is administered alone or in combination with cytotoxic factor(s) and/or cytokine(s).

The invention also provides for fully human, or humanised antibodies that induce antibody-directed cell-mediated cytotoxicity (ADCC). A fully human antibody is one in which the protein sequences are encoded by naturally occurring human immunoglobulin sequences, either from isolated antibody-producing human B-lymphocytes, or from transgenic murine B-lymphocytes of mice in which the murine immunoglobulin coding chromosomal regions have been replaced by orthologous human sequences. Transgenic antibodies of the latter type include, but are not restricted to, HuMab (Medarex, Inc, CA) and XenoMouse (Abgenix Inc., CA). A humanised antibody is one in which the constant region of a non-human antibody molecule of appropriate antigen specificity, is replaced by the constant region of a human antibody, preferably of the IgG subtype, with appropriate effector functions (Morrison et al., 1984, *Proc. Natl. Acad. Sci.* 81:851-855; Neuberger et al., 1984, *Nature* 312: 604-608; Takeda et al., 1985, *Nature* 314:452-454). Appropriate effector functions include ADCC, which is a natural process by which fully-human antibodies or humanized antibodies, when bound to targets on the surface of cancer cells, switch on the cell killing properties of lymphocytes that are part of the normal immune system. These active lymphocytes, called Natural Killer (NK) cells, use a cytotoxic process to destroy living cells to which the antibodies are bound. ADCC activity may be detected and quantified by measuring release of Europium ($Eu^{3+}$) from $Eu^{3+}$ labelled, living cells in the presence of an antigen-specific antibody and peripheral blood mononuclear cells extracted from an immunocompetent, living human subject. The ADCC process is described in detail in Janeway Jr. C. A. et al., *Immunobiology*, 5th ed., 2001, Garland Publishing, ISBN 0-8153-3642-X; Pier G. B. et al., *Immunology, Infection, and Immunity*, 2004, p 246-5; Albanell J. et al., *Advances in Experimental Medicine and Biology*, 2003, 532:p 2153-68 and Weng, W.-K. et al., *Journal of Clinical Oncology*, 2003, 21:p 3940-3947. Suitable methods for the detection and quantification of ADCC can be found in Blomberg et al., *Journal of Immunological Methods*. 1986, 86:p 225-9; Blomberg et al., *Journal of Immunological Methods*. 1986, 21; 92:p 117-23 and Patel & Boyd, *Journal of Immunological Methods*. 1995, 184:p 29-38.

ADCC typically involves activation of NK cells and is dependent on the recognition of antibody-coated cells by Fc receptors on the surface of the NK cell. The Fc receptors recognize the Fc (crystalline) portion of antibodies such as IgG, bound specifically to the surface of a target cell. The Fc receptor that triggers activation of the NK cell is called CD16 or FcγRIIIa. Once the FcγRIIIa receptor is bound to the IgG Fc, the NK cell releases cytokines such as IFN-γ, and cytotoxic granules containing perforin and granzymes that enter the target cell and promote cell death by triggering apoptosis.

The induction of antibody-dependent cellular cytotoxicity (ADCC) by an antibody can be enhanced by modifications that alter interactions between the antibody constant region (Fc) and various receptors that are present on the surface of cells of the immune system. Such modifications include the reduction or absence of alpha1,6-linked fucose moieties in the complex oligosaccharide chains that are normally added to the Fc of antibodies during natural or recombinant synthesis in mammalian cells. In a preferred embodiment, non-fucosylated anti-BST1 affinity reagents such as antibodies or fragments thereof are produced for the purpose of enhancing their ability to induce the ADCC response.

Techniques for reducing or ablating alpha 1,6-linked fucose moieties in the oligosaccharide chains of the Fc are well established. In one example, the recombinant antibody is synthesized in a cell line that is impaired in its ability to add fucose in an alpha 1,6 linkage to the innermost N-acetylglucosamine of the N-linked biantennary complex-type Fc oligosaccharides. Such cell lines include, but are not limited to, the rat hybridoma YB2/0, which expresses a reduced level of the alpha 1,6-fucosyltransferase gene, FUT8. Preferably, the antibody is synthesized in a cell line that is incapable of adding alpha 1,6-linked fucosyl moieties to complex oligosaccharide chains, due to the deletion of both copies of the FUT8 gene. Such cell lines include, but are not limited to, FUT8−/− CHO/DG44 cell lines. Techniques for synthesizing partially fucosylated, or non-fucosylated antibodies and affinity reagents are described in Shinkawa et al., *J. Biol. Chem.* 278:3466-34735 (2003); Yamane-Ohnuki et al., *Biotechnology and Bioengineering* 87: 614-22 (2004) and in WO00/61739 A1, WO02/31140 A1 and WO03/085107 A1. In a second example, the fucosylation of a recombinant antibody is reduced or abolished by synthesis in a cell line that has been genetically engineered to overexpress a glycoprotein-modifying glycosyl transferase at a level that maximizes the production of complex N-linked oligosaccharides carrying bisecting N-acetylglucosamine. For example, the antibody is synthesized in a Chinese Hamster Ovary cell line expressing the enzyme N-acetyl glucosamine transferase III (GnT III). Cell lines stably transfected with suitable glycoprotein-modifying glycosyl transferases, and methods of synthesizing antibodies using these cells are described in WO99/54342.

A non-fucosylated antibody or affinity reagent can be used as a therapeutic that is administered alone or in combination with cytotoxic factor(s) and/or cytokine(s).

In a further modification, the amino acid sequences of the antibody Fc are altered in a way that enhances ADCC activation, without affecting ligand affinity. Examples of such modifications are described in Lazar et al., Proceedings of the National Academy of Sciences 2006, 103: p 4005-4010; WO03/074679 and WO2007/039818. In these examples, substitution of amino acids in the antibody Fc, such as aspartate for serine at position 239, and isoleucine for glutamate at position 332, altered the binding affinity of an antibody for Fc receptors, leading to an increase in ADCC activation.

An antibody reagent with enhanced ADCC activation due to amino acid substitutions can be used as a therapeutic that is administered alone or in combination with cytotoxic factor(s) and/or cytokine(s).

The invention also provides for bispecific molecules comprising at least one first binding specificity for a first target epitope (i.e. BST1) and a second binding specificity for a second target epitope. The second target epitope maybe present on the same target protein as that bound by the first binding specificity; or the second target epitope may be present of a different target protein to that bound by the first protein to that bound by the first binding specificity. The second target epitope may be present on the same cell as the first target epitope (i.e. BST1); or the second target epitope may be present on a target which is not displayed by the cell which displays the first target epitope. As used herein, the term 'binding specificity' refers to a moiety comprising at least one antibody variable domain.

These bispecific molecules target BST1 expressing cells to CD3 or CD5 expressing effector cells (e.g. CD3 or CD5 expressing cytotoxic T cells) and trigger CD3 or CD5-mediated effector cell activities, such as T cell clonal expansion and T cell cytotoxicity. The bispecific antibodies of the invention may have a total of either two or three antibody variable domains, wherein first portion of the bispecific antibody is capable of recruiting the activity of a human immune effector cell by specifically binding to an effector antigen located on the human immune effector cell, in which the effector antigen is the human CD3 or CD5 antigen, said first portion consisting of one antibody variable domain, and a second portion of the bispecific antibody is capable of specifically binding to a target antigen other than the effector antigen e.g. BST1, said target antigen being located on a target cell other than said human immune effector cell, and said second portion comprising one or two antibody variable domains.

Diagnosis of Cancer Including the Diseases of the Invention

In accordance with the present invention, test samples of e.g. myeloid, breast, colorectal, kidney, lung or pancreatic tissue, serum, plasma or urine obtained from a subject suspected of having or known to have the diseases of the invention can be used for diagnosis or monitoring. In one embodiment, a change in the abundance of BST1 in a test sample relative to a control sample (from a subject or subjects free from the diseases of the invention) or a previously determined reference range indicates the presence of the diseases of the invention. In another embodiment, the relative abundance of BST1 in a test sample compared to a control sample or a previously determined reference range indicates a subtype of the diseases of the invention (e.g. inflammatory breast cancer, familial or sporadic colorectal cancer, renal cell carcinoma, squamous cell lung carcinoma, small cell carcinoma or endocrine tumours of the pancreas). In yet another embodiment, the relative abundance of BST1 in a test sample relative to a control sample or a previously determined reference range indicates the degree or severity of the diseases of the invention (e.g. the likelihood for metastasis). In any of the aforesaid methods, detection of BST1 may optionally be combined with detection of one or more of additional biomarkers for the diseases of the invention. Any suitable method in the art can be employed to measure the level of BST1, including but not limited to the Preferred Technologies described herein, kinase assays, immunoassays to detect and/or visualize the BST1 (e.g. Western blot, immunoprecipitation followed by sodium dodecyl sulfate polyacrylamide gel electrophoresis, immunocytochemistry, etc.). In a further embodiment, a change in the abundance of mRNA encoding BST1 in a test sample relative to a control sample or a previously determined reference range indicates the presence of the diseases of the invention. Any suitable hybridization assay can be used to detect BST1 expression by detecting and/or visualizing mRNA encoding the BST1 (e.g. Northern assays, dot blots, in situ hybridization, etc.).

In another embodiment of the invention, labeled antibodies (or other affinity reagents), derivatives and analogs thereof, which specifically bind to BST1 can be used for diagnostic purposes to detect, diagnose, or monitor the diseases of the invention. Preferably, the diseases of the invention are detected in an animal, more preferably in a mammal and most preferably in a human.

Screening Assays

The invention provides methods for identifying agents (e.g. candidate compounds or test compounds) that bind to BST1 or have a stimulatory or inhibitory effect on the expression or activity of BST1. The invention also provides methods of identifying agents, candidate compounds or test compounds that bind to a BST1-related polypeptide or a BST1 fusion protein or have a stimulatory or inhibitory effect on the expression or activity of a BST1-related polypeptide or a BST1 fusion protein. Examples of agents, candidate compounds or test compounds include, but are not limited to, nucleic acids (e.g. DNA and RNA), carbohydrates, lipids, proteins, peptides, peptidomimetics, small molecules and other drugs. Agents can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam, 1997, Anticancer Drug Des. 12:145; U.S. Pat. Nos. 5,738,996; and 5,807,683, each of which is incorporated herein in its entirety by reference).

Examples of methods for the synthesis of molecular libraries can be found in the art, for example in: DeWitt et al., 1993, *Proc. Natl. Acad. Sci. USA* 90:6909; Erb et al., 1994, *Proc. Natl. Acad. Sci. USA* 91:11422; Zuckermann et al., 1994, *J. Med. Chem.* 37:2678; Cho et al., 1993, *Science* 261:1303; Carrell et al., 1994, *Angew. Chem. Int. Ed. Engl.* 33:2059; Carell et al., 1994, *Angew. Chem. Int. Ed. Engl.* 33:2061; and Gallop et al., 1994, *J. Med. Chem.* 37:1233, each of which is incorporated herein in its entirety by reference.

Libraries of compounds may be presented, e.g. presented in solution (e.g. Houghten, 1992, *BioTechniques* 13:412-421), or on beads (Lam, 1991, *Nature* 354:82-84), chips (Fodor, 1993, *Nature* 364:555-556), bacteria (U.S. Pat. No. 5,223,409), spores (U.S. Pat. Nos. 5,571,698; 5,403,484; and 5,223,409), plasmids (Cull et al., 1992, *Proc. Natl. Acad. Sci. USA* 89:1865-1869) or phage (Scott and Smith, 1990, *Science* 249:386-390; Devlin, 1990, *Science* 249:404-406; Cwirla et al., 1990, *Proc. Natl. Acad. Sci. USA* 87:6378-6382; and Felici, 1991, *J. Mol. Biol.* 222:301-310), each of which is incorporated herein in its entirety by reference.

In one embodiment, agents that interact with (i.e. bind to) BST1, a BST1 fragment (e.g. a functionally active fragment), a BST1-related polypeptide, a fragment of a BST1-related polypeptide, or a BST1 fusion protein are identified in a cell-based assay system. In accordance with this embodiment, cells expressing BST1, a fragment of a BST1, a BST1-related polypeptide, a fragment of the BST1-related polypeptide, or a BST1 fusion protein are contacted with a candidate compound or a control compound and the ability of the candidate compound to interact with the BST1 is determined. If desired, this assay may be used to screen a plurality (e.g. a library) of candidate compounds. The cell, for example, can be of prokaryotic origin (e.g. *E. coli*) or eukaryotic origin (e.g. yeast or mammalian). Further, the cells can express BST1, a fragment of BST1, a BST1-related polypeptide, a fragment of the BST1-related polypeptide, or a BST1 fusion protein endogenously or be genetically engineered to express BST1, a fragment of BST1, a BST1-related polypeptide, a fragment of the BST1-related polypeptide, or a BST1 fusion protein. In certain instances, BST1, a fragment of BST1, a BST1-related polypeptide, a fragment of the BST1-related polypeptide, or a BST1 fusion protein or the candidate compound is labeled, for example with a radioactive label (such as $^{32}P$, $^{35}S$, and $^{125}I$) or a fluorescent label (such as fluorescein isothiocyanate, rhodamine, phycoerythrin, phycocyanin, allophycocyanin, o-phthaldehyde or fluorescamine) to enable detection of an interaction between BST1 and a candidate compound. The ability of the candidate compound to interact directly or indirectly with BST1, a fragment of a BST1, a BST1-related polypeptide, a fragment of a BST1-related polypeptide, or a BST1 fusion protein can be determined by methods known to those of skill in the art. For example, the interaction between a candidate compound and BST1, a BST1-related polypeptide, a fragment of a BST1-related polypeptide, or a BST1 fusion protein can be determined by flow cytometry, a scintillation assay, immunoprecipitation or western blot analysis.

In another embodiment, agents that interact with (i.e. bind to) BST1, a BST1 fragment (e.g. a functionally active fragment), a BST1-related polypeptide, a fragment of a BST1-related polypeptide, or a BST1 fusion protein are identified in a cell-free assay system. In accordance with this embodiment, native or recombinant BST1 or a fragment thereof, or a native or recombinant BST1-related polypeptide or fragment thereof, or a BST1-fusion protein or fragment thereof, is contacted with a candidate compound or a control compound and the ability of the candidate compound to interact with BST1 or BST1-related polypeptide, or BST1 fusion protein is determined. If desired, this assay may be used to screen a plurality (e.g. a library) of candidate compounds. Preferably, BST1, a BST1 fragment, a BST1-related polypeptide, a fragment of a BST1-related polypeptide, or a BST1-fusion protein is first immobilized, by, for example, contacting BST1, a BST1 fragment, a BST1-related polypeptide, a fragment of a BST1-related polypeptide, or a BST1 fusion protein with an immobilized antibody (or other affinity reagent) which specifically recognizes and binds it, or by contacting a purified preparation of BST1, a BST1 fragment, a BST1-related polypeptide, fragment of a BST1-related polypeptide, or a BST1 fusion protein with a surface designed to bind proteins. BST1, a BST1 fragment, a BST1-related polypeptide, a fragment of a BST1-related polypeptide, or a BST1 fusion protein may be partially or completely purified (e.g. partially or completely free of other polypeptides) or part of a cell lysate. Further, BST1, a BST1 fragment, a BST1-related polypeptide, or a fragment of a BST1-related polypeptide may be a fusion protein comprising BST1 or a biologically active portion thereof, or BST1-related polypeptide and a domain such as glutathionine-S-transferase. Alternatively, BST1, a BST1 fragment, a BST1-related polypeptide, a fragment of a BST1-related polypeptide or a BST1 fusion protein can be biotinylated using techniques well known to those of skill in the art (e.g. biotinylation kit, Pierce Chemicals; Rockford, Ill.). The ability of the candidate compound to interact with BST1, a BST1 fragment, a BST1-related polypeptide, a fragment of a BST1-related polypeptide, or a BST1 fusion protein can be determined by methods known to those of skill in the art.

In another embodiment, a cell-based assay system is used to identify agents that bind to or modulate the activity of a protein, such as an enzyme, or a biologically active portion thereof, which is responsible for the production or degradation of BST1 or is responsible for the post-translational modification of BST1. In a primary screen, a plurality (e.g. a library) of compounds are contacted with cells that naturally or recombinantly express: (i) BST1, an isoform of BST1, a BST1 homolog, a BST1-related polypeptide, a BST1 fusion protein, or a biologically active fragment of any of the foregoing; and (ii) a protein that is responsible for processing of BST1, a BST1 isoform, a BST1 homolog, a BST1-related polypeptide, a BST1 fusion protein, or a fragment in order to identify compounds that modulate the production, degradation, or post-translational modification of BST1, a BST1 isoform, a BST1 homolog, a BST1-related polypeptide, a BST1 fusion protein or fragment. If desired, compounds identified in the primary screen can then be assayed in a secondary screen against cells naturally or recombinantly expressing BST1. The ability of the candidate compound to modulate the production, degradation or post-translational modification of BST1, isoform, homolog, BST1-related polypeptide, or BST1 fusion protein can be determined by methods known to those of skill in the art, including without limitation, flow cytometry, a scintillation assay, immunoprecipitation and western blot analysis.

In another embodiment, agents that competitively interact with (i.e. bind to) BST1, a BST1 fragment, a BST1-related polypeptide, a fragment of a BST1-related polypeptide, or a BST1 fusion protein are identified in a competitive binding assay. In accordance with this embodiment, cells expressing BST1, a BST1 fragment, a BST1-related polypeptide, a fragment of a BST1-related polypeptide, or a BST1 fusion protein are contacted with a candidate compound and a compound known to interact with BST1, a BST1 fragment, a BST1-related polypeptide, a fragment of a BST1-related polypeptide or a BST1 fusion protein; the ability of the candidate compound to preferentially interact with BST1, a BST1 fragment, a BST1-related polypeptide, a fragment of a BST1-related polypeptide, or a BST1 fusion protein is then determined. Alternatively, agents that preferentially interact with (i.e. bind to) BST1, a BST1 fragment, a BST1-related polypeptide or fragment of a BST1-related polypeptide are identified in a cell-free assay system by contacting BST1, a BST1 fragment, a BST1-related polypeptide, a fragment of a BST1-related polypeptide, or a BST1 fusion protein with a candidate compound and a compound known to interact with BST1, a BST1-related polypeptide or a BST1 fusion protein. As stated above, the ability of the candidate compound to interact with BST1, a BST1 fragment, a BST1-related polypeptide, a fragment of a BST1-related polypeptide, or a BST1 fusion protein can be determined by methods known to those of skill in the art. These assays, whether cell-based or cell-free, can be used to screen a plurality (e.g. a library) of candidate compounds.

In another embodiment, agents that modulate (i.e. upregulate or downregulate) the expression or activity of BST1 or a BST1-related polypeptide are identified by contacting cells (e.g. cells of prokaryotic origin or eukaryotic origin) expressing BST1 or a BST1-related polypeptide with a candidate compound or a control compound (e.g. phosphate buffered saline (PBS)) and determining the expression of BST1, BST1-related polypeptide, or BST1 fusion protein, mRNA encoding BST1, or mRNA encoding the BST1-related polypeptide. The level of expression of BST1, BST1-related polypeptide, mRNA encoding BST1, or mRNA encoding the BST1-related polypeptide in the presence of the candidate compound is compared to the level of expression of BST1, BST1-related polypeptide, mRNA encoding BST1, or mRNA encoding the BST1-related polypeptide in the absence of the candidate compound (e.g. in the presence of a control compound). The candidate compound can then be identified as a modulator of the expression of BST1, or the BST1-related polypeptide based on this comparison. For example, when expression of BST1 or mRNA is significantly greater in the presence of the candidate compound than in its absence, the candidate compound is identified as a stimulator of expression of BST1 or mRNA. Alternatively, when expression of BST1 or mRNA is significantly less in the presence of the candidate compound than in its absence, the candidate compound is identified as an inhibitor of the expression of BST1 or mRNA. The level of expression of BST1 or the mRNA that encodes it can be determined by methods known to those of skill in the art. For example, mRNA expression can be assessed by Northern blot analysis or RT-PCR, and protein levels can be assessed by western blot analysis.

In another embodiment, agents that modulate the activity of BST1 or a BST1-related polypeptide are identified by contacting a preparation containing BST1 or BST1-related polypeptide or cells (e.g. prokaryotic or eukaryotic cells) expressing BST1 or BST1-related polypeptide with a test compound or a control compound and determining the ability of the test compound to modulate (e.g. stimulate or inhibit) the activity of BST1 or BST1-related polypeptide. The activity of BST1 or a BST1-related polypeptide can be assessed by detecting induction of a cellular signal transduction pathway of BST1 or BST1-related polypeptide (e.g. intracellular $Ca^{2+}$, diacylglycerol, IP3, etc.), detecting catalytic or enzymatic activity of the target on a suitable substrate, detecting the induction of a reporter gene (e.g. a regulatory element that is responsive to BST1 or a BST1-related polypeptide and is operably linked to a nucleic acid encoding a detectable marker, e.g. luciferase), or detecting a cellular response, for example, cellular differentiation, or cell proliferation. Based on the present description, techniques known to those of skill in the art can be used for measuring these activities (see, e.g. U.S. Pat. No. 5,401,639, which is incorporated herein by reference). The candidate compound can then be identified as a modulator of the activity of BST1 or a BST1-related polypeptide by comparing the effects of the candidate compound to the control compound. Suitable control compounds include phosphate buffered saline (PBS) and normal saline (NS).

In another embodiment, agents that modulate (i.e. upregulate or downregulate) the expression, activity or both the expression and activity of BST1 or a BST1-related polypeptide are identified in an animal model. Examples of suitable animals include, but are not limited to, mice, rats, rabbits, monkeys, guinea pigs, dogs and cats. Preferably, the animal used represent a model of the diseases of the invention (e.g. xenografts of breast cancer cell lines such as MCF-7 (Ozzello L, Sordat M., *Eur J Cancer.* 1980; 16:553-559) and MCF10AT (Miller et al., *J Natl Cancer Inst.* 1993; 85:1725-1732) in nude or SCID mice; xenografts of human colorectal cancer cell lines such as MDA-MB-345 in oestrogen-deprived SCID mice, Eccles et al. 1994 *Cell Biophysics* 24/25, 279; xenografts of kidney cancer cell lines such as CAKI-1 (Matthews P N, Grant A G, Hermon-Taylor J. Br J Cancer. 1984 February; 49(2): 193-198), 786-O (G. J. STREWLER et al Endocrinology Vol. 119, No. 1 303-310) and ACHN (Zeng J, Mei W, Huang H, Li X, Kong P.; J Huazhong Univ Sci Technolog Med Sci. 2002; 22(4):331-3) in nude mice; xenografts of non-small cell lung cancer cell lines such as A549 and H460 and xenografts of small cell lung cancer cell lines such as NCI-H345 or xenografts of pancreatic cancer cell lines such as MIA PaCa-2 in nude mice, Marincola et al., *J Surg Res* 1989 December; 47(6): 520-9). These can be utilized to test compounds that modulate BST1 levels, since the pathology exhibited in these models is similar to that of e.g. the diseases of the invention. In accordance with this embodiment, the test compound or a control compound is administered (e.g. orally, rectally or parenterally such as intraperitoneally or intravenously) to a suitable animal and the effect on the expression, activity or both expression and activity of BST1 or BST1-related polypeptide is determined Changes in the expression of BST1 or a BST1-related polypeptide can be assessed by the methods outlined above.

In yet another embodiment, BST1 or a BST1-related polypeptide is used as a "bait protein" in a two-hybrid assay or three hybrid assay to identify other proteins that bind to or interact with BST1 or a BST1-related polypeptide (see, e.g. U.S. Pat. No. 5,283,317; Zervos et al. (1993) *Cell* 72:223-232; Madura et al. (1993) *J. Biol. Chem.* 268:12046-12054; Bartel et al. (1993) *BioTechniques* 14:920-924; Iwabuchi et al. (1993) *Oncogene* 8:1693-1696; and PCT Publication No. WO 94/10300). As those skilled in the art will appreciate, such binding proteins are also likely to be involved in the propagation of signals by BST1 as, for example, upstream or downstream elements of a signaling pathway involving BST1.

This invention further provides novel agents identified by the above-described screening assays and uses thereof for treatments as described herein. In addition, the invention also provides the use of an agent which interacts with, or modulates the activity of, BST1 in the manufacture of a medicament for the treatment of the diseases of the invention.

Therapeutic Use of BST1

The invention provides for treatment or prevention of various diseases and disorders by administration of a therapeutic compound. Such compounds include but are not limited to: BST1, BST1 analogs, BST1-related polypeptides and derivatives (including fragments) thereof; antibodies (or other affinity reagents) to the foregoing; nucleic acids encoding BST1, BST1 analogs, BST1-related polypeptides and fragments thereof; antisense nucleic acids to a gene encoding BST1 or a BST1-related polypeptide; and modulator (e.g. agonists and antagonists) of a gene encoding BST1 or a BST1-related polypeptide. An important feature of the present invention is the identification of genes encoding the lon-variant of BST1 involved in cancers such as the diseases of the invention. The diseases of the invention, for example, can be treated (e.g. to ameliorate symptoms or to retard onset or progression) or prevented by administration of a therapeutic compound that reduces function or expression of BST1 in the serum or tissue of subjects having the diseases of the invention.

In one embodiment, one or more antibodies (or other affinity reagents) each specifically binding to BST1 are administered alone or in combination with one or more additional therapeutic compounds or treatments.

A biological product such as an antibody (or other affinity reagent) is allogeneic to the subject to which it is administered. In one embodiment, a human BST1 or a human BST1-related polypeptide, a nucleotide sequence encoding a human BST1 or a human BST1-related polypeptide, or an antibody (or other affinity reagent) to a human BST1 or a human BST1-related polypeptide, is administered to a human subject for therapy (e.g. to ameliorate symptoms or to retard onset or progression) or prophylaxis.

Without being limited by theory, it is conceived that the therapeutic activity of antibodies (or other affinity reagents) which specifically bind to BST1 may be achieved through the phenomenon of Antibody-Dependent Cell-mediated Cytotoxicity (ADCC) (see e.g. Janeway Jr. C. A. et al., *Immunobiology*, 5th ed., 2001, Garland Publishing, ISBN 0-8153-3642-X; Pier G. B. et al., *Immunology, Infection, and Immunity*, 2004, p 246-5; Albanell J. et al., *Advances in Experimental Medicine and Biology*, 2003, 532:p 2153-68 and Weng, W.-K. et al., *Journal of Clinical Oncology*, 2003, 21:p 3940-3947).

Treatment and Prevention of the Diseases of the Invention

The diseases of the invention, for example, is treated or prevented by administration to a subject suspected of having or known to have the diseases of the invention or to be at risk of developing the diseases of the invention of a compound that modulates (i.e. increases or decreases) the level or activity (i.e. function) of BST1 that is differentially present in the serum or tissue of subjects having the diseases of the invention compared with serum or tissue of subjects free from the diseases of the invention. In one embodiment, the diseases of the invention is treated or prevented by administering to a subject suspected of having or known to have the diseases of the invention or to be at risk of developing the diseases of the invention a compound that upregulates (i.e. increases) the level or activity (i.e. function) of BST1 that are decreased in the serum or tissue of subjects having the diseases of the invention. Examples of such a compound include, but are not limited to, BST1 antisense oligonucleotides, ribozymes, antibodies (or other affinity reagents) directed against BST1, and compounds that inhibit the enzymatic activity of BST1. Other useful compounds e.g. BST1 antagonists and small molecule BST1 antagonists, can be identified using in vitro assays.

Cancer e.g. the diseases of the invention is also treated or prevented by administration to a subject suspected of having or known to have such cancer, or to be at risk of developing such cancer, of a compound that downregulates the level or activity (i.e. function) of BST1 that are increased in the serum or tissue of subjects having such cancer. Examples of such a compound include but are not limited to: BST1, BST1 fragments and BST1-related polypeptides; nucleic acids encoding BST1, a BST1 fragment and a BST1-related polypeptide (e.g. for use in gene therapy); and, for those BST1 or BST1-related polypeptides with enzymatic activity, compounds or molecules known to modulate that enzymatic activity. Other compounds that can be used, e.g. BST1 agonists, can be identified using in in vitro assays.

In another embodiment, therapy or prophylaxis is tailored to the needs of an individual subject. Thus, in specific embodiments, compounds that promote the level or function of BST1 are therapeutically or prophylactically administered to a subject suspected of having or known to have cancer e.g. the diseases of the invention, in whom the levels or functions of BST1 are absent or are decreased relative to a control or normal reference range. In further embodiments, compounds that promote the level or function of BST1 are therapeutically or prophylactically administered to a subject suspected of having or known to have cancer e.g. the diseases of the invention in whom the levels or functions of BST1 are increased relative to a control or to a reference range. In further embodiments, compounds that decrease the level or function of BST1 are therapeutically or prophylactically administered to a subject suspected of having or known to have cancer e.g. the diseases of the invention in whom the levels or functions of BST1 are increased relative to a control or to a reference range. In further embodiments, compounds that decrease the level or function of BST1 are therapeutically or prophylactically administered to a subject suspected of having or known to have cancer e.g. the diseases of the invention in whom the levels or functions of BST1 are decreased relative to a control or to a reference range. The change in BST1 function or level due to the administration of such compounds can be readily detected, e.g. by obtaining a sample (e.g. blood or urine) and assaying in vitro the levels or activities of BST1, or the levels of mRNAs encoding BST1, or any combination of the foregoing. Such assays can be performed before and after the administration of the compound as described herein.

The compounds of the invention include but are not limited to any compound, e.g. a small organic molecule, protein, peptide, antibody (or other affinity reagent), nucleic acid, etc. that restores the BST1 profile towards normal. The compounds of the invention may be given in combination with any other chemotherapy drugs.

Vaccine Therapy

Another aspect of the invention is an immunogenic composition, suitably a vaccine composition, comprising BST1 or an epitope containing fragment thereof, or nucleic acid encoding BST1 or a fragment thereof optionally together with an immunostimulant.

There is also provided a method of raising an immune response which comprises administering to a subject such compositions and a method for treating or preventing cancer e.g. the diseases of the invention which comprises administering to a subject in need thereof a therapeutically effective amount of such compositions and such compositions for use in preventing or treating the diseases of the invention.

Thus, BST1 may be useful as antigenic material, and may be used in the production of vaccines for treatment or prophylaxis of cancer, e.g. the diseases of the invention. Such material can be "antigenic" and/or "immunogenic". Generally, "antigenic" is taken to mean that the protein is capable of being used to raise antibodies (or other affinity reagents) or indeed is capable of inducing an antibody response in a subject or experimental animal. "Immunogenic" is taken to mean that the protein is capable of eliciting an immune response such as a protective immune response in a subject or experimental animal. Thus, in the latter case, the protein may be capable of not only generating an antibody response but, in addition, non-antibody based immune responses. "Immunogenic" also embraces whether the protein may elicit an immune-like response in an in-vitro setting e.g. a T-cell proliferation assay. The generation of an appropriate immune response may require the presence of one or more adjuvants and/or appropriate presentation of an antigen.

The skilled person will appreciate that homologues or derivatives of BST1 will also find use as antigenic/immunogenic material. Thus, for instance proteins which include one or more additions, deletions, substitutions or the like are encompassed by the present invention. In addition, it may be possible to replace one amino acid with another of similar "type", for instance, replacing one hydrophobic amino acid with another. One can use a program such as the CLUSTAL program to compare amino acid sequences. This program compares amino acid sequences and finds the optimal alignment by inserting spaces in either sequence as appropriate. It is possible to calculate amino acid identity or similarity (identity plus conservation of amino acid type) for an optimal alignment. A program like BLASTx will align the longest stretch of similar sequences and assign a value to the fit. It is thus possible to obtain a comparison where several regions of similarity are found, each having a different score. Both types of analysis are contemplated in the present invention.

In the case of homologues and derivatives, the degree of identity with a protein as described herein is less important than that the homologue or derivative should retain its antigenicity and/or immunogenicity. However, suitably, homologues or derivatives having at least 60% similarity (as discussed above) with the proteins or polypeptides described herein are provided, for example, homologues or derivatives having at least 70% similarity, such as at least 80% similarity are provided. Particularly, homologues or derivatives having at least 90% or even 95% similarity are provided. Suitably, homologues or derivatives have at least 60% sequence identity with the proteins or polypeptides described herein. Preferably, homologues or derivatives have at least 70% identity, more preferably at least 80% identity. Most preferably, homologues or derivatives have at least 90% or even 95% identity.

In an alternative approach, the homologues or derivatives could be fusion proteins, incorporating moieties which render purification easier, for example by effectively tagging the desired protein or polypeptide. It may be necessary to remove the "tag" or it may be the case that the fusion protein itself retains sufficient antigenicity to be useful.

It is well known that it is possible to screen an antigenic protein or polypeptide to identify epitopic regions, i.e. those regions which are responsible for the protein or polypeptide's antigenicity or immunogenicity. Methods well known to the skilled person can be used to test fragments and/or homologues and/or derivatives for antigenicity. Thus, the fragments of the present invention should include one or more such epitopic regions or be sufficiently similar to such regions to retain their antigenic/immunogenic properties. Thus, for fragments according to the present invention the degree of identity is perhaps irrelevant, since they may be 100% identical to a particular part of a protein or polypeptide, homologue or derivative as described herein. The key issue, once again, is that the fragment retains the antigenic/immunogenic properties of the protein from which it is derived.

What is important for homologues, derivatives and fragments is that they possess at least a degree of the antigenicity/immunogenicity of the protein or polypeptide from which they are derived. Thus, in an additional aspect of the invention, there is provided antigenic/or immunogenic fragments of BST1, or of homologues or derivatives thereof.

BST1, or antigenic fragments thereof, can be provided alone, as a purified or isolated preparation. They may be provided as part of a mixture with one or more other proteins of the invention, or antigenic fragments thereof. In a further aspect, therefore, the invention provides an antigen composition comprising BST1 and/or one or more antigenic fragments thereof. Such a composition can be used for the detection and/or diagnosis of cancer, e.g. the diseases of the invention.

Vaccine compositions according to the invention may be either a prophylactic or therapeutic vaccine composition.

The vaccine compositions of the invention can include one or more adjuvants (immunostimulants). Examples well-known in the art include inorganic gels, such as aluminium hydroxide, and water-in-oil emulsions, such as incomplete Freund's adjuvant. Other useful adjuvants will be well known to the skilled person.

Suitable adjuvants for use in vaccine compositions for the treatment of cancer include: 3De-O-acylated monophosphoryl lipid A (known as 3D-MPL or simply MPL see WO92/116556), a saponin, for example QS21 or QS7, and TLR4 agonists such as a CpG containing molecule, for example as disclosed in WO95/26204. The adjuvants employed may be a combination of components, for example MPL and QS21 or MPL, QS21 and a CpG containing moiety. Adjuvants may be formulated as oil-in-water emulsions or liposomal formulations. Such preparations may include other vehicles.

In another embodiment, a preparation of oligonucleotides comprising 10 or more consecutive nucleotides complementary to a nucleotide sequence encoding BST1 or a BST1 peptide fragments is used as vaccines for the treatment of cancer, e.g. the diseases of the invention. Such preparations may include adjuvants or other vehicles.

Inhibition of BST1 to Treat the Diseases of the Invention

In one embodiment of the invention, cancer, e.g. the diseases of the invention is treated or prevented by administration of a compound that antagonizes (inhibits) the level and/or function of BST1 which is elevated in the serum or tissue of subjects having such cancer as compared with serum or tissue of subjects free from such cancer.

Compounds useful for this purpose include but are not limited to anti-BST1 antibodies (or other affinity reagents, and fragments and derivatives containing the binding region thereof), BST1 antisense or ribozyme nucleic acids, and nucleic acids encoding dysfunctional BST1 that may be used to "knockout" endogenous BST1 function by homologous recombination (see, e.g. Capecchi, 1989, *Science* 244:1288-1292). Other compounds that inhibit BST1 function can be identified by use of known in vitro assays, e.g. assays for the ability of a test compound to inhibit binding of BST1 to another protein or a binding partner, or to inhibit a known BST1 function.

Such inhibition may, for example, be assayed in vitro or in cell culture, but genetic assays may also be employed. The Preferred Technologies can also be used to detect levels of BST1 before and after the administration of the compound. Suitable in vitro or in vivo assays are utilized to determine the effect of a specific compound and whether its administration is indicated for treatment of the affected tissue, as described in more detail below.

In a specific embodiment, a compound that inhibits BST1 function (activity) is administered therapeutically or prophylactically to a subject in whom an increased serum or tissue level or functional activity of BST1 (e.g. greater than the normal level or desired level) is detected as compared with serum or tissue of subjects with e.g. the diseases of the invention who do not receive treatment according to the invention or to bring the level or activity to that found in subjects free from such cancer, or a predetermined reference range. Methods standard in the art can be employed to measure the increase in BST1 level or function, as outlined above. Suitable BST1 inhibitor compositions may, for example, include small molecules, i.e. molecules of 1000 daltons or less. Such small molecules can be identified by the screening methods described herein.

Assays for Therapeutic or Prophylactic Compounds

The present invention also provides assays for use in drug discovery in order to identify or verify the efficacy of compounds for treatment or prevention of cancers expressing the extracellular domain of BST1, e.g. the diseases of the invention.

Thus there is provided a method of screening for compounds that modulate the activity of BST1, the method comprising: (a) contacting BST1 or a biologically active portion thereof with a candidate compound; and (b) determining whether activity of BST1 is thereby modulated. Such a process may comprise (a) contacting BST1 or a biologically active portion thereof with a candidate compound in a sample; and (b) comparing the activity of BST1 or a biologically active portion thereof in said sample after contact with said candidate compound with the activity of BST1 or a biologically active portion thereof in said sample before contact with said candidate compound, or with a reference level of activity.

The method of screening may be a method of screening for compounds that inhibit activity of BST1.

BST1 or a biologically active portion thereof may, for example be expressed on or by a cell. BST1 or a biologically active portion thereof may, for example, be isolated from cells which express it. BST1 or a biologically active portion thereof may, for example, be immobilised onto a solid phase.

There is also provided a method of screening for compounds that modulate the expression of BST1 or nucleic acid encoding BST1, the method comprising: (a) contacting cells expressing BST1 or nucleic acid encoding BST1 with a candidate compound; and (b) determining whether expression of BST1 or nucleic acid encoding BST1 is thereby modulated. Such a process may comprises (a) contacting cells expressing BST1 or nucleic acid encoding BST1 with a candidate compound in a sample; and (b) comparing the expression of BST1 or nucleic acid encoding BST1 by cells in said sample after contact with said candidate compound with the expression of BST1 or nucleic acid encoding BST1 of cells in said sample before contact with said candidate compound, or with a reference level of expression.

The method may be a method of screening for compounds that inhibit expression of BST1 or nucleic acid encoding BST1.

Other aspects of the invention include: a compound obtainable by an aforementioned screening method, a compound which modulates the activity or expression of BST1 or nucleic acid encoding BST1, for example a compound which inhibits the activity or expression of BST1 or nucleic acid encoding BST1.

Such a compound is provided for use in treating or preventing cancer, e.g. the diseases of the invention. There is also provided a method for treating or preventing cancer, e.g. the diseases of the invention which comprises administering to a subject in need thereof a therapeutically effective amount of such a compound.

Test compounds can be assayed for their ability to restore BST1 levels in a subject having e.g. the diseases of the invention towards levels found in subjects free from such cancers or to produce similar changes in experimental animal models of such cancers. Compounds able to restore BST1 levels in a subject having e.g. the diseases of the invention towards levels found in subjects free from such cancers or to produce similar changes in experimental animal models of such cancers can be used as lead compounds for further drug discovery, or used therapeutically. BST1 expression can be assayed by the Preferred Technologies, immunoassays, gel electrophoresis followed by visualization, detection of BST1 activity, or any other method taught herein or known to those skilled in the art. Such assays can be used to screen candidate drugs, in clinical monitoring or in drug development, where abundance of BST1 can serve as a surrogate marker for clinical disease.

In various specific embodiments, in vitro assays can be carried out with cells representative of cell types involved in a subject's disorder, to determine if a compound has a desired effect upon such cell types.

Compounds for use in therapy can be tested in suitable animal model systems prior to testing in humans, including but not limited to rats, mice, chicken, cows, monkeys, rabbits, etc. For in vivo testing, prior to administration to humans, any animal model system known in the art may be used. Examples of animal models of the diseases of the invention include, but are not limited to xenografts of breast cancer cell lines such as MCF-7 (Ozzello L, Sordat M., *Eur J Cancer.* 1980; 16:553-559) and MCF10AT (Miller et al., *J Natl Cancer Inst.* 1993; 85:1725-1732) in nude or SCID mice; xenografts of human colorectal cancer cell lines such as MDA-MB-345 in oestrogen-deprived SCID mice, Eccles et al. 1994 *Cell Biophysics* 24/25, 279; xenografts of kidney cancer cell lines such as CAKI-1 (Matthews P N, Grant A G, Hermon-Taylor J. Br J Cancer. 1984 February; 49(2): 193-198), 786-O (G. J. STREWLER et al Endocrinology Vol. 119, No. 1 303-310) and ACHN (Zeng J, Mei W, Huang H, Li X, Kong P.; J Huazhong Univ Sci Technolog Med Sci. 2002; 22(4):331-3) in nude mice; xenografts of non-small cell lung cancer cell lines such as A549 and H460 and xenografts of small cell lung cancer cell lines such as NCI-H345 or xenografts of pancreatic cancer cell lines such as MIA PaCa-2 in nude mice, Marincola et al., *J Surg Res* 1989 December; 47(6):520-9. These can be utilized to test compounds that modulate BST1 levels, since the pathology exhibited in these models is similar to that of e.g. the diseases of the invention. It is also apparent to the skilled artisan that based upon the present disclosure, transgenic animals can be produced with "knock-out" mutations of the gene or genes encoding BST1. A "knock-out" mutation of a gene is a mutation that causes the mutated gene to not be expressed, or expressed in an aberrant form or at a low level, such that the activity associated with the gene product is nearly or entirely absent. Preferably, the transgenic animal is a mammal; more preferably, the transgenic animal is a mouse.

In one embodiment, test compounds that modulate the expression of BST1 are identified in non-human animals (e.g. mice, rats, monkeys, rabbits, and guinea pigs), preferably non-human animal models for the diseases of the invention expressing BST1. In accordance with this embodiment, a test compound or a control compound is administered to the animals, and the effect of the test compound on expression of BST1 is determined. A test compound that alters the expression of BST1 can be identified by comparing the level of BST1 (or mRNA encoding the same) in an animal or group of animals treated with a test compound with the level of BST1 or mRNA in an animal or group of animals treated with a control compound. Techniques known to those of skill in the art can be used to determine the mRNA and protein levels, for example, in situ hybridization. The animals may or may not be sacrificed to assay the effects of a test compound.

In another embodiment, test compounds that modulate the activity of BST1 or a biologically active portion thereof are identified in non-human animals (e.g. mice, rats, monkeys, rabbits, and guinea pigs), preferably non-human animal models for the diseases of the invention expressing BST1. In accordance with this embodiment, a test compound or a control compound is administered to the animals, and the effect of a test compound on the activity of BST1 is determined A test compound that alters the activity of BST1 can be identified by assaying animals treated with a control compound and animals treated with the test compound. The activity of BST1 can be assessed by detecting induction of a cellular second messenger of BST1 (e.g. intracellular $Ca^{2+}$, diacylglycerol, IP3, etc.), detecting catalytic or enzymatic activity of BST1 or binding partner thereof, detecting the induction of a reporter gene (e.g. a regulatory element that is responsive to BST1 operably linked to a nucleic acid encoding a detectable marker, such as luciferase or green fluorescent protein), or detecting a cellular response (e.g. cellular differentiation or cell proliferation). Techniques known to those of skill in the art can be utilized to detect changes in the activity of BST1 (see, e.g. U.S. Pat. No. 5,401,639, which is incorporated herein by reference).

In yet another embodiment, test compounds that modulate the level or expression of BST1 are identified in human subjects having e.g. the diseases of the invention, preferably those having e.g. severe the diseases of the invention. In accordance with this embodiment, a test compound or a control compound is administered to the human subject, and the effect of a test compound on BST1 expression is determined by analyzing the expression of BST1 or the mRNA encoding the same in a biological sample (e.g. serum, plasma, or urine). A test compound that alters the expression of BST1 can be identified by comparing the level of BST1 or mRNA encoding the same in a subject or group of subjects treated with a control compound to that in a subject or group of subjects treated with a test compound. Alternatively, alterations in the expression of BST1 can be identified by comparing the level of BST1 or mRNA encoding the same in a subject or group of subjects before and after the administration of a test compound. Techniques known to those of skill in the art can be used to obtain the biological sample and analyze the mRNA or protein expression. For example, the Preferred Technologies described herein can be used to assess changes in the level of BST1.

In another embodiment, test compounds that modulate the activity of BST1 are identified in human subjects having e.g. the diseases of the invention (preferably those with e.g. severe the diseases of the invention). In this embodiment, a test compound or a control compound is administered to the human subject, and the effect of a test compound on the activity of BST1 is determined. A test compound that alters the activity of BST1 can be identified by comparing biological samples from subjects treated with a control compound to samples from subjects treated with the test compound. Alternatively, alterations in the activity of BST1 can be identified by comparing the activity of BST1 in a subject or group of subjects before and after the administration of a test compound. The activity of BST1 can be assessed by detecting in a biological sample (e.g. serum, plasma, or urine) induction of a cellular signal transduction pathway of BST1 (e.g. intracellular $Ca^{2+}$, diacylglycerol, IP3, etc.), catalytic or enzymatic activity of BST1 or a binding partner thereof, or a cellular response, for example, cellular differentiation, or cell proliferation. Techniques known to those of skill in the art can be used to detect changes in the induction of a second messenger of BST1 or changes in a cellular response. For example, RT-PCR can be used to detect changes in the induction of a cellular second messenger.

In another embodiment, a test compound that changes the level or expression of BST1 towards levels detected in control subjects (e.g. humans free from e.g. the diseases of the invention) is selected for further testing or therapeutic use. In another embodiment, a test compound that changes the activity of BST1 towards the activity found in control subjects (e.g. humans free from e.g. the diseases of the invention) is selected for further testing or therapeutic use.

In another embodiment, test compounds that reduce the severity of one or more symptoms associated with e.g. the diseases of the invention are identified in human subjects having e.g. the diseases of the invention, preferably subjects with e.g. severe the diseases of the invention. In accordance with this embodiment, a test compound or a control compound is administered to the subjects, and the effect of a test compound on one or more symptoms of e.g. the diseases of the invention is determined A test compound that reduces one or more symptoms can be identified by comparing the subjects treated with a control compound to the subjects treated with the test compound. Techniques known to physicians familiar with e.g. the diseases of the invention can be used to determine whether a test compound reduces one or more symptoms associated with e.g. the diseases of the invention. For example, a test compound that reduces tumour burden in a subject having e.g. the diseases of the invention will be beneficial for such subject.

In another embodiment, a test compound that reduces the severity of one or more symptoms associated with cancer, e.g. the diseases of the invention in a human having one of the diseases of the invention is selected for further testing or therapeutic use.

Therapeutic and Prophylactic Compositions and their Use

The invention provides methods of treatment (and prophylaxis) comprising administering to a subject an effective amount of a compound of the invention. In a particular aspect, the compound is substantially purified (e.g. substantially free from substances that limit its effect or produce undesired side-effects). The subject is for example an animal, including but not limited to animals such as cows, pigs, horses, chickens, cats, dogs, etc., and is for example a mammal, such as a human. In a specific embodiment, a non-human mammal is the subject.

Formulations and methods of administration that can be employed when the compound comprises a nucleic acid are described above; additional appropriate formulations and routes of administration are described below.

Various delivery systems are known and can be used to administer a compound of the invention, e.g. encapsulation in liposomes, microparticles, microcapsules, recombinant cells capable of expressing the compound, receptor-mediated endocytosis (see, e.g. Wu and Wu, 1987, *J. Biol. Chem.* 262:4429-4432), construction of a nucleic acid as part of a retroviral or other vector, etc. Methods of introduction can be enteral or parenteral and include but are not limited to intradermal, intramuscular, intraperitoneal, intravenous, subcutaneous, intranasal, epidural, and oral routes. The compounds may be administered by any convenient route, for example by infusion or bolus injection, by absorption through epithelial or mucocutaneous linings (e.g. oral mucosa, rectal and intestinal mucosa, etc.) and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir Pulmonary administration can also be employed, e.g. by use of an inhaler or nebulizer, and formulation with an aerosolizing agent.

In one aspect of the invention a nucleic acid employed in the invention may be delivered to the dermis, for example employing particle mediated epidermal delivery.

In a specific embodiment, it may be desirable to administer the pharmaceutical compositions of the invention locally to the area in need of treatment; this may be achieved, for example, and not by way of limitation, by local infusion during surgery, topical application, e.g. by injection, by means of a catheter, or by means of an implant, said implant being of a porous, non-porous, or gelatinous material, including membranes, such as sialastic membranes, or fibers. In one embodiment, administration can be by direct injection into e.g. myeloid, breast, colorectal, kidney, lung or pancreatic tissue or at the site (or former site) of a malignant tumor or neoplastic or pre-neoplastic tissue.

In another embodiment, the compound can be delivered in a vesicle, in particular a liposome (see Langer, 1990, *Science* 249:1527-1533; Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.)

In yet another embodiment, the compound can be delivered in a controlled release system. In one embodiment, a pump may be used (see Langer, supra; Sefton, 1987, *CRC Crit. Ref Biomed. Eng.* 14:201; Buchwald et al., 1980, *Surgery* 88:507; Saudek et al., 1989, *N. Engl. J. Med.* 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J., 1983, *Macromol. Sci. Rev. Macromol. Chem.* 23:61; see also Levy et al., 1985, *Science* 228:190; During et al., 1989, *Ann. Neurol.* 25:351; Howard et al., 1989, *J. Neurosurg.* 71:105). In yet another embodiment, a controlled release system can be placed in proximity of the therapeutic target, e.g. the bladder, breast, colon, head and neck, kidney, liver, lung, ovary, pancreas, skin or thyroid thus requiring only a fraction of the systemic dose (see, e.g. Goodson, in Medical Applications of Controlled Release, supra, vol. 2, pp. 115-138 (1984)). Other controlled release systems are discussed in the review by Langer (1990, *Science* 249:1527-1533).

In a specific embodiment where the compound of the invention is a nucleic acid encoding a protein, the nucleic acid can be administered in vivo to promote expression of its encoded protein, by constructing it as part of an appropriate nucleic acid expression vector and administering it so that it becomes intracellular, e.g. by use of a retroviral vector (see U.S. Pat. No. 4,980,286), or by direct injection, or by use of microparticle bombardment (e.g. a gene gun; Biolistic, Dupont), or coating with lipids or cell-surface receptors or transfecting agents, or by administering it in linkage to a homeobox-like peptide which is known to enter the nucleus (see e.g. Joliot et al., 1991, *Proc. Natl. Acad. Sci. USA* 88:1864-1868), etc. Alternatively, a nucleic acid can be introduced intracellularly and incorporated within host cell DNA for expression, by homologous recombination.

The present invention also provides pharmaceutical compositions. Such compositions comprise a therapeutically effective amount of a compound, and a pharmaceutically acceptable carrier. In a specific embodiment, the term "pharmaceutically acceptable" means suitable for approval by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, for example in purified form, together with a suitable amount of carrier so as to provide the form for proper administration to the subject. The formulation should suit the mode of administration.

In one embodiment, for example where one or more antibodies are employed, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lidocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds of the invention can be formulated as neutral or salt forms. Pharmaceutically acceptable salts, where appropriate, include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of the compound of the invention which will be effective in the treatment of cancer, for example, the diseases of the invention can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each subject's circumstances. However, suitable dosage ranges for intravenous administration are generally about 20-500 micrograms of active compound per kilogram body weight. Suitable dosage ranges for intranasal administration are generally about 0.01 pg/kg body weight to 1 mg/kg body weight. Effective doses may be extrapolated from dose-response curves derived from in vitro or animal model test systems.

Suppositories generally contain active ingredient in the range of 0.5% to 10% by weight; oral formulations preferably contain 10% to 95% active ingredient.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects (a) approval by the agency of manufacture, use or sale for human administration, (b) directions for use, or both.

Thus in one aspect the kit comprises antibodies employed in the invention, for example the antibodies may be lyophilized for reconstitution before administration or use. Where the kit is for use in therapy/treatment such as cancer the antibody or antibodies may be reconstituted with an isotonic aqueous solution, which may optionally be provided with the kit. In one aspect the kit may comprise a polypeptide such as an immunogenic polypeptide employed in the invention, which may for example be lyophilized. The latter kit may further comprise an adjuvant for reconstiting the immunogenic polypeptide.

The invention also extends to a composition as described herein for example a pharmaceutical composition and/or vaccine composition for use in inducing an immune response in a subject.

Determining Abundance of BST1 by Imaging Technology

An advantage of determining abundance of BST1 by imaging technology may be that such a method is non-invasive (save that reagents may need to be administered) and there is no need to extract a sample from the subject.

Suitable imaging technologies include positron emission tomography (PET) and single photon emission computed tomography (SPECT). Visualisation of BST1 using such techniques requires incorporation or binding of a suitable label e.g. a radiotracer such as $^{18}F$, $^{11}C$ or $^{123}I$ (see e.g. NeuroRx—The Journal of the American Society for Experimental NeuroTherapeutics (2005) 2(2), 348-360 and idem pages 361-371 for further details of the techniques). Radiotracers or other labels may be incorporated into BST1 by administration to the subject (e.g. by injection) of a suitably labelled specific ligand. Alternatively they may be incorporated into a binding affinity reagent (e.g. antibody) specific for BST1 which may be administered to the subject (e.g. by injection). For discussion of use of Affibodies for imaging see e.g. Orlova A, Magnusson M, Eriksson T L, Nilsson M, Larsson B, Hoiden-Guthenberg I, Widstrom C, Carlsson J, Tolmachev V, Stahl S, Nilsson F Y, Tumor imaging using a picomolar affinity HER2 binding Affibody molecule, Cancer Res. 2006 Apr. 15; 66(8):4339-48).

Diagnosis and Treatment of Cancer Including the Diseases of the Invention Using Immunohistochemistry Immunohistochemistry is an excellent detection technique and may therefore be very useful in the diagnosis and treatment of cancer, including the diseases of the invention Immunohistochemistry may be used to detect, diagnose, or monitor cancers such as those mentioned above, through the localization of BST1 antigens in tissue sections by the use of labeled antibodies (or other affinity reagents), derivatives and analogs thereof, which specifically bind to BST1, as specific reagents through antigen-antibody interactions that are visualized by a marker such as fluorescent dye, enzyme, radioactive element or colloidal gold.

The advancement of monoclonal antibody technology has been of great significance in assuring the place of immunohistochemistry in the modern accurate microscopic diagnosis of human neoplasms. The identification of disseminated neoplastically transformed cells by immunohistochemistry allows for a clearer picture of cancer invasion and metastasis, as well as the evolution of the tumour cell associated immunophenotype towards increased malignancy. Future antineoplastic therapeutical approaches may include a variety of individualized immunotherapies, specific for the particular immunophenotypical pattern associated with each individual patient's neoplastic disease. For further discussion see e.g. Bodey B, The significance of immunohistochemistry in the diagnosis and therapy of neoplasms, Expert Opin Biol Ther. 2002 April; 2(4):371-93.

Preferred features of each aspect of the invention are as for each of the other aspects mutatis mutandis. The prior art documents mentioned herein are incorporated to the fullest extent permitted by law.

The invention is illustrated by the following non-limiting examples.

EXAMPLE 1

Identification of BST1 Expressed in Chronic Lymphocytic Leukemia, Breast Cancer, Colorectal Cancer, Kidney Cancer, Lung Cancer and Pancreatic Cancer Tissue Using Liquid Chromatography-Mass Spectrometry (LC/MS)

Using the following Reference Protocol, membrane proteins extracted from breast cancer, colorectal cancer, kidney cancer, lung cancer and pancreatic cancer tissue samples were digested and resulting peptides sequenced by tandem mass spectrometry.

1.1 Materials and Methods
1.1.1 Plasma Membrane Fractionation

All procedures were carried out at 4° C. The cells recovered from chronic lymphocytic leukemia, breast cancer, colorectal cancer, kidney cancer, lung cancer and pancreatic cancer tissue were homogenised and submitted to centrifugation at 1000 G. The supernatant was taken and centrifuged at 49500 G in an ultracentrifuge. The resulting pellet was recovered and put on 1.4 M sucrose cushion. Microsome/plasma membrane was recovered at the phase border and rebuffered in PBS and then again submitted to centrifugation at 49500 G. The pellet (plasma membrane fraction) was then analysed by liquid chromatography-mass spectrometry (LC/MS) (see section 2.1.2 below).

1.1.2 Liquid Chromatography-Mass Spectrometry (LC/MS) Methodology

Plasma membrane fractions suspended in PBS from chronic lymphocytic leukemia, breast cancer, colorectal cancer, kidney cancer, lung cancer and pancreatic cancer tissue samples were centrifuged at 12-14° C. for 45 min at maximum speed of 21460 G in a bench top centrifuge. The supernatant was removed and the required amount of supernatant to give a concentration of 4 mg/ml was added back to the pellet. The equivalent amount of 1% w/v SDS was then added. The samples were then vortexed at room temperature and then centrifuged at 21460 G for 30 min at 12-15° C. The sample was retrieved leaving the pellet behind. To a volume of each protein solution equating to 50 μg, 150 μl of 0.5M triethylammonium bicarbonate (TEAB) solution was added. To each sample, 3 μl of 50 mM tris-(2-carboxyethyl)phosphine was added and the mixture was incubated at 60° C. for 1 hr. 1 μl of cysteine blocking reagent, 200 mM methyl methanethiosulfonate (MMTS) in isopropanol, was then added. After incubation at room temperature for 10 min, 15 μl of 1 μg/μl trypsin was added to each sample followed by incubation at 37° C. overnight.

The digested samples were dried under a vacuum and 40 μl of 0.1% aqueous formic acid was added followed by enough trifluoroacetic acid (TFA) to reduce the pH of the solution to <3 prior to ion exchange fractionation.

1.1.3 Fractionation and Analysis of Labeled Peptides

The sample was fractionated by strong cation exchange chromatography using an Agilent 1200 chromatograph (Agilent, Santa Clara, Calif., USA). Samples were eluted off an Agilent Zorbax Bio-SCXII column (3.5 μm; 50×0 8 mm) using a 20 μl/min gradient of 0-100 mM sodium acetate over 20 min, then to 1M over 10 min, then held at 1M for 25 min. 1 min fractions were collected over 40 min. To each fraction, 2 μl of 1% TFA solution was added. The fractions were then stored at −80° C. Each fraction was analysed by liquid chromatography-mass spectrometry using an Ekigent Tempo chromatograph fitted with a PepMap 100 C18, 3 um, 100Å column, 150 mm×75 mm (LC Packings/Dionex) and a Q-Star Elite quadrupole-time-of-flight instrument (Applied Biosystems/MDS Sciex). Peptides were eluted with a 300 nl/min gradient increasing from 5% to 40% acetonitrile over 60 min. Data was acquired in auto MS/MS mode such that up to 3 precursor ions above the intensity threshold were selected and product ion spectra accumulated to facilitate the sequencing of the peptides. Three passes were performed, each in auto MS/MS mode with the second and third runs also excluding masses already detected in a previous run.

1.1.4 Amino Acid Sequence Analysis of Labeled Peptide

The raw data generated from the QSTAR was processed through the Protein Pilot software (Applied Biosystems/ MDS Analytical Technologies) which uses the Paragon™ algorithm to infer amino acids sequences from the peak lists by searching against a sequence database consisting of IPI version 3.58 and contaminant trypsin sequences. Criteria for peptide identification included trypsin digestion and various biological and chemical modifications (oxidized methionine, cysteine modification by MMTS or iodoacetamide and phosphorylation of serine, threonine and tyrosine). Peptides with a confidence score of 60% or greater were processed into protein groups with the criteria that if only one peptide from a protein group was identified the score must be 80% or greater.

1.1.5 Discrimination of Chronic Lymphocytic Leukemia, Breast Cancer, Colorectal Cancer, Kidney Cancer, Lung Cancer Pancreatic Cancer Associated Proteins The process to identify BST1 uses the peptide sequences obtained experimentally by mass spectrometry described above of naturally occurring human proteins to identify and organize coding exons in the published human genome sequence.

These experimentally determined sequences were compared with the OGAP® database which was compiled by processing and integration of peptide masses, peptide signatures, ESTs and Public Domain Genomic Sequence Data as described in International Patent Application WO2009/087462. The process was used to generate approximately 1 million peptide sequences to identify protein-coding genes and their exons resulted in the identification of protein sequences for 18083 genes across 67 different tissues and 57 diseases including 506 genes in Bladder cancer, 4,713 genes in Breast cancer, 766 genes in Burkitt's lymphoma, 1,371 genes in Cervical cancer, 949 genes in Colorectal cancer, 1,782 genes in Hepatocellular carcinoma, 2,424 genes in CLL, 978 genes in Lung cancer, 1,764 genes in Melanoma, 1,033 genes in Ovarian Cancer, 2,961 genes in Pancreatic cancer and 3,307 genes in Prostate cancer.

1.2 Results

These experiments identified BST1, as further described herein. The full-length BST1 was detected in the plasma membrane of chronic lymphocytic leukemia, breast cancer, colorectal cancer, kidney cancer, lung cancer, ovarian cancer and pancreatic cancer samples and was not detected in the cytosol (FIGS. 1a and 1g). Comparison of the experimentally determined sequences with sequences in the OGAP® database, indicated that BST1 showed a high degree of specificity to breast cancer (Table 1a), colorectal cancer (Table 1b), kidney cancer (Table 1c), lung cancer (Table 1d), pancreatic cancer (Table 1e), head and neck cancer (Table 1f), ovarian cancer (Table 1g) and chronic lymphocytic leukemia (Table 1h) indicative of the prognostic and diagnostic nature of this protein.

TABLE 1a

Breast cancer LC/MS

| Sample batch no. | Experiment no. | Tryptics identified [SEQ ID No] |
|---|---|---|
| Sample 1 | Experiment 1 | SEQ ID No: 5-FMPLSDVLYGR |
| Sample 2 | Experiment 1 | SEQ ID No: 5-FMPLSDVLYGR<br>SEQ ID No: 8-LLQCVDHSTHPDCALK |
| Sample 3 | Experiment 1 | SEQ ID No: 4-DMGFQYSCINDYRPVK<br>SEQ ID No: 5-FMPLSDVLYGR<br>SEQ ID No: 7-GFFADYEIPNLQK<br>SEQ ID No: 9-SLFWENSHLLVNSFADNTR<br>SEQ ID No: 10-VADFLSWCR |
| Sample 4 | Experiment 1 | SEQ ID No: 5-FMPLSDVLYGR<br>SEQ ID No: 7-GFFADYEIPNLQK |

TABLE 1b

Colorectal cancer LC/MS

| Sample batch no. | Experiment no. | Tryptics identified [SEQ ID No] |
|---|---|---|
| Sample 1 | Experiment 1 | SEQ ID No: 7-GFFADYEIPNLQK<br>SEQ ID No: 8-LLQCVDHSTHPDCALK |
| Sample 2 | Experiment 1 | SEQ ID No: 5-FMPLSDVLYGR<br>SEQ ID No: 7-GFFADYEIPNLQK<br>SEQ ID No: 10-VADFLSWCR |
| Sample 3 | Experiment 1 | SEQ ID No: 5-FMPLSDVLYGR<br>SEQ ID No: 7-GFFADYEIPNLQK<br>SEQ ID No: 9-SLFWENSHLLVNSFADNTR<br>SEQ ID No: 10-VADFLSWCR |
| Sample 3 | Experiment 2 | SEQ ID No: 7-GFFADYEIPNLQK<br>SEQ ID No: 8-LLQCVDHSTHPDCALK<br>SEQ ID No: 9-SLFWENSHLLVNSFADNTR |

TABLE 1b -continued

Colorectal cancer LC/MS

| Sample batch no. | Experiment no. | Tryptics identified [SEQ ID No] |
|---|---|---|
| Sample 3 | Experiment 3 | SEQ ID No: 2-ALLSPEQR<br>SEQ ID No: 5-FMPLSDVLYGR<br>SEQ ID No: 7-GFFADYEIPNLQK<br>SEQ ID No: 8-LLQCVDHSTHPDCALK<br>SEQ ID No: 10-VADFLSWCR |

TABLE 1c

Kidney cancer LC/MS

| Sample batch no. | Experiment no. | Tryptics identified [SEQ ID No] |
|---|---|---|
| Sample 1 | Experiment 1 | SEQ ID No: 7-GFFADYEIPNLQK<br>SEQ ID No: 8-LLQCVDHSTHPDCALK<br>SEQ ID No: 10-VADFLSWCR |
| Sample 1 | Experiment 2 | SEQ ID No: 7-GFFADYEIPNLQK<br>SEQ ID No: 10-VADFLSWCR |

TABLE 1d

Lung cancer LC/MS

| Sample batch no. | Experiment no. | Tryptics identified [SEQ ID No] |
|---|---|---|
| Sample 1 | Experiment 1 | SEQ ID No: 5-FMPLSDVLYGR |
| Sample 1 | Experiment 2 | SEQ ID No: 5-FMPLSDVLYGR<br>SEQ ID No: 7-GFFADYEIPNLQK<br>SEQ ID No: 10-VADFLSWCR<br>SEQ ID No: 11-SLFWENSHLLVN |
| Sample 2 | Experiment 1 | SEQ ID No: 10-VADFLSWCR |
| Sample 2 | Experiment 2 | SEQ ID No: 5-FMPLSDVLYGR<br>SEQ ID No: 10-VADFLSWCR |
| Sample 3 | Experiment 1 | SEQ ID No: 5-FMPLSDVLYGR<br>SEQ ID No: 7-GFFADYEIPNLQK<br>SEQ ID No: 8-LLQCVDHSTHPDCALK<br>SEQ ID No: 10-VADFLSWCR |
| Sample 4 | Experiment 1 | SEQ ID No: 7-GFFADYEIPNLQK<br>SEQ ID No: 8-LLQCVDHSTHPDCALK |
| Sample 5 | Experiment 1 | SEQ ID No: 7-GFFADYEIPNLQK<br>SEQ ID No: 10-VADFLSWCR |
| Sample 6 | Experiment 1 | SEQ ID No: 10-VADFLSWCR |
| Sample 7 | Experiment 1 | SEQ ID No: 7-GFFADYEIPNLQK<br>SEQ ID No: 8-LLQCVDHSTHPDCALK<br>SEQ ID No: 10-VADFLSWCR |
| Sample 8 | Experiment 1 | SEQ ID No: 3-DIFLGR<br>SEQ ID No: 4-DMGFQYSCINDYRPVK<br>SEQ ID No: 5-FMPLSDVLYGR<br>SEQ ID No: 7-GFFADYEIPNLQK<br>SEQ ID No: 8-LLQCVDHSTHPDCALK<br>SEQ ID No: 10-VADFLSWCR<br>SEQ ID No: 12-LKDMGFQYSCINDYRPVK |
| Sample 9 | Experiment 1 | SEQ ID No: 2-ALLSPEQR<br>SEQ ID No: 5-FMPLSDVLYGR<br>SEQ ID No: 7-GFFADYEIPNLQK<br>SEQ ID No: 8-LLQCVDHSTHPDCALK<br>SEQ ID No: 10-VADFLSWCR |
| Sample 10 | Experiment 1 | SEQ ID No: 7-GFFADYEIPNLQK |

TABLE 1e

Pancreatic cancer LC/MS

| Sample batch no. | Experiment no. | Tryptics identified [SEQ ID No] |
|---|---|---|
| Sample 1 | Experiment 1 | SEQ ID No: 2-ALLSPEQR |
| | | SEQ ID No: 3-DIFLGR |
| | | SEQ ID No: 5-FMPLSDVLYGR |
| | | SEQ ID No: 7-GFFADYEIPNLQK |
| | | SEQ ID No: 10-VADFLSWCR |
| Sample 2 | Experiment 1 | SEQ ID No: 7-GFFADYEIPNLQK |

TABLE 1f

Head and neck cancer LC/MS

| Sample batch no. | Experiment no. | Tryptics identified [SEQ ID No] |
|---|---|---|
| Sample 1 | Experiment 1 | SEQ ID No: 2-ALLSPEQR |
| | | SEQ ID No: 5-FMPLSDVLYGR |
| | | SEQ ID No: 8-LLQCVDHSTHPDCALK |
| | | SEQ ID No: 10-VADFLSWCR |
| Sample 2 | Experiment 1 | SEQ ID No: 8-LLQCVDHSTHPDCALK |
| | | SEQ ID No: 10-VADFLSWCR |

TABLE 1g

Ovarian cancer LC/MS

| Sample batch no. | Experiment no. | Tryptics identified [SEQ ID No] |
|---|---|---|
| Sample 1 | Experiment 1 | SEQ ID No: 2-ALLSPEQR |
| | | SEQ ID No: 8-LLQCVDHSTHPDCALK |
| Sample 2 | Experiment 1 | SEQ ID No: 2-ALLSPEQR |
| | | SEQ ID No: 5-FMPLSDVLYGR |
| | | SEQ ID No: 6-GEGTSAHLR |
| | | SEQ ID No: 7-GFFADYEIPNLQK |
| | | SEQ ID No: 8-LLQCVDHSTHPDCALK |
| | | SEQ ID No: 10-VADFLSWCR |

TABLE 1h chronic lymphocytic leukemia

| Sample No. | Experiment No. | Peptides identified |
|---|---|---|
| Sample 1 | Experiment 1 | SEQ ID No: 2-ALLSPEQR |
| | | SEQ ID No: 5-FMPLSDVLYGR |
| | | SEQ ID No: 8-LLQCVDHSTHPDCALK |

EXAMPLE 2

Identification of Membrane Proteins Expressed in Lung Cancer Tissue Samples Using Isotope Tagging for Absolute and Relative Quantitation (iTRAQ)

Using the following Reference Protocol, membrane proteins extracted from colorectal cancer, kidney cancer or lung cancer tissues and normal adjacent tissue samples were digested, labeled with Isotope Tagging for Absolute & Relative Quantitation reagents (iTRAQ; Applied Biosystems, Foster City, Calif., USA) and resulting peptides sequenced by tandem mass spectrometry.

2.1 Materials and Methods 2.1.1 Plasma Membrane Fractionation

The cells recovered from a lung cancer and normal adjacent tissue from lung were lysed and submitted to centrifugation at 1000 G. The supernatant was taken, and it was subsequently centrifuged at 3000 G. Once again, the supernatant was taken, and it was then centrifuged at 100 000 G. The resulting pellet was recovered and put on 15-60% sucrose gradient. A Western blot was used to identify sub cellular markers, and the Plasma Membrane fractions were pooled. The pooled solution was then analyzed directly by iTRAQ (see section 2.1.2 below).

2.1.2 iTRAQ Methodology

Membrane protein pellets from lung cancer tissues and normal adjacent tissues from lung were solubilized in sample buffer (2-4 µg/µl in 0.5% SDS) by the addition of buffer and then heating to 95° C. for 3 min. To a volume of each protein solution equating to 50 µg, 150 µl of 0.5M triethylammonium bicarbonate (TEAB) solution was added. To each sample, 3 µl of 50 mM tris-(2-carboxyethyl)phosphine was added and the mixture was incubated at 60° C. for 1 hr. 1 µl of cysteine blocking reagent, 200 mM methyl methanethiosulphonate (MMTS) in isopropanol, was then added. After incubation at room temperature for 10 min, 15 ml of 1 µg/µl trypsin was added to each sample followed by incubation at 37° C. overnight. The digested samples were dried under a vacuum and re-constituted with 30 µl of 0.5M TEAB solution. 70 µl ethanol was added to each of the four iTRAQ reagents (114/115/116/117) and one reagent added to each of the four samples analyzed (each sample comprising two cancer tissue samples and two corresponding normal adjacent tissue samples) and left at room temperature for 1 hr. The specific reagent added to each sample was recorded. The four labeled samples were combined & vortexed. The combined samples was reduced to dryness under a vacuum and de-salted by loading onto a C18 spin column, washing with aqueous solvent and then eluting with 70% acetonitrile. The sample fraction was again reduced to dryness and then re-dissolved in 40 µl of solvent A (97.9 water, 2% acetonitrile, 0.1% formic acid) prior to ion exchange fractionation.

2.1.3 Fractionation and Analysis of Labeled Peptides

The sample was fractionated by strong cation exchange chromatography using an Agilent 1200 chromatograph (Agilent, Santa Clara, Calif., USA). Samples were eluted off an Agilent Zorbax Bio-SCXII column (3.5 µm; 50×0 8 mm) using a 200 min gradient of 0-100 mM sodium acetate over 20 min and then to 1M over 10 min. 1 min fractions were collected over the 30 min run.

Each fraction was analyzed by liquid chromatography/mass spectrometry using an Agilent 1200 chromatograph fitted with a Zorbax 300SB-C18 (150 mm×75 µm) and an Agilent 6510 quadrupole-time-of-flight instrument (Agilent, Santa Clara, Calif., USA). Peptides were eluted with a 300 nl/min gradient increasing from 15% to 45% acetonitrile in 60 min. Data was acquired in auto MS/MS mode such that up to 3 precursor ions above the intensity threshold were selected and product ion spectra accumulated to facilitate the sequencing of the labeled peptides. Raw was processed to create peak lists using Spectrum Mill software (Agilent, Santa Clara, Calif., USA).

2.1.4 Amino Acid Sequence Analysis of Labeled Peptides

For partial amino acid sequencing and identification of ADP-ribosyl cyclase 2 (BST1; CD157), uninterpreted tandem mass spectra of tryptic peptides were searched using the SEQUEST search program (Eng et al., 1994, *J. Am. Soc. Mass Spectrom.*, 5:976-989). Criteria for database identification included: the cleavage specificity of trypsin; the detection of a suite of a, b and y ions in peptides returned from the database, and a mass increment for all cysteine residues to account for modification with methyl methanethiosulphonate and the addition of iTRAQ labels to free amines (N-terminus & lysine). The data was searched through IPI Human v3.23.

2.1.5 Discrimination of Lung Cancer Tissues Associated Proteins

The process to identify BST1 used the peptide sequences obtained experimentally by mass spectrometry, as described above, of naturally occurring human proteins to identify and organize coding exons in the published human genome sequence. These experimentally determined sequences were compared with the OGAP® database which was compiled by processing and integration of peptide masses, peptide signatures, ESTs and Public Domain Genomic Sequence Data as described in International Patent Publication WO2009/087462.

2.2 Results

The experiment identified BST1, as further described herein (Table 2). BST1 was detected in the plasma membrane of non-small cell lung cancer samples (FIG. 2). The iTRAQ analysis showed that the level of BST1 in the cancer samples were higher than in the matched normal adjacent tissue samples.

TABLE 2

| iTRAQ Lung Cancer | | |
|---|---|---|
| Sample No. | Experiment No. | Peptides identified |
| Sample 1 | Experiment 1 | SEQ ID No: 6-GEGTSAHLR |

EXAMPLE 3

Immunohistochemistry Using Antibody to BST1

Using the following Reference Protocol, immunohistochemistry was performed on FFPE tumour and normal tissues using a goat polyclonal antibody to BST1 (R&D Systems Europe, Abingdon, UK).

3.1 Materials and Methods 3.1.1 Deparaffinisation and Rehydration

Slides were heated for 2 hr at 60° C. in 50 ml Falcons in a water bath with no buffer. Each Falcon had one slide or two slides back-to back with long gel loading tip between them to prevent slides from sticking to each other. Slides were deparaffinised in EZ-DeWax (BioGenex, CA, USA) for 5 min in black slide rack, then rinsed well with the same DeWax solution using 1 ml pipette, then washed with water. Slides were placed in a coplin jar filled with water until the pressure cooker was ready; the water was changed a couple of times.

3.1.2 Antigen Retrieval

Water was exchanged for antigen retrieval solution=1× citrate buffer, pH 6 (DAKO). Antigen was retrieved by the pressure cooker method. The slides in the plastic coplin jar in antigen retrieval solution were placed into a pressure cooker which was then heated up to position 6 (the highest setting). 15-20 min into the incubation, the temperature was reduced to position 3 and left at that (when the temperature inside the pressure cooker was 117° C.) for another 20-25 min. Then the hob was switched off and the cooker was placed onto the cold hob and the pressure was released by carefully moving the handle into the position between "open" and "closed". The whole system was left to release the pressure and to cool down for another 20 min. The lid was opened and samples taken out to rest on the bench. The slides were washed 1×5 min with PBS-3T (0.5 L PBS+3 drops of Tween-20) and the slides were placed in PBS.

3.1.3 Staining

After antigen retrieval, slides were mounted in the Shandon Coverplate system. Trapping of air bubbles between the slide and plastic coverplate was prevented by placing the coverplate into the coplin jar filled with PBS and gently sliding the slide with tissue sections into the coverplate. The slide was pulled out of the coplin jar while holding it tightly together with the coverplate. The assembled slide was placed into the rack, letting PBS trapped in the funnel and between the slide and coverplate to run through. Slides were washed with 2×2 ml (or 4×1 ml) PBS-3T and 1×2 ml PBS, waiting until all PBS had gone through the slide and virtually no PBS was left in the funnel Endogenous peroxide blockade was performed using peroxidase blocking reagent (S2001, DAKO). 1-4 drops of peroxide solution was used per slide and incubated for 5 minutes. The slides were rinsed with water and then once with 2 ml PBS-3T and once with 2 ml PBS; it was important to wait until virtually no liquid was left in the funnel before adding a new portion of wash buffer.

The primary antibody was diluted with an Antibody diluent reagent (DAKO). Optimal dilution was determined to be 1:100. 50-200 µl of diluted primary antibody was applied to each section and/or tissue microarray; taking care to cover the whole tissue. The slide was gently tapped to distribute the antibody evenly over the section or a pipette tip was used over the top of the section. The slide was incubated for 45 min in a moist chamber at room temperature. Slides were washed with 2×2 ml (or 4×1 ml) PBS-3T and then 1×2 ml PBS, waiting until all PBS had gone through the slide and virtually no PBS was left in the funnel The corresponding donkey anti-goat IgG:HRP (OBT1500P, 1 mg/ml, Serotec) was applied at 1:1000 and incubated for 35 min at room temperature. The slides were washed as above. The DAB substrate was made up in dilution buffer; 2 ml containing 2 drops of substrate was enough for 10 slides. The DAB reagent was applied to the slides by applying a few drops at a time. All of the DAB was distributed between the slides. The slides were incubated for 10 min. The slides were washed 1×2 ml (or 2×1 ml) with PBS-3T and 1×2 ml (or 2×1 ml) with PBS, waiting until all PBS had gone through the slide and virtually no PBS was left in the funnel Hematoxylin (DAKO) was applied; 1 ml was enough for 10 slides and slides were incubated for 1 min at room temperature. The funnels of the Shandon Coverplate system were filled with 2 ml of water and let to run through. When slides were clear of the excess of hematoxylin, the system was disassembled, tissue sections and/or arrays were washed with water from the wash bottle and placed into a black slide rack. Tissues were rehydrated by incubating in EZ-DeWax for 5 min and then in 95% ethanol for 2-5 min. Slides were left to dry on the bench at room temperature and then mounted in mounting media and covered with coverslip.

3.2 Results

Immunohistochemical analysis revealed specific staining of tumor cells in lung cancer tissue sections. In a lung tissue array representing 59 patients with lung cancer, elevated staining of BST1 in cancer cells was seen in 28 patients (47%). Thus antibodies directed to BST1 may have utility as therapeutics and diagnostics in this cancer and other cancer types showing expression of BST1.

EXAMPLE 4

RNA Profiling of BST1

4.1 Materials and Methods

Various normal and cancerous tissues were screened for BST1 mRNA expression using quantitative reverse transcriptase polymerase chain reaction (RT-PCR).

4.2 Results

FIG. 3a shows the RT-PCR results for BST1 for a variety of normal and cancerous tissues. The vertical axis shows the copy #/5 ng cDNA of BST1. mRNA profiling revealed a strikingly high expression level of the target in NPB-monocytes and CD33+ cells, contrasting with the very low expression profile in most normal tissues. Expression of mRNA is indicative of BST1 protein expression. FIG. 3b shows the results of further mRNA expression analysis which again show high levels of BST1 expression in monocytes and CD33+ cells. Levels in NPB-monocytes and CD33+ cells were found to be 20-30 fold higher than any other tissue/cell type.

Figure 3C:
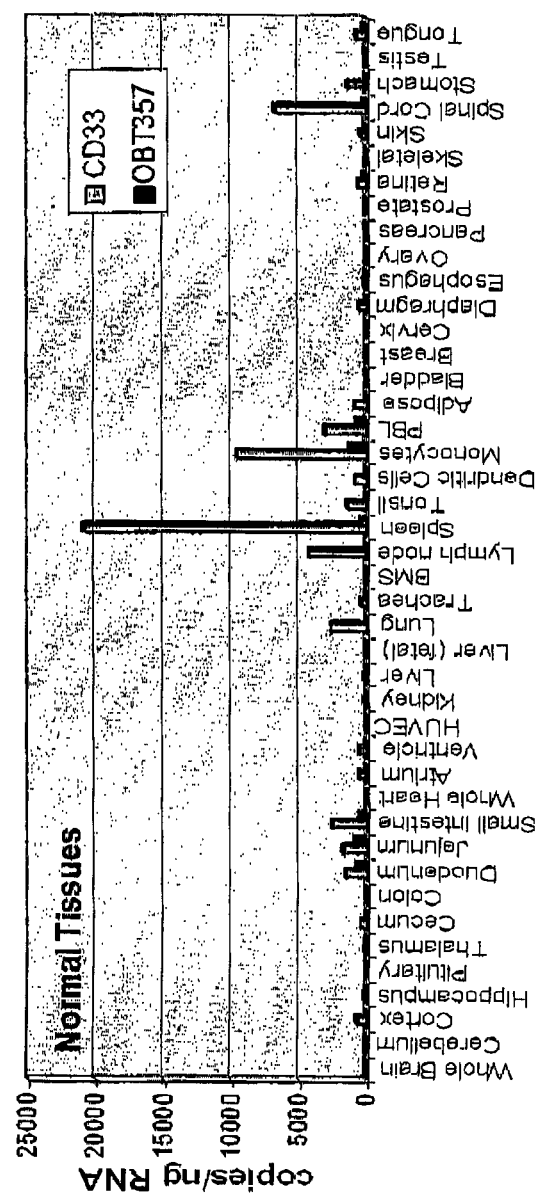
FIG. 3c shows the results of comparative RT-PCR profiling on a set of normal tissues displaying BST1 expression alongside CD33.

FIG. 3c shows the results of comparative RT-PCR profiling which was performed on a set of normal tissues displaying BST1 expression alongside CD33, a transmembrane receptor expressed on cells of myeloid lineage, and the target of gemtuzumab ozogamicin (Mylotarg), a monoclonal antibody-based treatment for acute myeloid leukemia. It was found that BST1 has a highly restricted normal expression profile compared to CD33.

EXAMPLE 5

Construction of a Phage-Display Library

A recombinant protein composed of amino acids 29-292 of BST1 (SEQ ID NO:13) was eurkaryotically synthesized by standard recombinant methods and used as antigen for immunization.

Immunization and mRNA Isolation

A phage display library for identification of the BST1-binding molecules was constructed as follows. A/J mice (Jackson Laboratories, Bar Harbor, Me.) were immunized intraperitoneally with the recombinant BST1 antigen (the extracellular domain), using 100 µg protein in Freund's complete adjuvant, on day 0, and with 100 µg antigen on day 28. Test bleeds of mice were obtained through puncture of the retro-orbital sinus. If, by testing the titers, they were deemed high by ELISA using the biotinylated BST1 antigen immobilized via neutravidin (Reacti-Bind™) NeutrAvidin™-Coated Polystyrene Plates, Pierce, Rockford, Ill.), the mice were boosted with 100 µg of protein on day 70, 71 and 72, with subsequent sacrifice and splenectomy on day 77. If titers of antibody were not deemed satisfactory, mice were boosted with 100 µg antigen on day 56 and a test bleed taken on day 63. If satisfactory titers were obtained, the animals were boosted with 100 µg of antigen on day 98, 99, and 100 and the spleens harvested on day 105.

The spleens were harvested in a laminar flow hood and transferred to a petri dish, trimming off and discarding fat and connective tissue. The spleens were macerated quickly with the plunger from a sterile 5 cc syringe in the presence of 1.0 ml of solution D (25.0 g guanidine thiocyanate (Boehringer Mannheim, Indianapolis, Ind.), 29.3 ml sterile water, 1.76 ml 0.75 M sodium citrate pH 7.0, 2.64 ml 10% sarkosyl (Fisher Scientific, Pittsburgh, Pa.), 0.36 ml 2-mercaptoethanol (Fisher Scientific, Pittsburgh, Pa.). This spleen suspension was pulled through an 18 gauge needle until all cells were lysed and the viscous solution was transferred to a microcentrifuge tube. The petri dish was washed with 100 µl of solution D to recover any remaining spleen. This suspension was then pulled through a 22 gauge needle an additional 5-10 times.

The sample was divided evenly between two microcentrifuge tubes and the following added, in order, with mixing by inversion after each addition: 50 µl 2 M sodium acetate pH 4.0, 0.5 ml water-saturated phenol (Fisher Scientific, Pittsburgh, Pa.), 100 µl chloroform/isoamyl alcohol 49:1 (Fisher Scientific, Pittsburgh, Pa.). The solution was vortexed for 10 sec and incubated on ice for 15 min. Following centrifugation at 14 krpm for 20 min at 2-8° C., the aqueous phase was transferred to a fresh tube. An equal volume of water saturated phenol:chloroform:isoamyl alcohol (50:49:1) was added, and the tube vortexed for ten seconds. After 15 min incubation on ice, the sample was centrifuged for 20 min at 2-8° C., and the aqueous phase transferred to a fresh tube and precipitated with an equal volume of isopropanol at −20° C. for a minimum of 30 min. Following centrifugation at 14 krpm for 20 min at 4° C., the supernatant was aspirated away, the tubes briefly spun and all traces of liquid removed from the RNA pellet.

The RNA pellets were each dissolved in 300 µl of solution D, combined, and precipitated with an equal volume of isopropanol at −20° C. for a minimum of 30 min. The sample was centrifuged 14 krpm for 20 min at 4° C., the supernatant aspirated as before, and the sample rinsed with 100 µL of ice-cold 70% ethanol. The sample was again centrifuged 14 krpm for 20 min at 4° C., the 70% ethanol solution aspirated, and the RNA pellet dried in vacuo. The pellet was resuspended in 100 µL of sterile diethyl pyrocarbonate-treated water. The concentration was determined by A260 using an absorbance of 1.0 for a concentration of 40 µg/ml. The RNAs were stored at −80° C.

Preparation of Complementary DNA (cDNA)

The total RNA purified from mouse spleens as described above was used directly as template for cDNA preparation. RNA (50 µg) was diluted to 100 µL with sterile water, and 10 µL of 130 ng/µl oligo dT12 (synthesized on Applied Biosystems Model 392 DNA synthesizer) was added. The sample was heated for 10 min at 70° C., then cooled on ice. Forty µL 5* first strand buffer was added (Gibco/BRL, Gaithersburg, Md.), along with 20 µL 0.1 M dithiothreitol (Gibco/BRL, Gaithersburg, Md.), 10 µL 20 mM deoxynucleoside triphosphates (dNTP's, Boehringer Mannheim, Indianapolis, Ind.), and 10 µL water on ice. The sample was then incubated at 37° C. for 2 min. Ten µL reverse transcriptase (Superscript™) II, Gibco/BRL, Gaithersburg, Md.)

was added and incubation was continued at 37° C. for 1 hr. The cDNA products were used directly for polymerase chain reaction (PCR).

Amplification of Antibody Genes by PCR

To amplify substantially all of the H and L chain genes using PCR, primers were chosen that corresponded to substantially all published sequences. Because the nucleotide sequences of the amino termini of H and L contain considerable diversity, 33 oligonucleotides were synthesized to serve as 5' primers for the H chains, and 29 oligonucleotides were synthesized to serve as 5' primers for the kappa L chains as described in U.S. Pat. No. 6,555,310. The constant region nucleotide sequences for each chain required only one 3' primer for the H chains and one 3' primer for the kappa L chains.

A 50 µL reaction was performed for each primer pair with 50 µmol of 5' primer, 50 µmol of 3' primer, 0.25 µL Taq DNA Polymerase (5 units/µL, Boehringer Mannheim, Indianapolis, Ind.), 3 µL cDNA (prepared as described), 5 µL 2 mM dNTP's, 5 µL 10*Taq DNA polymerase buffer with MgCL2 (Boehringer Mannheim, Indianapolis, Ind.), and $H_2O$ to 50 µL. Amplification was done using a GeneAmp(R) 9600 thermal cycler (Perkin Elmer, Foster City, Calif.) with the following thermocycle program: 94° C. for 1 min; 30 cycles of 94° C. for 20 sec, 55° C. for 30 sec, and 72° C. for 30 sec, 72° C. for 6 min; 4° C.

The dsDNA products of the PCR process were then subjected to asymmetric PCR using only a 3' primer to generate substantially only the anti-sense strand of the target genes. A 100 µL reaction was done for each dsDNA product with 200 µmol of 3' primer, 2 µL of ds-DNA product, 0.5 µL Taq DNA Polymerase, 10 µL 2 mM dNTP's, 10 µL 10*Taq DNA polymerase buffer with $MgCl_2$ (Boehringer Mannheim, Indianapolis, Ind.), and $H_2O$ to 100 µL. The same PCR program as that described above was used to amplify the single-stranded (ss)-DNA.

Purification of Single-Stranded DNA by High Performance Liquid Chromatography and Kinasing Single-Stranded DNA The H chain ss-PCR products and the L chain single-stranded PCR products were ethanol precipitated by adding 2.5 volumes ethanol and 0.2 volumes 7.5 M ammonium acetate and incubating at −20° C. for at least 30 min. The DNA was pelleted by centrifuging in an Eppendorf centrifuge at 14 krpm for 10 min at 2-8° C. The supernatant was carefully aspirated, and the tubes were briefly spun a 2nd time. The last drop of supernatant was removed with a pipette. The DNA was dried in vacuo for 10 min on medium heat. The H chain products were pooled in 210 µL water and the L chain products were pooled separately in 210 µL water. The single-stranded DNA was purified by high performance liquid chromatography (HPLC) using a Hewlett Packard 1090 HPLC and a Gen-Pak™ FAX anion exchange column (Millipore Corp., Milford, Mass.). The gradient used to purify the single-stranded DNA is shown in Table 3, and the oven temperature was 60° C. Absorbance was monitored at 260 nm. The single-stranded DNA eluted from the HPLC was collected in 0.5 min fractions. Fractions containing single-stranded DNA were ethanol precipitated, pelleted and dried as described above. The dried DNA pellets were pooled in 200 µL sterile water.

TABLE 3

HPLC gradient for purification of ss-DNA

| Time (min) | % A | % B | % C | Flow (ml/min) |
|---|---|---|---|---|
| 0 | 70 | 30 | 0 | 0.75 |
| 2 | 40 | 60 | 0 | 0.75 |
| 17 | 15 | 85 | 0 | 0.75 |
| 18 | 0 | 100 | 0 | 0.75 |
| 23 | 0 | 100 | 0 | 0.75 |
| 24 | 0 | 0 | 100 | 0.75 |
| 28 | 0 | 0 | 100 | 0.75 |
| 29 | 0 | 100 | 0 | 0.75 |
| 34 | 0 | 100 | 0 | 0.75 |
| 35 | 70 | 30 | 0 | 0.75 |

Buffer A is 25 mM Tris, 1 mM EDTA, pH 8.0
Buffer B is 25 mM Tris, 1 mM EDTA, 1 M NaCl, pH 8.0
Buffer C is 40 mm phosphoric acid The single-stranded DNA was 5'-phosphorylated in preparation for mutagenesis. Twenty-four µL 10* kinase buffer (United States Biochemical, Cleveland, Ohio), 10.4 µL 10 mM adenosine-5'-triphosphate (Boehringer Mannheim, Indianapolis, Ind.), and 2 µL polynucleotide kinase (30 units/µL, United States Biochemical, Cleveland, Ohio) was added to each sample, and the tubes were incubated at 37° C. for 1 hr. The reactions were stopped by incubating the tubes at 70° C. for 10 min. The DNA was purified with one extraction of Tris equilibrated phenol (pH>8.0, United States Biochemical, Cleveland, Ohio):chloroform:isoamyl alcohol (50:49:1) and one extraction with chloroform:isoamyl alcohol (49:1). After the extractions, the DNA was ethanol precipitated and pelleted as described above. The DNA pellets were dried, then dissolved in 50 µL sterile water. The concentration was determined by measuring the absorbance of an aliquot of the DNA at 260 nm using 33 µg/ml for an absorbance of 1.0. Samples were stored at −20° C.

Preparation of Uracil Templates Used in Generation of Spleen Antibody Phage Libraries One ml of E. coli CJ236 (BioRAD, Hercules, Calif.) overnight culture was added to 50 ml 2*YT in a 250 ml baffled shake flask. The culture was grown at 37° C. to OD600=0.6, inoculated with 10 µl of a 1/100 dilution of BS45 vector phage stock (described in U.S. Pat. No. 6,555, 310) and growth continued for 6 hr. Approximately 40 ml of the culture was centrifuged at 12 krpm for 15 min at 4° C. The supernatant (30 ml) was transferred to a fresh centrifuge tube and incubated at room temperature for 15 min after the addition of 15 µl of 10 mg/ml RNaseA (Boehringer Mannheim, Indianapolis, Ind.). The phages were precipitated by the addition of 7.5 ml of 20% polyethylene glycol 8000 (Fisher Scientific, Pittsburgh, Pa.)/3.5M ammonium acetate (Sigma Chemical Co., St. Louis, Mo.) and incubation on ice for 30 min. The sample was centrifuged at 12 krpm for 15 min at 2-8° C. The supernatant was carefully discarded, and the tube briefly spun to remove all traces of supernatant. The pellet was resuspended in 400 µl of high salt buffer (300 mM NaCl, 100 mM Tris pH 8.0, 1 mM EDTA), and transferred to a 1.5 ml tube.

The phage stock was extracted repeatedly with an equal volume of equilibrated phenol:chloroform:isoamyl alcohol (50:49:1) until no trace of a white interface was visible, and then extracted with an equal volume of chloroform:isoamyl alcohol (49:1). The DNA was precipitated with 2.5 volumes of ethanol and 1/5 volume 7.5 M ammonium acetate and incubated 30 min at −20° C. The DNA was centrifuged at 14 krpm for 10 min at 4° C., the pellet washed once with cold 70% ethanol, and dried in vacuo. The uracil template DNA was dissolved in 30 µl sterile water and the concentration determined by A260 using an absorbance of 1.0 for a concentration of 40 µg/ml. The template was diluted to 250 ng/µL with sterile water, aliquoted and stored at −20° C.

Mutagenesis of Uracil Template with ss-DNA and Electroporation into E. coli to Generate Antibody Phage Libraries Antibody phage display libraries were generated by simultaneously introducing single-stranded heavy and light chain genes onto a phage display vector uracil template. A typical mutagenesis was performed on a 2 µg scale by mixing the following in a 0.2 ml PCR reaction tube: 8 µl of (250 ng/µL) uracil template, 8 µL of 10* annealing buffer (200 mM Tris pH 7.0, 20 mM MgCl2, 500 mM NaCl), 3.33 µl of kinased single-stranded heavy chain insert (100 ng/µL), 3.1 µl of kinased single-stranded light chain insert (100 ng/µL), and sterile water to 80 µl. DNA was annealed in a GeneAmp(R) 9600 thermal cycler using the following thermal profile: 20 sec at 94° C., 85° C. for 60 sec, 85° C. to 55° C. ramp over 30 min, hold at 55° C. for 15 min. The DNA was transferred to ice after the program finished. The extension/ligation was carried out by adding 8 µl of 10* synthesis buffer (5 mM each dNTP, 10 mM ATP, 100 mM Tris pH 7.4, 50 mM MgCl$_2$, 20 mM DTT), 8 µL T4 DNA ligase (1 U/µL, Boehringer Mannheim, Indianapolis, Ind.), 8 µL diluted T7 DNA polymerase (1 U/µL, New England BioLabs, Beverly, Mass.) and incubating at 37° C. for 30 min. The reaction was stopped with 300 µL of mutagenesis stop buffer (10 mM Tris pH 8.0, 10 mM EDTA). The mutagenesis DNA was extracted once with equilibrated phenol (pH>8):chloroform:isoamyl alcohol (50:49:1), once with chloroform:isoamyl alcohol (49:1), and the DNA was ethanol precipitated at −20° C. for at least 30 min. The DNA was pelleted and the supernatant carefully removed as described above. The sample was briefly spun again and all traces of ethanol removed with a pipetman. The pellet was dried in vacuo. The DNA was resuspended in 4 µL of sterile water.

One µL of mutagenesis DNA (500 ng) was transferred into 40 µl electrocompetent E. coli DH12S (Gibco/BRL, Gaithersburg, Md.) using electroporation. The transformed cells were mixed with approximately 1.0 ml of overnight XL-1 cells which were diluted with 2*YT broth to 60% the original volume. This mixture was then transferred to a 15-ml sterile culture tube and 9 ml of top agar added for plating on a 150-mm LB agar plate. Plates were incubated for 4 hr at 37° C. and then transferred to 20° C. overnight. First round antibody phage were made by eluting phage off these plates in 10 ml of 2*YT, spinning out debris, and taking the supernatant. These samples are the antibody phage display libraries used for selecting antibodies against the BST1. Efficiency of the electroporations was measured by plating 10 µl of a $10^{-4}$ dilution of suspended cells on LB agar plates, follow by overnight incubation of plates at 37° C. The efficiency was calculated by multiplying the number of plaques on the $10^{-4}$ dilution plate by 106. Library electroporation efficiencies are typically greater than $1*10^7$ phages under these conditions.

Transformation of E. Coli by Electroporation

Electrocompetent E. coli cells were thawed on ice. DNA was mixed with 40 L of these cells by gently pipetting the cells up and down 2-3 times, being careful not to introduce an air bubble. The cells were transferred to a Gene Pulser cuvette (0.2 cm gap, BioRAD, Hercules, Calif.) that had been cooled on ice, again being careful not to introduce an air bubble in the transfer. The cuvette was placed in the E. coli Pulser (BioRAD, Hercules, Calif.) and electroporated with the voltage set at 1.88 kV according to the manufacturer's recommendation. The transformed sample was immediately resuspended in 1 ml of 2*YT broth or 1 ml of a mixture of 400 µl 2*YT/600 µl overnight XL-1 cells and processed as procedures dictated.

Plating M13 Phage or Cells Transformed with Antibody Phage-Display Vector Mutagenesis Reaction Phage samples were added to 200 µL of an overnight culture of E. coli XL1-Blue when plating on 100 mm LB agar plates or to 600 µL of overnight cells when plating on 150 mm plates in sterile 15 ml culture tubes. After adding LB top agar (3 ml for 100 mm plates or 9 ml for 150 mm plates, top agar stored at 55° C. (see, Appendix A1, Sambrook et al., supra.), the mixture was evenly distributed on an LB agar plate that had been pre-warmed (37° C.-55° C.) to remove any excess moisture on the agar surface. The plates were cooled at room temperature until the top agar solidified. The plates were inverted and incubated at 37° C. as indicated.

Preparation of Biotinylated Tyrosine-Protein Kinase Transmembrane Receptor BST1 and Biotinylated Antibodies The concentrated recombinant BST1 antigen (full length extracellular domain) was extensively dialyzed into BBS (20 mM borate, 150 mM NaCl, 0.1% NaN$_3$, pH 8.0). After dialysis, 1 mg of the BST1 (1 mg/ml in BBS) was reacted with a 15 fold molar excess of biotin-XX-NHS ester (Molecular Probes, Eugene, Oreg., stock solution at 40 mM in DMSO). The reaction was incubated at room temperature for 90 min and then quenched with taurine (Sigma Chemical Co., St. Louis, Mo.) at a final concentration of 20 mM. The biotinylation reaction mixture was then dialyzed against BBS at 2-8° C. After dialysis, the biotinylated BST1 was diluted in panning buffer (40 mM Tris, 150 mM NaCl, 20 mg/ml BSA, 0.1% Tween 20, pH 7.5), aliquoted, and stored at −80° C. until needed.

Antibodies were reacted with 3-(N-maleimidylpropionyl) biocytin (Molecular Probes, Eugene, Oreg.) using a free cysteine located at the carboxy terminus of the heavy chain. Antibodies were reduced by adding DTT to a final concentration of 1 mM for 30 min at room temperature. Reduced antibody was passed through a Sephadex G50 desalting column equilibrated in 50 mM potassium phosphate, 10 mM boric acid, 150 mM NaCl, pH 7.0. 3-(N-maleimidylpropionyl)-biocytin was added to a final concentration of 1 mM and the reaction allowed to proceed at room temperature for 60 min. Samples were then dialyzed extensively against BBS and stored at 2-8° C.

Preparation of Avidin Magnetic Latex

The magnetic latex (Estapor, 10% solids, Bangs Laboratories, Fishers, Ind.) was thoroughly resuspended and 2 ml aliquoted into a 15 ml conical tube. The magnetic latex was suspended in 12 ml distilled water and separated from the solution for 10 min using a magnet (PerSeptive Biosystems, Framingham, Mass.). While maintaining the separation of the magnetic latex with the magnet, the liquid was carefully removed using a 10 ml sterile pipette. This washing process was repeated an additional three times. After the final wash, the latex was resuspended in 2 ml of distilled water. In a separate 50 ml conical tube, 10 mg of avidin-HS (NeutrAvidin, Pierce, Rockford, Ill.) was dissolved in 18 ml of 40 mM Tris, 0.15 M sodium chloride, pH 7.5 (TBS). While vortexing, the 2 ml of washed magnetic latex was added to the diluted avidin-HS and the mixture mixed an additional 30 sec. This mixture was incubated at 45° C. for 2 hr, shaking every 30 min. The avidin magnetic latex was separated from the solution using a magnet and washed three times with 20 ml BBS as described above. After the final wash, the latex was resuspended in 10 ml BBS and stored at 4° C.

Immediately prior to use, the avidin magnetic latex was equilibrated in panning buffer (40 mM Tris, 150 mM NaCl, 20 mg/ml BSA, 0.1% Tween 20, pH 7.5). The avidin magnetic latex needed for a panning experiment (200 µl/sample) was added to a sterile 15 ml centrifuge tube and brought to 10 ml with panning buffer. The tube was placed on the magnet for 10 min to separate the latex. The solution was carefully removed with a 10 ml sterile pipette as described above. The magnetic latex was resuspended in 10 ml of panning buffer to begin the second wash. The magnetic latex was washed a total of 3 times with panning buffer. After the final wash, the latex was resuspended in panning buffer to the starting volume.

EXAMPLE 6

Selection of Recombinant Polyclonal Antibodies to BST1 Antigen

Binding reagents that specifically bind to the BST1 were selected from the phage display libraries created from hyper-immunized mice as described in Example 5.
Panning First round antibody phage were prepared as described in Example 5 using BS45 uracil template. Electroporations of mutagenesis DNA were performed yielding phage samples derived from different immunized mice. To create more diversity in the recombinant polyclonal library, each phage sample was panned separately.

Before the first round of functional panning with the biotinylated BST1 antigen, antibody phage libraries were selected for phage displaying both heavy and light chains on their surface by panning with 7F11-magnetic latex (as described in Examples 21 and 22 of U.S. Pat. No. 6,555,310). Functional panning of these enriched libraries was performed in principle as described in Example 16 of U.S. Pat. No. 6,555,310. Specifically, 10 µL of $1*10^{-6}$ M biotinylated BST1 antigen was added to the phage samples (approximately $1*10^{-8}$ M final concentration of the BST1), and the mixture allowed to come to equilibrium overnight at 2-8° C.

After reaching equilibrium, samples were panned with avidin magnetic latex to capture antibody phage bound to the BST1. Equilibrated avidin magnetic latex (Example 5), 200 µL latex per sample, was incubated with the phage for 10 min at room temperature. After 10 min, approximately 9 ml of panning buffer was added to each phage sample, and the magnetic latex separated from the solution using a magnet. After a ten minute separation, unbound phage was carefully removed using a 10 ml sterile pipette. The magnetic latex was then resuspended in 10 ml of panning buffer to begin the second wash. The latex was washed a total of three times as described above. For each wash, the tubes were in contact with the magnet for 10 min to separate unbound phage from the magnetic latex. After the third wash, the magnetic latex was resuspended in 1 ml of panning buffer and transferred to a 1.5 mL tube. The entire volume of magnetic latex for each sample was then collected and resuspended in 200 µl 2*YT and plated on 150 mm LB plates as described in Example 1 to amplify bound phage. Plates were incubated at 37° C. for 4 hr, then overnight at 20° C.

The 150 mm plates used to amplify bound phage were used to generate the next round of antibody phage. After the overnight incubation, second round antibody phage were eluted from the 150 mm plates by pipetting 10 mL of 2*YT media onto the lawn and gently shaking the plate at room temperature for 20 min. The phage samples were then transferred to 15 ml disposable sterile centrifuge tubes with a plug seal cap, and the debris from the LB plate pelleted by centrifuging the tubes for 15 min at 3500 rpm. The supernatant containing the second round antibody phage was then transferred to a new tube.

A second round of functional panning was set up by diluting 100 µL of each phage stock into 900 µL of panning buffer in 15 ml disposable sterile centrifuge tubes. The biotinylated BST1 antigen was then added to each sample as described for the first round of panning, and the phage samples incubated for 1 hr at room temperature. The phage samples were then panned with avidin magnetic latex as described above. The progress of panning was monitored at this point by plating aliquots of each latex sample on 100 mm LB agar plates to determine the percentage of kappa positives. The majority of latex from each panning (99%) was plated on 150 mm LB agar plates to amplify the phage bound to the latex. The 100 mm LB agar plates were incubated at 37° C. for 6-7 hr, after which the plates were transferred to room temperature and nitrocellulose filters (pore size 0.45 mm, BA85 Protran, Schleicher and Schuell, Keene, N.H.) were overlaid onto the plaques.

Plates with nitrocellulose filters were incubated overnight at room temperature and then developed with a goat anti-mouse kappa alkaline phosphatase conjugate to determine the percentage of kappa positives as described below. Phage samples with lower percentages (<70%) of kappa positives in the population were subjected to a round of panning with 7F 11-magnetic latex before performing a third functional round of panning overnight at 2-8° C. using the biotinylated BST1 antigen at approximately $2*10^{-9}$ M. This round of panning was also monitored for kappa positives. Individual phage samples that had kappa positive percentages greater than 80% were pooled and subjected to a final round of panning overnight at 2-8° C. at $5*10^{-9}$ M. The BST1 antibody genes contained within the eluted phage from this fourth round of functional panning were subcloned into the expression vector, pBRncoH3.

The subcloning process was done generally as described in Example 18 of U.S. Pat. No. 6,555,310. After subcloning, the expression vector was electroporated into DH10B cells and the mixture grown overnight in 2*YT containing 1% glycerol and 10 µg/ml tetracycline. After a second round of growth and selection in tetracycline, aliquots of cells were frozen at −80° C. as the source for the BST1 polyclonal antibody production. Monoclonal antibodies were selected from these polyclonal mixtures by plating a sample of the mixture on LB agar plates containing 10 µg/ml tetracycline and screening for antibodies that recognized the BST1.
Expression and Purification of Recombinant Antibodies Against BST1

A shake flask inoculum was generated overnight from a −70° C. cell bank in an Innova 4330 incubator shaker (New Brunswick Scientific, Edison, N.J.) set at 37° C., 300 rpm. The inoculum was used to seed a 20 L fermentor (Applikon, Foster City, Calif.) containing defined culture medium [Pack et al. (1993) *BioTechnology* 11: 1271-1277] supplemented with 3 g/L L-leucine, 3 g/L L-isoleucine, 12 g/L casein digest (Difco, Detroit, Mich.), 12.5 g/L glycerol and 10 µg/ml tetracycline. The temperature, pH and dissolved oxygen in the fermentor were controlled at 26° C., 6.0-6.8 and 25% saturation, respectively. Foam was controlled by addition of polypropylene glycol (Dow, Midland, Mich.). Glycerol was added to the fermentor in a fed-batch mode. Fab expression was induced by addition of L(+)-arabinose (Sigma, St. Louis, Mo.) to 2 g/L during the late logarithmic growth phase. Cell density was measured by optical density at 600 nm in an UV-1201 spectrophotometer (Shimadzu, Columbia, Md.). Following run termination and adjustment of pH to 6.0, the culture was passed twice through an M-210B-EH Microfluidizer (Microfluidics, Newton, Mass.) at 17,000 psi. The high pressure homogenization of the cells released the Fab into the culture supernatant.

The first step in purification was expanded bed immobilized metal affinity chromatography (EB-IMAC). Streamline™ chelating resin (Pharmacia, Piscataway, N.J.) was charged with 0.1 M $NiCl_2$ and was then expanded and equilibrated in 50 mM acetate, 200 mM NaCl, 10 mM imidazole, 0.01% $NaN_3$, pH 6.0 buffer flowing in the upward direction. A stock solution was used to bring the culture homogenate to 10 mM imidazole, following which it was diluted two-fold or higher in equilibration buffer to reduce the wet solids content to less than 5% by weight. It was then loaded onto the Streamline column flowing in the upward direction at a superficial velocity of 300 cm/hr. The cell debris passed through unhindered, but the Fab was captured by means of the high affinity interaction between nickel and the hexahistidine tag on the Fab heavy chain. After washing, the expanded bed was converted to a packed bed and the Fab was eluted with 20 mM borate, 150 mM NaCl, 200 mM imidazole, 0.01% $NaN_3$, pH 8.0 buffer flowing in the downward direction.

The second step in the purification used ion-exchange chromatography (IEC). Q Sepharose FastFlow resin (Pharmacia, Piscataway, N.J.) was equilibrated in 20 mM borate, 37.5 mM NaCl, 0.01% $NaN_3$, pH 8.0. The Fab elution pool from the EB-IMAC step was diluted four-fold in 20 mM borate, 0.01% $NaN_3$, pH 8.0 and loaded onto the IEC column. After washing, the Fab was eluted with a 37.5-200 mM NaCl salt gradient. The elution fractions were evaluated for purity using an Xcell II™ SDS-PAGE system (Novex, San Diego, Calif.) prior to pooling. Finally, the Fab pool was concentrated and diafiltered into 20 mM borate, 150 mM NaCl, 0.01% $NaN_3$, pH 8.0 buffer for storage. This was achieved in a Sartocon Slice™ system fitted with a 10,000 MWCO cassette (Sartorius, Bohemia, N.Y.). The final purification yields were typically 50%. The concentration of the purified Fab was measured by UV absorbance at 280 nm, assuming an absorbance of 1.6 for a 1 mg/ml solution.

EXAMPLE 7

Specificity of Monoclonal Antibodies to BST1 Determined by Flow Cytometry Analysis Flow cytometric analysis was conducted on CD33+ peripheral blood cells from AML patients using goat polyclonal antibody sc7113 (Santa Cruz Biotechnology, Inc, CA). Comparative FACS studies were also performed in a subset of human leukocytes comparing BST1 with CD33.

The specificity of antibodies against the BST1 selected in Example 6 was also tested by flow cytometry. To test the ability of the antibodies to bind to the cell surface BST1 protein, the antibodies were incubated with the BST1-expressing cells, H226 (human lung squamous carcinoma) and A549 (human lung adenocarinoma). Cells were washed in FACS buffer (DPBS, 2% FBS), centrifuged and resuspended in 100 µl of the diluted primary BST1 antibody (also diluted in FACS buffer). The antibody-A549 complex and antibody-H226 complex were incubated on ice for 60 min and then washed twice with FACS buffer as described above. The cell-antibody pellet was resuspended in 100 µl of the diluted secondary antibody (also diluted in FACS buffer) and incubated on ice for 60 min on ice. The pellet was washed as before and resuspended in 200 µl FACS buffer. The samples were loaded onto the BD FACScanto II flow sytometer and the data analyzed using the BD FACSdiva software. The binding of BST1_µl and BST1_A2 to BST1 expressed on A549 and H226 cells were analysed using flow cytometry.

Results

Figure 4A:
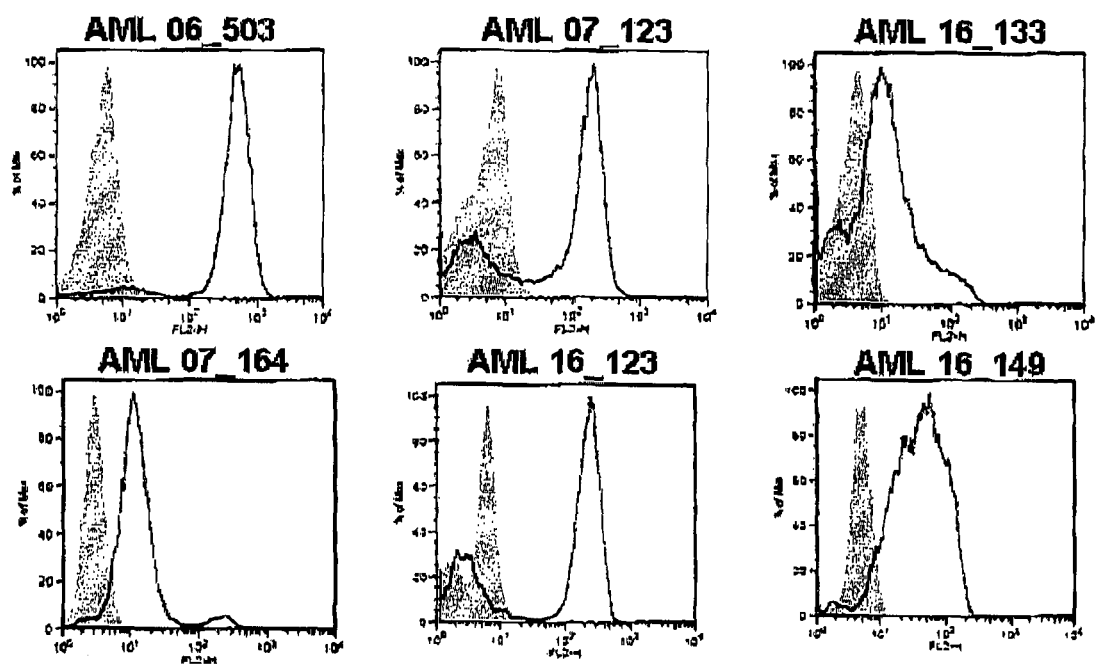
FIG. 4a shows the results of flow cytometric analysis of BST1 in AML patients.

FIG. 4a shows the flow cytometric analysis of 6 AML samples. It shows the CD33+ peripheral blood cells from AML patients either stained with anti-BST1 antibodies (clear area under curve), or unstained (grey area). The results show positive staining with an anti-BST1 antibody in 6 out of 6 AML patients.

Figure 4B:
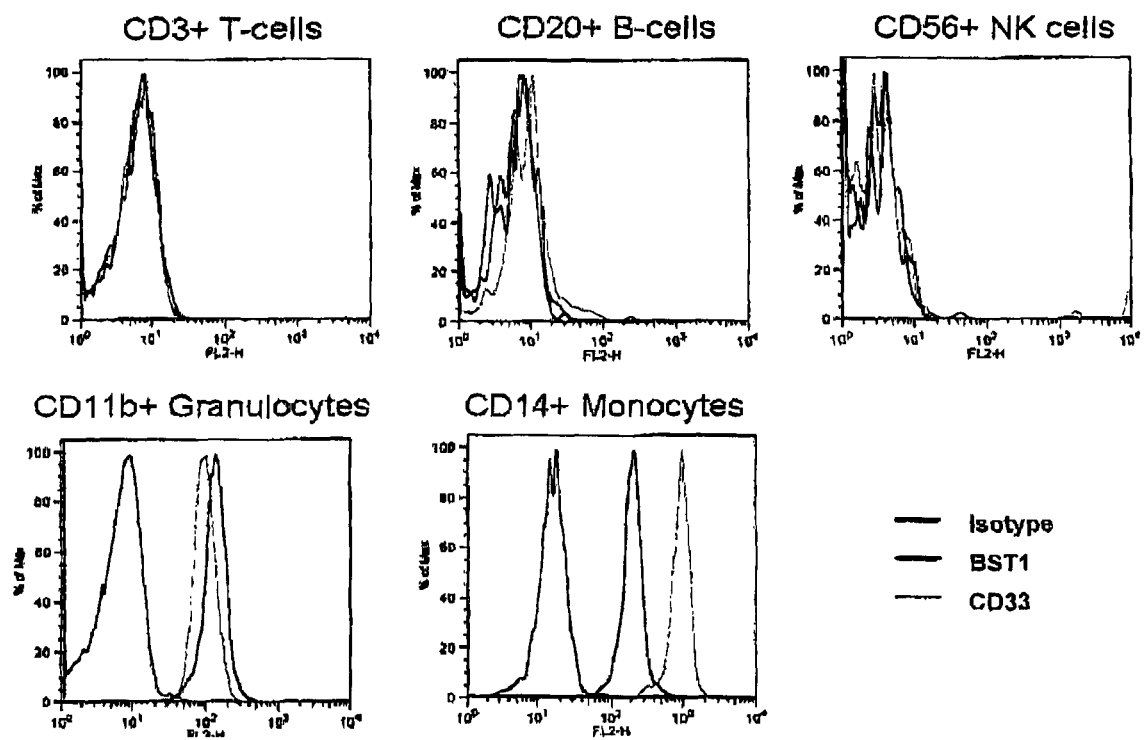
FIG. 4b shows the results of flow cytometric analysis of BST1 and CD33 on a subset of human leukocytes.

FIG. 4b shows the flow cytometric analysis of BST1 and CD33 on a subset of human leukocytes. The results revealed a comparable binding profile for the two targets in these cell classes. Strong binding of BST1 was observed in granulocytes and monocytes, both of which can be associated with and activated in diseases such as asthma, gout, crohns, lupus and diabetes. Monocytes are also implicated in the development of atherosclerotic plaques.

Figure 4C:
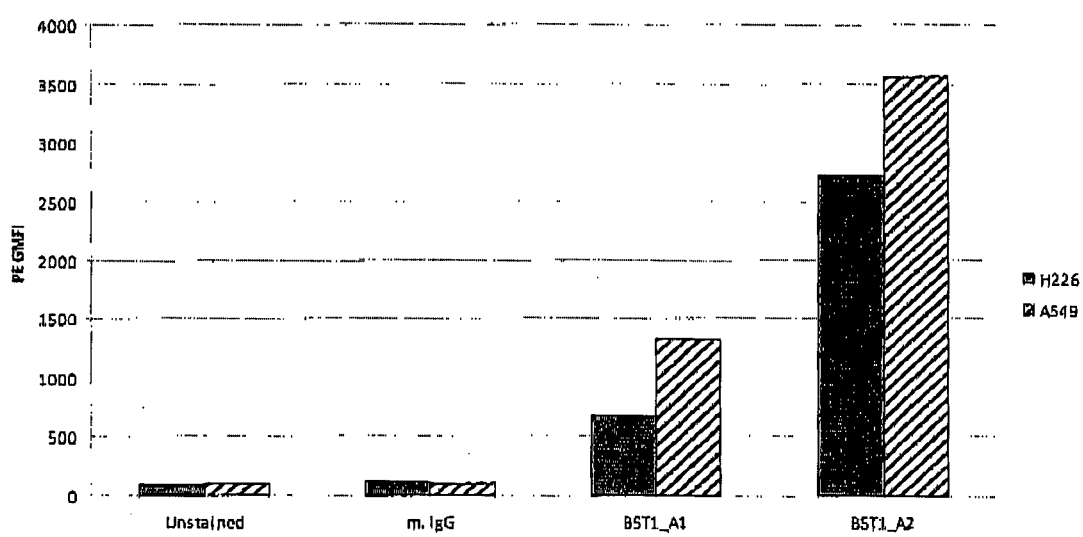
FIG. 4c shows results of flow cytometric anaysis of BST1 on A549 and H226 cells.

The results of the flow cytometry analysis demonstrated that 4 monoclonal antibodies designated BST1_A1 and BST1_A2 bound effectively to the cell-surface human BST1. FIG. 4c shows the binding specificities of both BST1_A1 and BST1_A2 to BST1 on A549 and H226 cells, respectively. The results indicate strong binding of those antibodies against BST1 on A549 and H226.

EXAMPLE 8

Structural Characterization of Monoclonal Antibodies to Tyrosine-Protein Kinase Transmembrane Receptor BST1

The cDNA sequences encoding the heavy and light chain variable regions of the BST1_A1 and BST1_A2 monoclonal antibodies were obtained using standard PCR techniques and were sequenced using standard DNA sequencing techniques.

The antibody sequences may be mutagenized to revert back to germline residues at one or more residues.

The nucleotide and amino acid sequences of the heavy chain variable region of BST1_A1 are SEQ ID NO: 18 and 14, respectively The nucleotide and amino acid sequences of the light chain variable region of BST1_A1 are SEQ ID NO: 19 and 15, respectively The nucleotide and amino acid sequences of the heavy chain variable region of BST1_A2 are SEQ ID NO: 20 and 16, respectively The nucleotide and amino acid sequences of the light chain variable region of BST1_A2 are SEQ ID NO: 21 and 17, respectively

EXAMPLE 9

Internalization and MabZAP of BST1_A1 and BST1_A2 in A549 and H226 Cells

Internalization of BST1_A1 and BST1_A2 by H226 and A549 were investigated using a MabZap assay. The MabZAP assay showed internalization of the anti-BST1 monoclonal antibodies through binding of an anti-human IgG secondary antibody conjugated to the toxin saporin.

(Advanced Targeting System, San Diego, Calif., IT-22-100). First, BST1 Fab was bound to the surface of the cells. Then, the MabZAP antibodies were bound to the primary antibodies. Next, the MabZAP complex was internalized by the cells. The entrance of Saporin into the cells resulted in protein synthesis inhibition and eventual cell death.

Figure 5A:
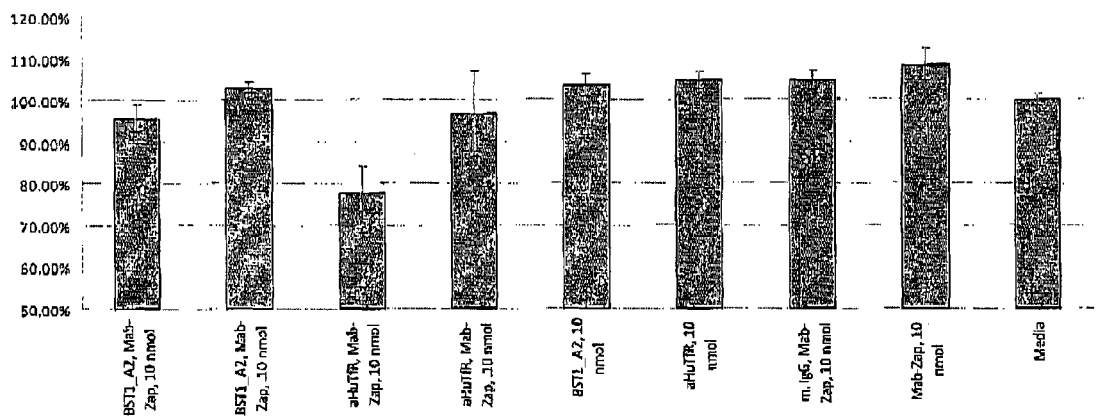
FIGS. 5a to 5b show the internalization of anti-BST1 monoclonal antibodies by A549 and H226 cells, using MabZAP assay.
Figure 5B:
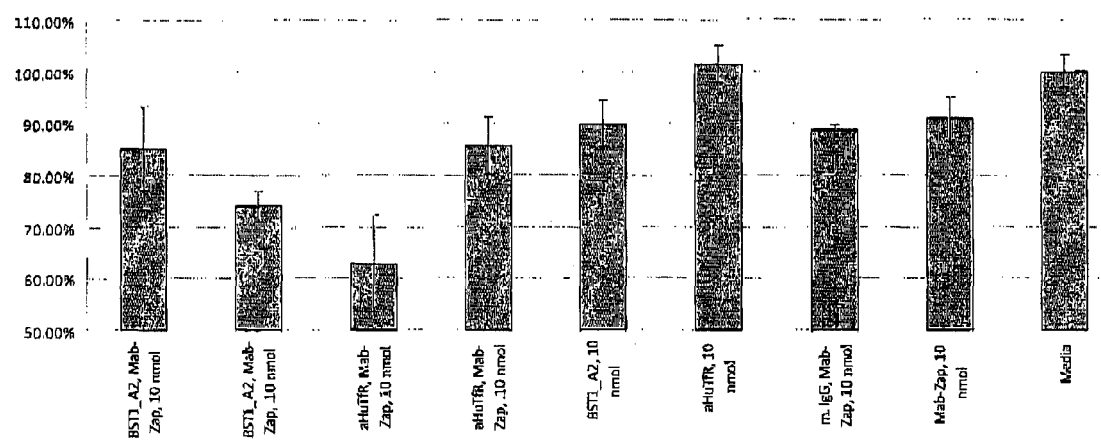

The MabZAP assay was conducted as follows. Each of the cells was seeded at a density of $5\times10^3$ cells per well. The anti-BST1 monoclonal antibody or an isotype control human IgG was serially diluted then added to the cells and incubated for 15 min at 25° C. The MabZAP was then added and incubated for 72 hr at 37° C. Cell viability in the plates was detected by CellTiter-Glo® Luminescent Cell Viability Assay kit (Promega, G7571) and the plates were read and analysed using Promega Glomax. Cell death was proportional to the concentration of anti-BST1 monoclonal antibodies. FIGS. 5a and 5b show that the anti-BST1 monoclonal antibodies, BST1_A1 and BST1_A2 were efficiently internalized by H226 and A549 cells, as compared to the anti-human IgG isotype control antibody.

EXAMPLE 10

Specificity of Monoclonal Antibodies to BST1 Determined by Flow Cytometry Analysis in AML Patients The ability of BST_A2 to bind to lymphoblasts from patients with AML was tested by Flow Cytometry Analysis. Blood was taken from 20 AML patients. Using the procedure as described in the Example 7, BST_A2 was show to bind to AML blasts of approx. 80% of the AML patients.

EXAMPLE 11

Antibody-Dependent Cellular Cytotoxicity Mediated by Anti-BST1 MAbs

Firstly 25 μl of parental and Non-Fucosylated anti-BST1 antibodies (BST1_A2 and BST1_A2 NF) at concentrations ranging from 10 nm/L to 0.1 nm/L were added to separate wells of a v bottom 96 well plate along with 50 μl of BST1-expressing A549 and U937 (histiocytic lymphoma cells) cells. 25 μl of Effector cells was then added to the wells to yield final effector:target (E:T) ratio of 10:1 and 25:1. The plate was then gently spun at 1000 rpm for 2 minutes, afterwhich it was incubated for 4 hrs in 37° C., 5% CO2 incubator. At 3 hrs post incubation, 10 μl of lysis solution was added to each of the wells containing BST1-expressing cells alone to measure maximum LDH release, and one set of wells containing media alone for volume correction control.

After the incubation, the cells were spun gently at 1000 rpm for 2 minutes, afterwhich 50 μl of supernatant was transfered to a flat bottom 96 well plate. Using the CytoTox 96® Non-Radioactive Cytotoxicity Assay available from Promega (Cat #: G1780), kit components were reconstituted according to manufacturer's specifications and 50 μl of the substrate mix was then added to each well. The plate was then covered and left to incubate for 30 minutes at 25° C. protected from light. Following this, 50 μl of Stop Solution was added to each well and the absorbance was recorded at 490 nm using the varioskan plate reader.

Figure 6A:
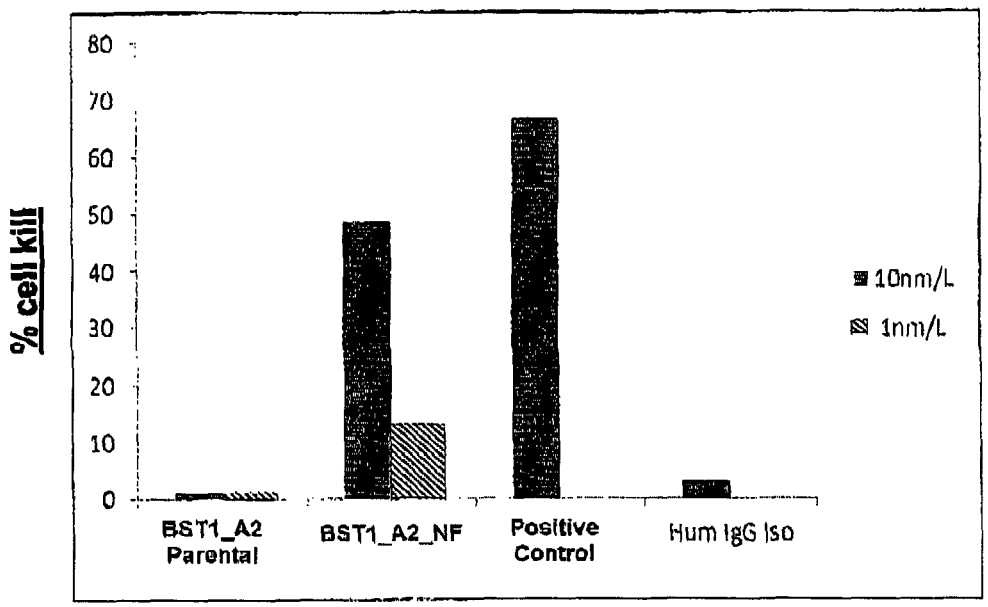
FIG. 6a and 6b show the ADCC activity of anti-BST1 monoclonal antibodies on BST1-expressing A549 (FIG. 6a) and U937 (FIG. 6b) cells.
Figure 6B:
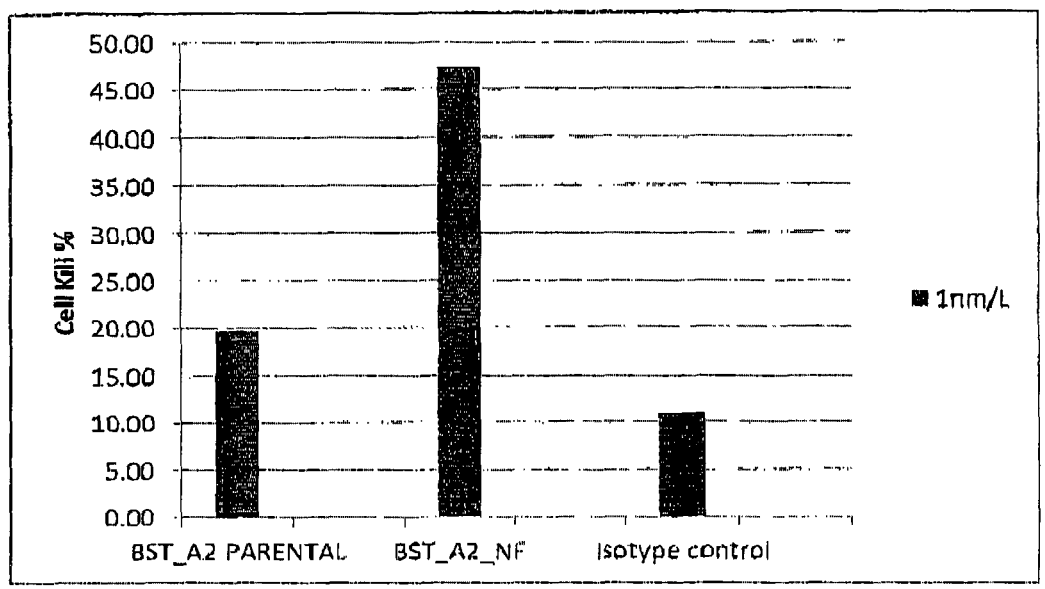

Using an antibody known to incite cell-kill via ADCC as a positive control and a human IgG1 isotype control as a negative control, the results show BST1_A2 and BST1_A2 NF were capable of eliciting ADCC on BST1-expressing A549 and U937 cells. On BST1-expressing A549 cells, BST1_A2 NF were shown to approximately 45% killing at 10 nmol/L (FIG. 6). On BST1-expressing U937 cells, BST1_A2 were shown to approximately 20% killing at 1 nmol/L and BST1_A2_NF were shown to approximately 45% killing at 1 nmol/L (FIG. 6b), thereby showing BST1_A2_NF would have a therapeutic effect in patients with AML and lung cancer.

SEQUENCE LISTING

| SEQ ID No | Description | Sequence |
|---|---|---|
| 1 | ADP-ribosyl cyclase 2 (BST1) | MAAQGCAASRLLQLLLQLLLLLLLLAAGGARARWRGEGTSAHLRDIFLGRCAEYRALL SPEQRNKNCTAIWEAFKVALDKDPCSVLPSDYDLFINLSRHSIPRDKSLFWENSHLLVN SFADNTRRFMPLSDVLYGRVADFLSWCRQKNDSGLDYQSCPTSEDCENNPVDSFWK RASIQYSKDSSGVIHVMLNGSEPTGAYPIKGFFADYEIPNLQKEKITRIEIWVMHEIGGP NVESCGEGSMKVLEKRLKDMGFQYSCINDYRPVKLLQCVDHSTHPDCALKSAAAATQ RKAPSLYTEQRAGLIIPLFLVLASRTQL |
| 2 | BST1 Peptide 1 | ALLSPEQR |
| 3 | BST1 Peptide 2 | DIFLGR |
| 4 | BST1 Peptide 3 | DMGFQYSCINDYRPVK |
| 5 | BST1 Peptide 4 | FMPLSDVLYGR |
| 6 | BST1 Peptide 5 | GEGTSAHLR |
| 7 | BST1 Peptide 6 | GFFADYEIPNLQK |
| 8 | BST1 Peptide 7 | LLQCVDHSTHPDCALK |
| 9 | BST1 Peptide 8 | SLFWENSHLLVNSFADNTR |
| 10 | BST1 Peptide 9 | VADFLSWCR |
| 11 | BST1 Peptide 10 | SLFWENSHLLVN |
| 12 | BST1 Peptide 11 | LKDMGFQYSCINDYRPVK |

SEQUENCE LISTING

| SEQ ID No | Description | Sequence |
|---|---|---|
| 13 | aa 29-292 of ADP-ribosyl cyclase 2 (BST1) | GARARWRGEGTSAHLRDIFLGRCAEYRALLSPEQRNKNCTAIWEAFKVALDKDPCSV<br>LPSDYDLFINLSRHSIPRDKSLFWENSHLLVNSFADNTRRFMPLSDVLYGRVADFLSW<br>CRQKNDSGLDYQSCPTSEDCENNPVDSFWKRASIQYSKDSSGVIHVMLNGSEPTGA<br>YPIKGFFADYEIPNLQKEKITRIEIWVMHEIGGPNVESCGEGSMKVLEKRLKDMGFQYS<br>CINDYRPVKLLQCVDHSTHPDCALKSAAATQRK |
| 14 | amino acid VH_A1 | MKQSTIALALLPLLFTPVAKAQVKLQQSGAELVRPGSSVKISCKASGYAFSNSWINWV<br>KQRPGQGLEWIGQIYPGDYDTNYNGKFKGKATLTADYSSSTAYMQLNSLTSEDSAVY<br>FCARGGSIYYGNLGFFDVWGAGTTVTVSSAKTTPPSVYPLAPGSAAQTNSMVTLGCL<br>VKGYFPEPVTVTWNSGSLSSGVHTFPAVLQSDLYTLSSSVTVPSSTWPSETVTCNVA<br>HPASSTKVDKKIVPRDCHHHHHH |
| 15 | amino acid VK_A1 | MKYLLPTAAAGLLLLAAQPAMAEMVLTQSPAIMSTSLGERVTMTCTASSRVSSSYLHW<br>YQQKPGSSPKLWIYSTSNLASGVPARFSGSGSGTSYSLTISSMEAEDAATYYCHQYH<br>RSPYTFGGGTKLEIKRADAAPTVSIFPPSSEQLTSGGASVVCFLNNFYPKDINVKWKID<br>GSERQNGVLNSWTDQDSKDSTYSMSSTLTLTKDEYERHNSYTCEATHKTSTSPIVKS<br>FNRNES |
| 16 | amino acid VH_A2 | MKQSTIALALLPLLFTPVAKAQAYLQQSGPELVKAGASVKMSCKASGYSFIEYTINWVK<br>QSHGKSLEWIGNIDPYYGTTYYNQMFTGKATLTVDQSSNTAYMQLKSLTSEDSAVYF<br>CARGSAWFPYWGQGTLVTVSAAKTTPPSVYPLAPGSAAQTNSMVTLGCLVKGYFPE<br>PVTVTWNSGSLSSGVHTFPAVLQSDLYTLSSSVTVPSSTWPSETVTCNVAHPASSTK<br>VDKKIVPRDCHHHHHH |
| 17 | amino acid VK_A2 | MKYLLPTAAAGLLLLAAQPAMADIVMSQSPAIMSASPGEKVTMTCSASSSVTYMYWY<br>QQKPGSSPRLLIYDTSNLASGVPVRFSGSGSGTSYSLTISRMEAEDTATYYCQQWSN<br>YPLTFGAGTKLELKRADAAPTVSIFPPSSEQLTSGGASVVCFLNNFYPKDINVKWKIDG<br>SERQNGVLNSWTDQDSKDSTYSMSSTLTLTKDEYERHNSYTCEATHKTSTSPIVKSF<br>NRNES |
| 18 | nt VH_A1 | ACGCTTTGTACATGGAGAAAATAAAGTGAAACAAAGCACTATTGCACTGGCACTCT<br>TACCGCTCTTATTTACCCCTGTGGCAAAAGCCCAGGTGAAGCTTCAGCAGTCCGG<br>GGCTGAGCTGGTGAGGCCTGGGTCCTCAGTGAAGATTTCCTGCAAGGCTTCTGGC<br>TACGCATTCAGTAACTCCTGGATAAACTGGGTGAAGCAGAGGCCTGGACAGGGTC<br>TTGAGTGGATTGGACAGATTTATCCTGGAGATTATGATACTAACTACAATGGAAAT<br>TCAAGGGTAAAGCCACACTGACTGCAGACTACTCCTCCAGCACAGCCTACATGCA<br>GCTCAACAGCCTAACATCTGAGGACTCTGCGGTCTATTTCTGTGCAAGGGGGGGA<br>TCGATCTACTATGGTAACCTCGGGTTCTTCGATGTCTGGGGCGCAGGGACCACGG<br>TCACCGTCTCCTCAGCCAAAACGACACCCCCATCTGTCTATCCACTGGCCCCTGG<br>ATCTGCTGCCCAAACTAACTCCATGGTGACCCTGGGATGCCTGGTCAAGGGCTAT<br>TTCCCTGAGCCAGTGACAGTGACCTGGAACTCTGGATCCCTGTCCAGCGGTGTGC<br>ACACCTTCCCAGCTGTCCTGCAGTCTGACCTCTACACTCTGAGCAGCTCAGTGACT<br>GTCCCCTCCAGCACCTGGCCCAGCGAGACCGTCACCTGCAACGTTGCCCACCCG<br>GCCAGCAGCACCAAGGTGGACAAGAAAATTGTGCCCAGGGATTGTCATCATCACC<br>ATCACCATCACTAATTGACAGCTTATCATCGATANGCT |
| 19 | nt VK_A1 | GTTTTTTTGGATGGAGTGAAACGATGAAATACCTATTGCCTACGGCAGCCGCTGGA<br>TTGTTATTACTCGCTGCCCAACCAGCCATGGCCGAAATGGTTCTCACCCAGTCTCC<br>AGCAATCATGTCTACATCTCTAGGGGAACGGGTCACCATGACCTGCACTGCCAGC<br>TCACGTGTAAGTTCCAGTTACTTGCACTGGTACCAGCAGAAGCCAGGATCCTCCC<br>CCAAACTCTGGATTTATAGTACATCCAACCTGGCTTCTGGAGTCCCAGCTCGCTTC<br>AGTGGCAGTGGGTCTGGGACCTCTTACTCTCTCACAATCAGCAGCATGGAGGCTG<br>AAGATGCTGCCACTTATTACTGCCACCAGTATCATCGTTCCCCGTACACGTTCGGA<br>GGGGGGACCAAGCTGGAAATAAAACGGGCTGATGCTGCACCAACTGTATCCATCT<br>TCCCACCATCCAGTGAGCAGTTAACATCTGGAGGTGCCTCAGTCGTGTGCTTCTTG<br>AACAACTTCTACCCCAAAGACATCAATGTCAAGTGGAAGATTGATGGCAGTGAACG<br>ACAAAATGGCGTCCTGAACAGTTGGACTGATCAGGACAGCAAAGACACCTAC<br>AGCATGAGCAGCACCCTCACGTTGACCAAGGACGAGTATGAACGACATAACAGCT<br>ATACCTGTGAGGCCACTCACAAGACATCAACTTCACCCATTGTCAAGAGCTTCAAC<br>AGGAATGAGTCTTAAGTGATTAGCTAATTCTAGAACG |
| 20 | nt VH_A2 | AAAACCCTGGCGTTACCCACGCTTTGTACATGGAGAAAATAAAGTGAAACAAAGCA<br>CTATTGCACTGGCACTCTTACCGCTCTTATTTACCCCTGTGGCAAAAGCCCAGGCT<br>TATCTACAGCAGTCTGGACCTGAGCTGGTGAAGGCTGGCGCTTCAGTGAAGATGT<br>CCTGCAAGGCTTCTGGTTACTCATTCATTGAGTACACCATAAACTGGGTGAAACAG<br>AGCCATGGAAAGAGCCTTGAGTGGATTGGAAATATTGATCCTTATTATGGAACCAC<br>TTATTACAATCAGATGTTCACGGGCAAGGCCACATTGACTGTAGACCAATCTTCCA<br>ACACTGCCTACATGCAGCTCAAGAGCCTGACATCTGAGGACTCTGCAGTCTATTTC<br>TGTGCAAGAGGCTCCGCCTGGTTTCCTTACTGGGGCCAGGGGACTCTAGTCACTG<br>TCTCTGCAGCCAAAACGACACCCCCATCTGTCTATCCACTGGCCCCTGGATCTGCT<br>GCCCAAACTAACTCCATGGTGACCCTGGGATGCCTGGTCAAGGGCTATTTCCCTG<br>AGCCAGTGACAGTGACCTGGAACTCTGGATCCCTGTCCAGCGGTGTGCACACCTT<br>CCCAGCTGTCCTGCAGTCTGACCTCTACACTCTGAGCAGCTCAGTGACTGTCCCC |

SEQUENCE LISTING

| SEQ ID No | Description | Sequence |
|---|---|---|
| | | TCCAGCACCTGGCCCAGCGAGACCGTCACCTGCAACGTTGCCCACCCGGCCAGC<br>AGCACCAAGGTGGACAAGAAAATTGTGCCCAGGGATTGTCATCATCACCATCACC<br>ATCACTAATTGACAGCTTATCATCGAT |
| 21 | nt VK_A2 | ACTCTCTACTGTTTCTCCATACCCGTTTTTTTGGATGGAGTGAAACGATGAAATACC<br>TATTGCCTACGGCAGCCGCTGGATTGTTATTACTCGCTGCCCAACCAGCCATGGC<br>CGACATCGTTATGTCTCAGTCTCCAGCAATCATGTCTGCATCTCCAGGGGAGAAG<br>GTCACCATGACCTGCAGTGCCAGCTCAAGTGTAACTTACATGTACTGGTACCAGCA<br>GAAGCCAGGATCCTCCCCCAGACTCCTGATTTATGACACATCCAACCTGGCTTCTG<br>GAGTCCCTGTTCGCTTCAGTGGCAGTGGGTCTGGGACCTCTTACTCTCTCACAATC<br>AGCCGAATGGAGGCTGAAGATACTGCCACTTATTACTGCCAGCAGTGGAGTAATTA<br>CCCACTCACGTTCGGTGCTGGGACCAAGCTGGAGCTGAAACGGGCTGATGCTGC<br>ACCAACTGTATCCATCTTCCCACCATCCAGTGAGCAGTTAACATCTGGAGGTGCCT<br>CAGTCGTGTGCTTCTTGAACAACTTCTACCCCAAAGACATCAATGTCAAGTGGAAG<br>ATTGATGGCAGTGAACGACAAAATGGCGTCCTGAACAGTTGGACTGATCAGGACA<br>GCAAAGACAGCACCTACAGCATGAGCAGCACCCTCACGTTGACCAAGGACGAGTA<br>TGAACGACATAACAGCTATACCTGTGAGGCCACTCACAAGACATCAACTTCACCCA<br>TTGTCAAGAGCTTCAACAGGAATGAGTCTTAAGTGATTAGCTAATTCTAGAACGCG<br>TCACTTGGCACTGGCCGTCGTTTTA |

The invention claimed is:

1. A method for the treatment of disease wherein BST1 is expressed in said disease, comprising administering to a subject in need thereof a therapeutically effective amount of an antibody, or a functional fragment thereof, which binds to BST1, wherein said disease is acute myeloid leukemia (AML).

2. The method according to claim 1, wherein the antibody, or functional fragment thereof, binds specifically to BST1.

3. The method according to claim 2, wherein the antibody is a monoclonal antibody.

4. The method according to claim 2, wherein the antibody, or functional fragment thereof, is a chimeric antibody, a human antibody, a humanized antibody, a single chain antibody, a defucosylated antibody or a bispecific antibody.

5. The method according to claim 2, wherein the functional antibody fragment is a UniBody, a domain antibody or a Nanobody.

6. The method according to claim 1, wherein the antibody, or functional fragment thereof, contains or is conjugated to a therapeutic moiety.

7. The method according to claim 6, wherein the therapeutic moiety is a cytotoxic moiety or a radioactive isotope.

8. The method according to claim 6, wherein the antibody, or functional fragment thereof, is an antibody drug conjugate.

9. The method according to claim 1, wherein the antibody, or functional fragment thereof, elicits antibody-dependent cellular cytotoxicity (ADCC).

10. The method according to claim 1, wherein the antibody, or functional fragment thereof, elicits complement dependent cytotoxicity (CDC).

11. The method according to claim 1, wherein the antibody or, functional fragment thereof, elicits T-cell cytotoxicity.

12. The method according to claim 1, wherein the antibody, or functional fragment thereof, induces apoptosis of cancer cells, kills or reduces the number of cancer stem cells, and/or kills or reduces the number of circulating cancer cells.

13. The method according to claim 1, wherein the antibody, or functional fragment thereof, modulates a physiological function of BST1, inhibits ligand binding to BST1, and/or inhibits a signal transduction pathway mediated by BST1.

14. The method according to claim 1, wherein the subject is a human.

* * * * *